(12) United States Patent
Barnett et al.

(10) Patent No.: US 7,740,662 B2
(45) Date of Patent: Jun. 22, 2010

(54) MOBILE/FIXED PROSTHETIC KNEE SYSTEMS

(75) Inventors: Gary D. Barnett, Wabash, IN (US); Thomas S. Camino, Fort Wayne, IN (US); William P. Barrett, Seattle, WA (US); Steve MacDonald, London (CA); Thomas K. Fehring, Charlotte, NC (US); John Bohannon Mason, Charlotte, NC (US); Stephen A. Hazebrouck, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 90 days.

(21) Appl. No.: 11/859,448

(22) Filed: Sep. 21, 2007

(65) Prior Publication Data
US 2008/0114464 A1 May 15, 2008

Related U.S. Application Data

(60) Provisional application No. 60/829,432, filed on Oct. 13, 2006, provisional application No. 60/829,430, filed on Oct. 13, 2006.

(51) Int. Cl.
*A61F 2/38* (2006.01)

(52) U.S. Cl. .............. 623/20.33; 623/20.32; 623/20.14

(58) Field of Classification Search .............. 623/20.14, 623/20.28, 20.21, 20.32, 20.33, 0.342, 0.34
See application file for complete search history.

(56) References Cited

U.S. PATENT DOCUMENTS

| 4,205,400 | A |   | 6/1980  | Shen et al.   |           |
|-----------|---|---|---------|---------------|-----------|
| 4,217,666 | A |   | 8/1980  | Averill       |           |
| 4,501,031 | A |   | 2/1985  | McDaniel et al. |         |
| 5,108,442 | A |   | 4/1992  | Smith         |           |
| 5,326,358 | A |   | 7/1994  | Aubriot et al. |          |
| 5,370,699 | A |   | 12/1994 | Hood et al.   |           |
| 5,489,311 | A | * | 2/1996  | Cipolletti    | 623/20.34 |
| 5,879,391 | A |   | 3/1999  | Slamin        |           |
| 5,951,603 | A | * | 9/1999  | O'Neil et al. | 623/20.33 |
| 6,090,144 | A |   | 7/2000  | Letot et al.  |           |
| 6,210,444 | B1|   | 4/2001  | Webster et al. |          |
| 6,391,283 | B1|   | 5/2002  | Jensen et al. |           |
| 6,660,039 | B1|   | 12/2003 | Evans et al.  |           |

(Continued)

FOREIGN PATENT DOCUMENTS

EP          0682925        6/1992

(Continued)

OTHER PUBLICATIONS

PCT Search Report for PCT Application No. PCT/US2007/080796, Feb. 18, 2008, 9 pgs.

*Primary Examiner*—David Isabella
*Assistant Examiner*—Yashita Sharma
(74) *Attorney, Agent, or Firm*—Barnes & Thornburg LLP

(57) ABSTRACT

A prosthetic knee system includes a tibial tray, a non-rotating tibial insert, and a rotating tibial insert. The non-rotating tibial insert and the rotating tibial insert are selectively couplable to the tibial tray such that a fixed or a mobile orthopaedic prosthesis may be configured. In some embodiments, the tibial tray may be a fixed or mobile tibial tray. Additionally, in some embodiments, the prosthetic knee system may include a femoral component.

5 Claims, 67 Drawing Sheets

U.S. PATENT DOCUMENTS

| | | |
|---|---|---|
| 6,755,864 B1 | 6/2004 | Brack et al. |
| 2002/0072802 A1 | 6/2002 | O'Neil et al. |
| 2002/0120341 A1 | 8/2002 | Stumpo et al. |
| 2003/0009232 A1 | 1/2003 | Metzger et al. |
| 2004/0034432 A1 | 2/2004 | Hughes et al. |
| 2004/0215345 A1 | 10/2004 | Perrone et al. |
| 2004/0267371 A1 | 12/2004 | Hayes et al. |
| 2005/0027365 A1 | 2/2005 | Burstein et al. |
| 2005/0222686 A1 | 10/2005 | Brehm |
| 2005/0246027 A1 | 11/2005 | Metzger et al. |

FOREIGN PATENT DOCUMENTS

| | | |
|---|---|---|
| EP | 0904748 | 3/1999 |
| EP | 0904749 | 3/1999 |
| EP | 0956836 | 5/1999 |
| EP | 0925765 | 6/1999 |
| EP | 1025818 | 8/2000 |
| EP | 1702590 | 9/2006 |
| WO | 03065939 | 8/2003 |

* cited by examiner

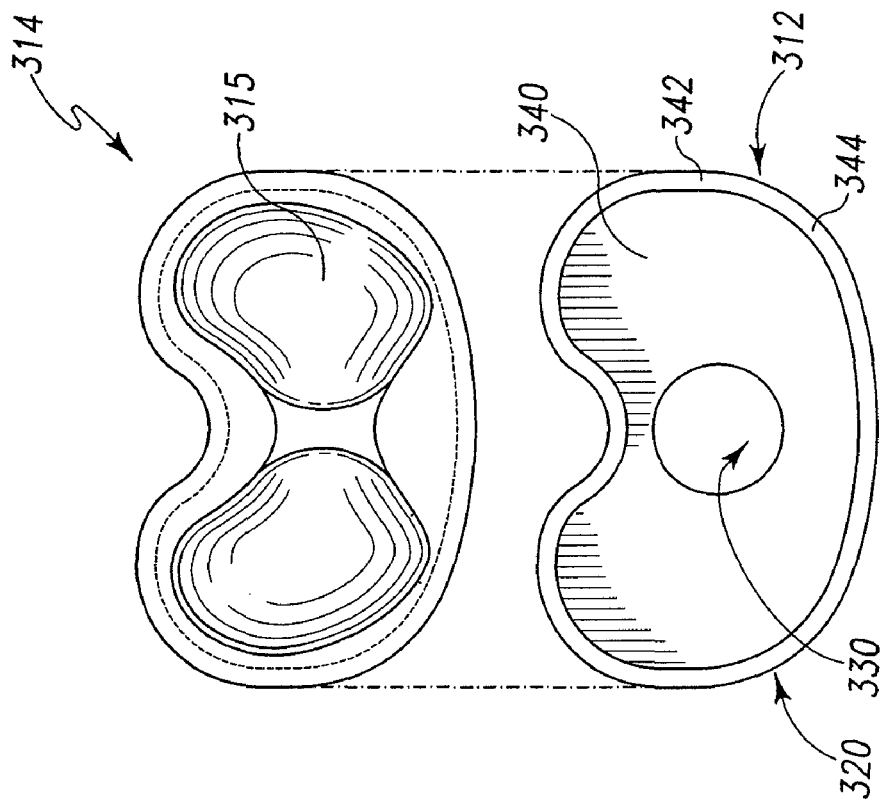
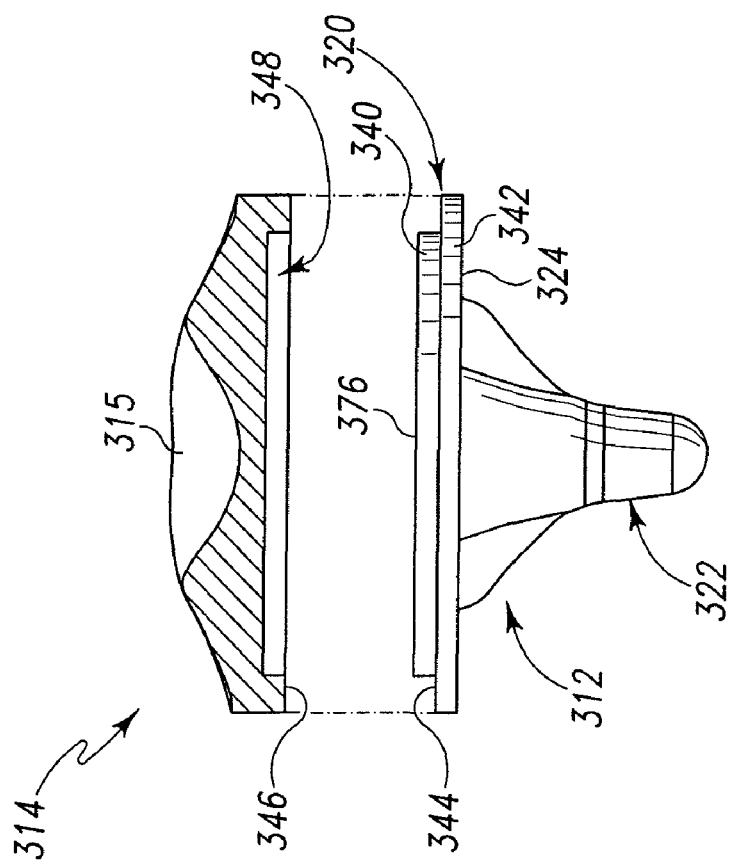

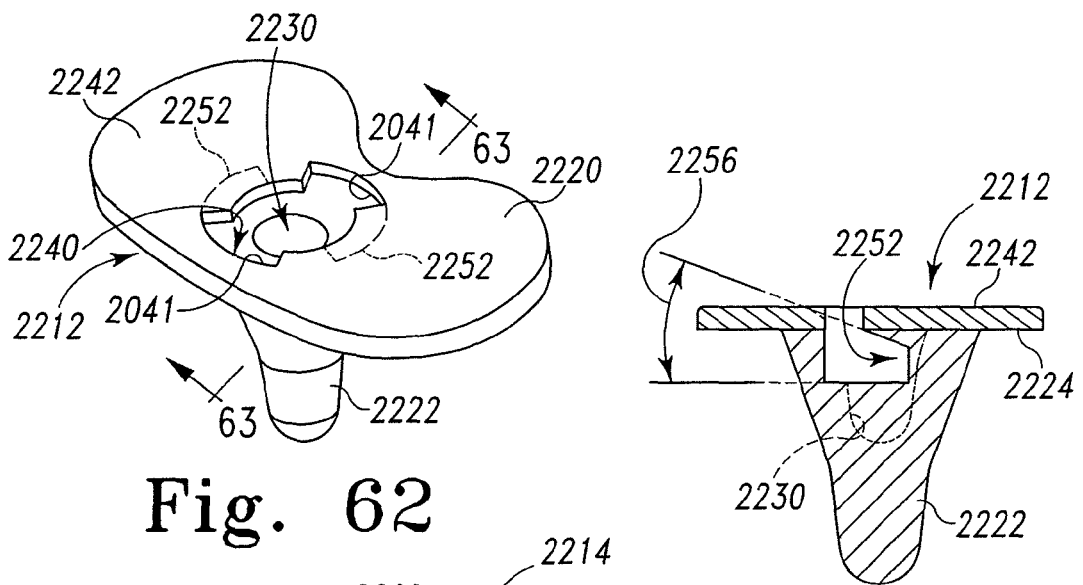
Fig. 62
Fig. 63
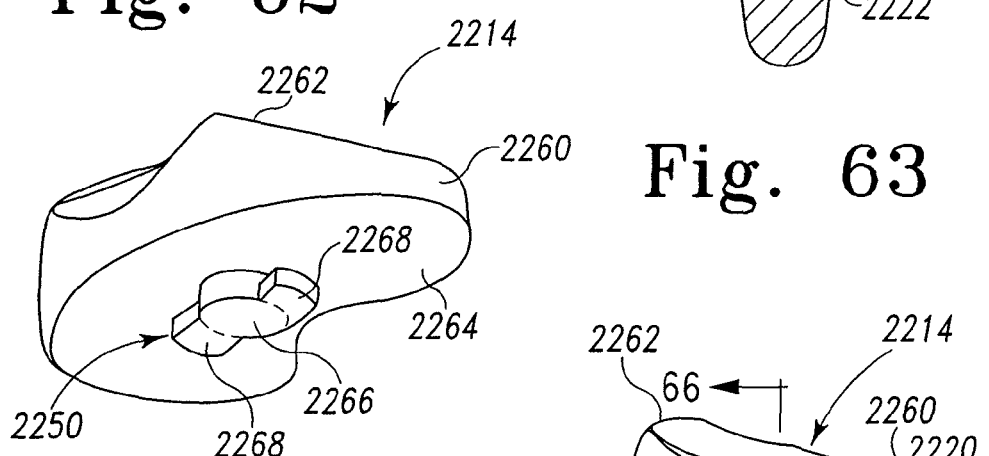
Fig. 64
Fig. 65
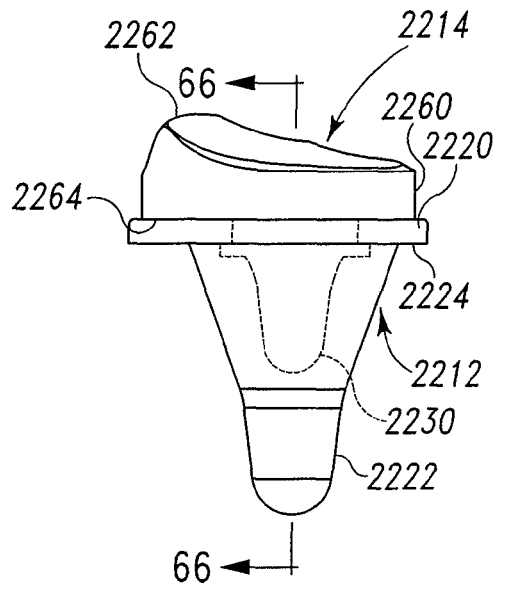
Fig. 66

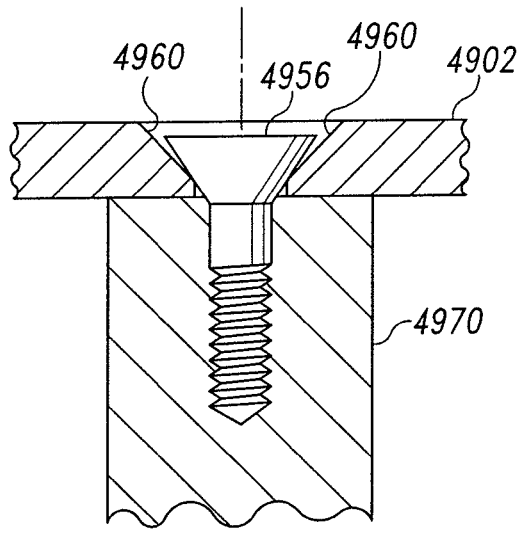
Fig. 115
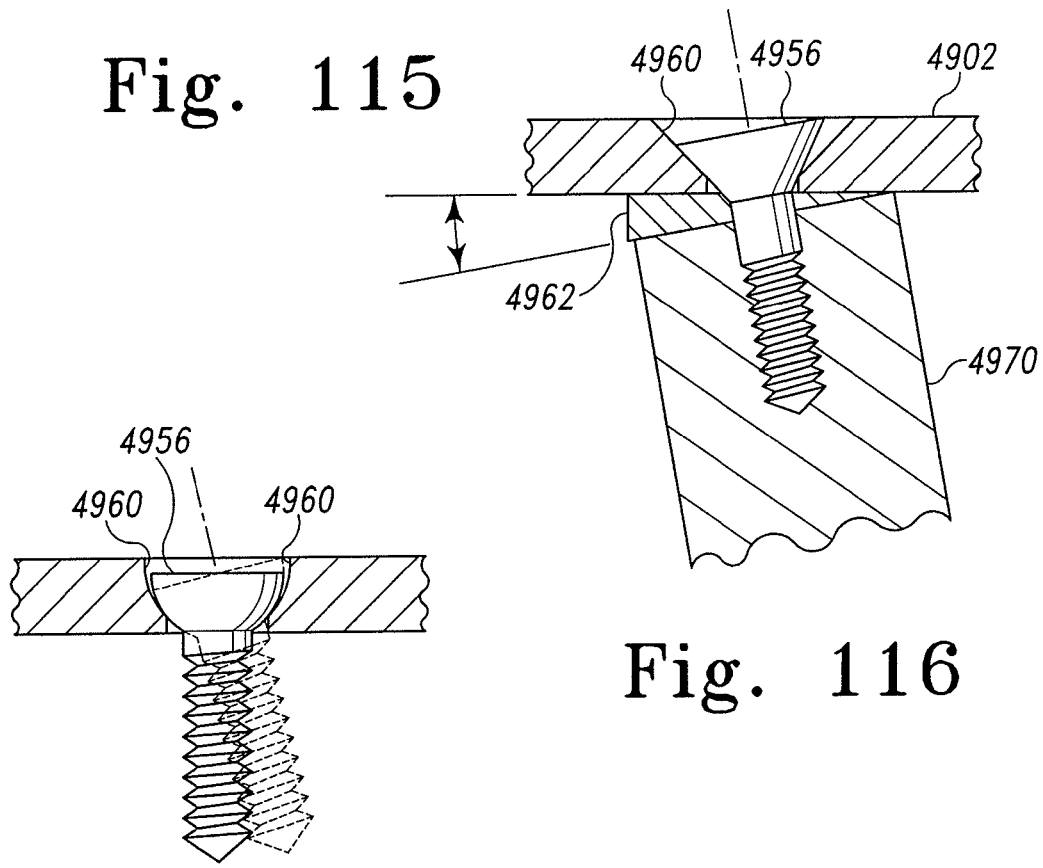
Fig. 116
Fig. 117

MOBILE/FIXED PROSTHETIC KNEE SYSTEMS

This patent application claims priority to and the benefit of U.S. Provisional Patent Application Ser. No. 60/829,432 entitled "Mobile/Fixed Prosthetic Knee Systems," which was filed on Oct. 13, 2006 by Luke J. Aram, et al. and to U.S. Provisional Patent Application Ser. No. 60/829,430 entitled "Mobile/Fixed Prosthetic Knee System," which was filed on Oct. 13, 2006 by Stephen A. Hazebrouck, et al., the entirety of each of which is expressly incorporated herein by reference.

CROSS-REFERENCE TO RELATED U.S. PATENT APPLICATION

Cross-reference is made to U.S. Utility patent application Ser. No. 11/859,442 entitled "Mobile/Fixed Prosthetic Knee Systems," which was filed on Sep. 21, 2007 by Daniel D. Auger et al., to U.S. Utility patent application Ser. No. 11/859,451 entitled "Mobile/Fixed Prosthetic Knee Systems," which was filed on Sep. 21, 2007 by Luke J. Aram et al., to U.S. Utility patent application Ser. No. 11/859,448 entitled "Mobile/Fixed Prosthetic Knee Systems," which was filed on Sep. 21, 2007 by Stephen A. Hazebrouck et al., and to U.S. Utility patent application Ser. No. 11/859,425 entitled "Mobile/Fixed Prosthetic Knee Systems," which was filed on Sep. 21, 2007 by John A. Bonitati et al., the entirety of each of which is expressly incorporated herein by reference.

TECHNICAL FIELD

The present disclosure relates generally to an orthopaedic prosthesis, and more particularly to a knee prosthesis. Specifically, the present disclosure relates to the tibial and bearing components of a knee prosthesis.

BACKGROUND

Movement (e.g., flexion and extension) of the natural human knee involves movements of the femur and the tibia. Specifically, during flexion and extension, the distal end of the femur and the proximal end of the tibia articulate relative to one another through a series of complex movements. Damage (e.g., trauma) or disease can deteriorate the bones, articular cartilage, and ligaments of the knee, which can ultimately affect the ability of the natural knee to function in such a manner. As a result, knee prostheses have been developed and implanted into surgically prepared ends of the femur and tibia.

A typical knee prosthesis for a total knee replacement, for example, includes a tibial component or tibial tray coupled to the patient's tibia, a femoral component coupled to the patient's femur, and a bearing component (or tibial insert) positioned between the tibial tray and the femoral component and including a bearing surface to accommodate the condyles of the femoral component. In some situations, it may be desirable that the tibial insert rotate relative to the tibial tray. Such rotation more closely replicates the motion of the patient's natural anatomy. In other cases, however, it may be desirable to prevent the tibial insert from rotating relative to the tibial tray. For example, various ligaments which support the knee may be compromised or damaged. In such a case, rotation of the tibial insert relative to the tibial tray may create an unstable knee. As such, a surgeon will decide on a case-by-case basis whether to use a rotating or non-rotating tibial assembly. This decision may be made pre-operatively or intra-operatively, for example. Additionally, it may be desirable to change a rotating tibial insert to a non-rotating tibial insert during a revision type surgery, for example.

SUMMARY

According to one aspect, an orthopaedic prosthesis assembly may include a tibial tray configured to be coupled to a surgically-prepared surface of the proximal end of a tibia and a tibial insert coupled to the tibial tray. The tibial tray may include a platform having an upper surface and a bottom surface. The tibial tray may also include a cavity having an opening defined in the upper surface of the platform. The cavity may be defined by a sidewall.

The tibial insert may include a polymer bearing, a metal base, and a metal stem. The polymer bearing may include an upper bearing surface configured to contact a pair of femoral condyles and a bottom surface. The metal base may include an upper surface secured to the bottom surface of the polymer bearing and a bottom surface in contact with the upper surface of the tibial tray. The metal stem may extend downwardly from the bottom surface of the base. The metal stem may be received in the cavity of the tibial tray. In some embodiments, the sidewall defining the cavity and the metal stem may have corresponding tapers such that the sidewall and the metal stem are in contact and form a friction lock therebetween. For example, the sidewall defining the cavity may have a Morse taper and the metal stem may have a Morse taper corresponding to the Morse taper of the sidewall. Additionally, in some embodiments, the metal base includes a macro-texturized layer defined on the upper surface. The polymer bearing may be compression molded to the metal base.

In some embodiments, the orthopaedic prosthesis may also include a rotating tibial insert. The tibial insert may be removably coupled to the tibial tray. The rotating tibial insert may be configured to be coupled to the tibial tray when the tibial insert is removed therefrom. The rotating tibial insert may be free to rotate about an axis relative to the tibial tray when coupled thereto. The rotating tibial insert may include a stem extending from a bottom surface. In such embodiments, the stem may be configured to be received in the cavity of the tibial tray when the rotating tibial insert is coupled thereto.

According to another aspect, an orthopaedic prosthesis may include a tibial tray, a tibial insert, and a screw. The tibial tray may be configured to be coupled to a surgically-prepared surface of the proximal end of a tibia. The tibial tray may include a platform having an upper surface and a bottom surface. The tibial tray may also include a cavity defined by an inner sidewall and having an opening defined in the upper surface of the platform.

The tibial insert may be coupled to the tibial tray and may include an upper bearing surface configured to contact a pair of femoral condyles. Additionally, the tibial insert may include a bottom surface in contact with the upper surface of the tibial tray and a stem extending downwardly from the bottom surface and received in the cavity of the tibial tray. The stem may include a distal end having a threaded internal passageway.

The screw may be positionable in the threaded internal passageway of the stem. The distal end of the stem may have a first width when the screw is positioned in the threaded internal passageway and may have a second width when the screw is removed from the threaded internal passageway. The first width may be greater than the second width. Additionally, in some embodiments, the distal end of the stem may include a vertical slit, which is sized to allow the width of the distal end of the stem to be increased. In some embodiments, the stem may include an outer wall. The outer wall may be forced against the inner sidewall of the tibial tray when the screw is positioned in the first position. Additionally, in some embodiments, the inner sidewall of the tibial tray may include a slot defined therein and the distal end of the stem may include an outer rim. In such embodiments, the outer rim may be received in the slot of the inner sidewall.

Accordingly to further aspect, an orthopaedic prosthesis may include a tibial tray, a tibial insert, and a stem. The tibial tray may be configured to be coupled to a surgically-prepared surface of the proximal end of a tibia. The tibial tray may include a platform, a first track, and a second track. The platform may have an upper surface and a bottom surface. The first track may be defined in the upper surface of the platform. Similarly, the second track may be defined in the upper surface of the platform. The tibial tray may also include a cavity having an opening defined the upper surface between the first track and the second track.

The tibial insert may be coupled to the tibial tray. The tibial insert may include an upper bearing surface, a bottom surface, and first and second rails. The upper bearing surface may be configured to contact a pair of femoral condyles. The bottom surface may be in contact with the upper surface of the tibial tray. The first rail may extend downwardly from the bottom surface and be received in the first track of the tibial tray. Similarly, the second rail may extend downwardly from the bottom surface and be received in the second track. The tibial insert may also include a passageway defined therethrough. The passageway may include a first opening defined in the upper bearing surface and a second opening defined in the bottom surface. The tibial insert may be positioned relative to the tibial tray such that the passageway is in registry with the opening of the cavity of the tibial tray.

The stem may be coupled to the tibial insert and the tibial tray. For example, the stem may be received in the passageway of the tibial insert and extend through aperture of the tibial tray. In some embodiments, each of the first track, the second track, the first rail, and the second rail may have a substantially dovetail cross-section, a substantially rectangular cross-section, and/or a substantially T-shaped cross-section. Additionally, the first track and the first rail may have correspondingly shaped cross-sections. The second track and the second rail have correspondingly shaped cross-sections that are different from the cross-sections of the first track and the first rail.

In some embodiments, the stem may include an internal passageway. The tibial tray may include an aperture defined at a distal end of the cavity. In such embodiments, the orthopaedic prosthesis assembly may further include a fastener received in the passageway of the stem and the threaded aperture of the tibial tray to secure the tibial insert to the tibial tray in a fixed position. Further, in some embodiments, the orthopaedic prosthesis assembly may include a rotating tibial insert. In such embodiments, the rotating tibial insert may be configured to be coupled to the tibial tray when the tibial insert is removed therefrom. The rotating tibial insert may be free to rotate about an axis relative to the tibial tray.

According to yet another aspect, an orthopaedic prosthesis may include a tibial tray, a tibial insert, and a metal rim. The tibial tray may be configured to be coupled to a surgically-prepared surface of the proximal end of a tibia. The tibial tray may include a platform. The platform may have an upper surface, a bottom surface, and a side surface extending between the upper surface and the bottom surface. The side surface may have a taper.

The tibial insert may be coupled to the tibial tray. The tibial insert may include an upper bearing surface, a bottom surface, and a side surface extending between the upper bearing surface and the bottom surface. The upper bearing surface may be configured to contact a pair of femoral condyles. The bottom surface may be in contact with the upper surface of the tibial tray.

The metal rim may be secured to the side surface of the tibial insert and may extend downwardly with respect to the bottom surface of the tibial insert. The metal rim may have a taper corresponding to the taper of the side surface of the tibial tray such that the metal rim and side surface of the tibial tray are in contact and form a friction lock therebetween. For example, the side surface of the tibial insert may include a Morse taper and the metal rim may include a Morse taper corresponding to the Morse taper of the side surface of the tibial insert.

In some embodiments, the tibial tray may include a cavity defined in the platform. The cavity may be defined by a sidewall. Additionally, the tibial insert may include a stem extending downwardly from the bottom surface and being received in the cavity of the tibial tray. In such embodiments, the orthopaedic prosthesis assembly may further include a metal ring secured to the stem. The sidewall defining the cavity and the metal ring may include corresponding tapers such that the sidewall and the metal ring are in contact and form a friction lock therebetween. Further, in some embodiments, the tibial insert may include a passageway having an opening defined in the upper surface and extending through the stem. Similarly, the tibial tray may include a threaded aperture defined at a distal end of the cavity. In such embodiments, the orthopaedic prosthesis assembly may further include a fastener received in the passageway of the tibial insert and the threaded aperture of the tibial tray to secure the tibial insert to the tibial tray. The tibial tray may also include a slot defined in the side surface. The slot may define a closed path. The tibial insert may include a tab extending from an inner surface of the metal rim. The tab may also define a closed path and be received in the slot of the tibial tray.

According to yet a further aspect, an orthopaedic prosthesis may include a tibial tray, a tibial insert, and a metal ring. The tibial tray may be configured to be coupled to a surgically-prepared surface of the proximal end of a tibia. The tibial insert coupled to the tibial tray and the metal ring secured to the side surface of the tibial insert. The tibial tray may be include a platform having an upper surface and a bottom surface and a rim extending upwardly from the upper surface of the platform. The rim may define a closed path and may have a taper.

The tibial insert may include an upper bearing surface, a substantially planar bottom surface, and a side surface extending between the upper bearing surface and the bottom surface. The upper bearing surface may be configured to contact a pair of femoral condyles. The substantially planar bottom surface may be in contact with the upper surface of the platform of the tibial tray.

The metal ring may include a bottom surface substantially co-planar with the bottom surface of the tibial insert. The metal ring may have a taper corresponding to the taper of the rim of the tibial tray such that the metal ring and the rim of the tibial tray are in contact and form a friction lock therebetween. For example, the sidewall of the tibial insert may have a Morse taper and the metal ring may have a Morse taper corresponding to the Morse taper of the rim of the tibial insert.

BRIEF DESCRIPTION OF THE DRAWINGS

The detailed description particularly refers to the following figures, in which:

FIG. 10 is a part-side, part-sectional view of a tibial tray and a non-rotating tibial insert configured to be coupled with the tibial tray;

FIG. 11 is a top view of the tibial tray and the tibial insert of FIG. 10;

FIG. 23 is a sectional view of the tibial tray, tibial insert, and the posts of FIG. 22a;

FIG. 62 is a perspective view of another tibial tray;

FIG. 63 is a sectional view taken along line 63-63 of FIG. 62;

FIG. 64 is a perspective view of another tibial insert configured to be used with the tibial tray of FIG. 62;

FIG. 65 is a side view of the tibial insert of FIG. 64 coupled to the tibial tray of FIGS. 62 and 63;

FIG. 66 is a sectional view taken along line 66-66 of FIG. 65;

FIG. 115 is an enlarged sectional view of one embodiment of the tibial tray of the FIG. 112;

FIG. 116 is an enlarged section view of another embodiment of the tibial tray of FIG. 112;

FIG. 117 is an enlarged section view of another embodiment of the tibial tray of FIG. 112;

FIG. 118 is an exploded bottom perspective view of another embodiment of the orthopaedic prosthesis assembly of FIG. 109;

FIG. 119 is a top plan view of a stem of the orthopaedic prosthesis assembly of FIG. 118;

FIG. 120 is a top perspective view of the stem of FIG. 119;

FIG. 121 is a bottom perspective view of another embodiment of an orthopaedic prosthesis assembly; and FIG. 122 is front elevation view of the orthopaedic prosthesis assembly of FIG. 121.

DETAILED DESCRIPTION OF THE DRAWINGS

Figure 1:
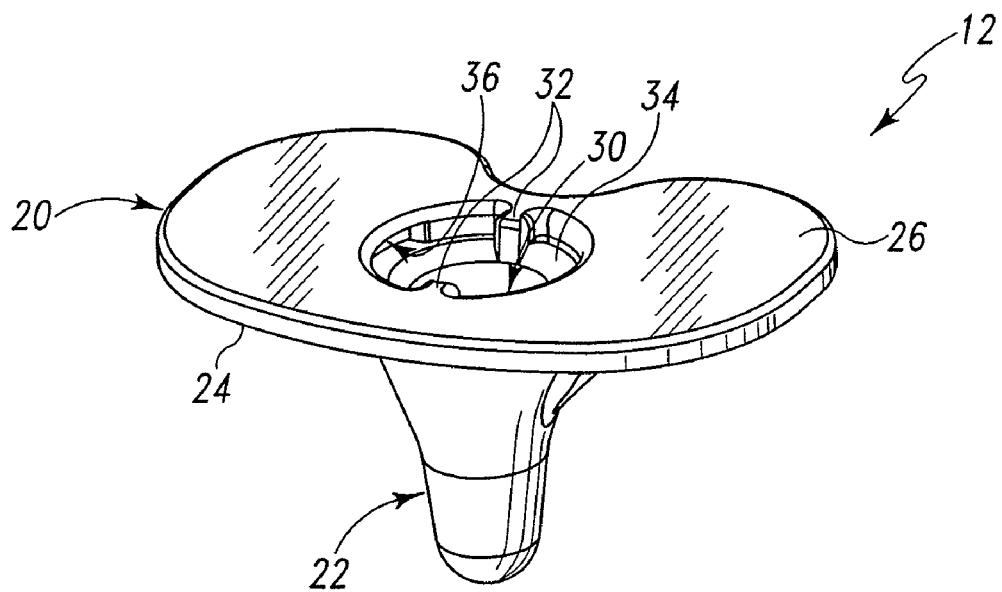
FIG. 1 is a perspective view of a tibial tray including generally "C-shaped" cutout recesses.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives falling within the spirit and scope of the invention as defined by the appended claims.

Various prosthetic knee systems are described within the present disclosure. Such prosthetic knee systems may include one or more tibial trays, one or more tibial inserts, and/or one or more locking mechanisms or other components associated with the aforementioned tray(s) and insert(s). A first combination of these components of the prosthetic knee systems disclosed herein provides a rotating tibial assembly whereby the tibial insert is able to rotate about a longitudinal axis relative to the tibial tray. A second combination of the components of the prosthetic knee systems disclosed herein provides a non-rotating or fixed knee assembly whereby the tibial insert is fixed relative to the tibial tray and is not able to rotate about the longitudinal axis. As such, many of the knee prosthetic systems disclosed herein include components which may be arranged to provide for both a rotating knee assembly and a non-rotating knee assembly.

Figure 2:
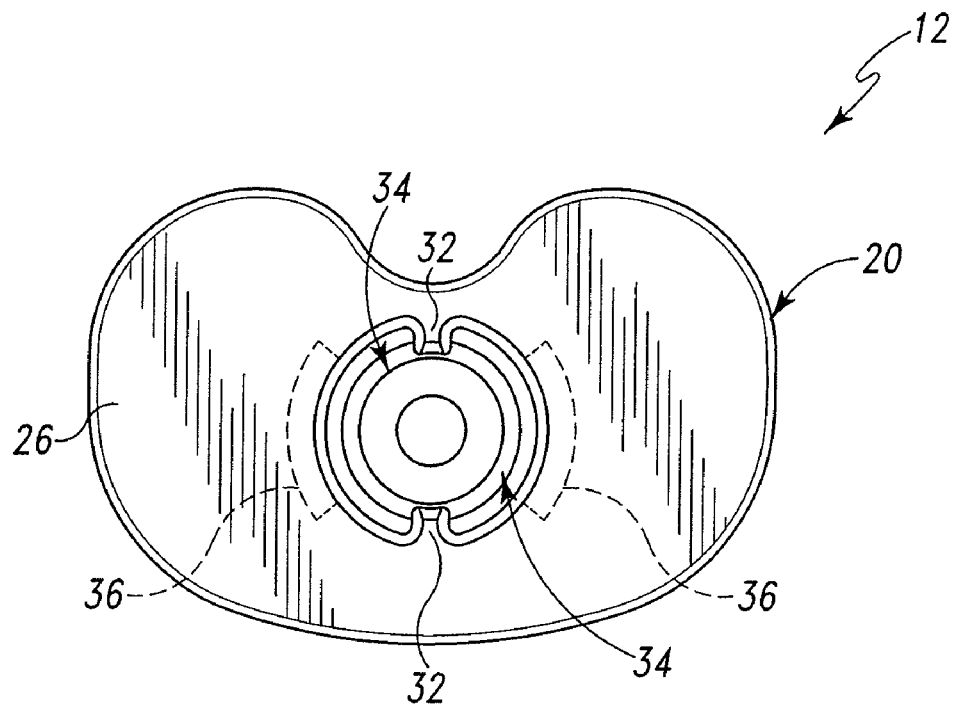
FIG. 2 is a top view of the tibial tray of FIG. 1.
Figure 3:
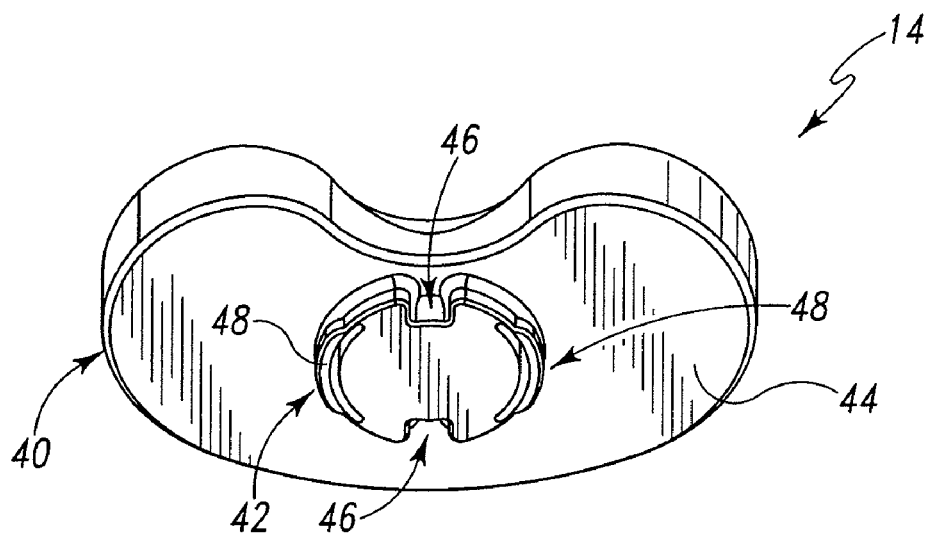
FIG. 3 is a bottom perspective view of a non-rotating or fixed tibial insert for use with the tibial tray of FIGS. 1 and 2.
Figure 4:
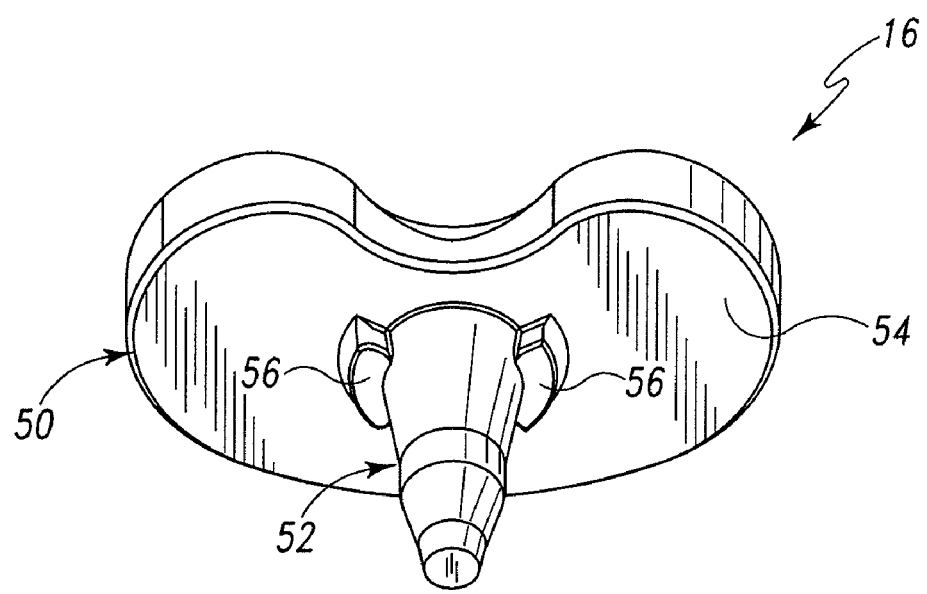
FIG. 4 is a bottom perspective view of a rotating tibial insert for use with the tibial tray of FIGS. 1 and 2.

Looking now to FIGS. 1-4, a prosthetic knee system includes a tibial tray 12 (shown in FIGS. 1 and 2), a fixed tibial insert 14 (shown in FIG. 3), and a rotating tibial insert 16 (shown in FIG. 4). As is discussed in greater detail below, the fixed tibial insert 14 may be combined with the tibial tray 12 to provide a fixed or non-rotating tibial assembly while the rotating tibial insert 16 may be combined with the tibial tray 12 to provide a rotating or mobile knee assembly. In other words, a single tray (i.e., the tibial tray 12) may be used with either the fixed tibial insert 14 or the mobile tibial insert 16. Such a system allows the surgeon to implant the tibial tray 12 within a patient's tibia and then ascertain whether the fixed or mobile tibial insert 14, 16 would be more appropriate for the particular knee replacement at hand. Further, a prosthetic knee system having a single tray for use with both mobile and fixed inserts allows the surgeon to perform a revision surgery to be performed without having to remove the tibial tray from the patient's tibia. In other words, if original total knee arthroplasty (TKA) was performed to implant the rotating insert 16 shown in FIG. 4, a revision surgery to replace the rotating insert 16 with the fixed insert 14 may not require the surgeon to remove the tibial tray 12. Accordingly, such a revision surgery may be less invasive to the patient than a revision surgery requiring the tibial tray to be removed.

Looking now to FIGS. 1 and 2, the tibial tray 12 includes a platform 20 and a stem 22 coupled to a bottom surface 24 of the platform 20. Illustratively, a top surface 26 of the platform 20 is generally planar and, in some embodiments, may be highly polished. A cavity or bore 30 through the platform 20 and into the stem 22 is formed to receive a complimentary stem of a tibial insert, as is discussed below. The platform 20 of the tibial tray 12 includes two protrusions 32 extending inwardly from a sidewall defining the bore 30 formed through the platform 20. Illustratively, the protrusions 32 extend toward each other from across opposite sides of the open end or aperture of the bore 30.

The platform 20 also includes two C-shaped guide tracks 34 which are recessed from top surface 26 of the platform 20. Illustratively, the guide tracks 34 extend between the protrusions 32 as shown best in FIG. 2. Additionally, the platform 20 includes two recesses defined in the sidewall defining the bore 30. Each recess has a substantially "C" shape and is in communication with each corresponding guide track 34 as shown in FIG. 1 and in phantom in FIG. 2.

Looking now to FIG. 3, the fixed or non-rotating insert 14 includes a platform 40 having an upper bearing surface (not shown) configured to mate with the articulating surface of the condyles of a coordinating femoral component (not shown). The fixed insert 14 further includes a connector hub 42 coupled to a bottom surface 44 of the of the platform 40. The connector hub 42 is generally circular in shape and includes two notches 46 formed therein. The notches 46 are illustratively positioned across from each other and are formed to receive the protrusions 32 of the tibial tray 12, as is discussed in greater detail below. The connector hub 42 further includes two flexible locking tabs 48 which may be moved from their normal, extended position to a inward or retracted position.

The rotating insert 16, shown in FIG. 4, includes a platform 50 having a top, bearing surface (not shown) and a stem 52 coupled to a bottom surface 54 of the platform 50. The rotating insert 16 further includes two flanges or rotational guides 56 coupled to the stem 52 and the bottom surface 54 of the platform 50. Illustratively, the guides 56 are curved and are positioned on opposite sides of the stem 52 from each other.

In use, the surgeon may implant the tibial tray 12 within the patient's tibia and may then make a determination as to whether the non-rotating insert 14 or the rotating insert 16 should be used for the particular TKA being performed. In situations where the non-rotating insert 14 is desired, the connector hub 42 is received within the bore 30 of the tibial tray 12 such that the bottom surface 44 of the non-rotating insert 14 is adjacent to and in contact with the top surface 26 of the tibial tray 12. The protrusions 32 of the tibial tray 12 are received within the notches 46 of the non-rotating insert 14 in order to prevent rotational motion of the non-rotating insert 14 relative to the tibial tray 12. The locking tabs 48 of the fixed insert 14 are received within the recesses 36 of the tibial tray 12 in order to further prevent relative movement between the bearing 14 and the tray 12. The locking tabs 48 also aide in preventing "lift-off" or axial motion of the insert 14 in a direction away from the tray 12. Illustratively, the tibial tray 12 and the fixed bearing 14 cooperate to provide a fixed tibial assembly.

In situations where the mobile or rotating insert 16 is desired, the rotational guides 56 of the bearing 16 are received on the respective guide tracks 34 of the tibial tray 12 while the stem 52 of the insert 16 is received within the bore 30 of the tray 12. The insert 16 is able to rotate about a longitudinal axis running through the center of the stems 22, 52 of each component. The protrusions 32 of the tibial tray 12 operate as rotational stops to limit the rotational movement of the rotating insert 16 relative to the tibial tray 12. For example, as the rotating insert 16 rotates either clockwise or counterclockwise, the rotational guides 56 of the insert 16 will engage the protrusions 32 of the tibial tray 12 to prevent further movement in that particular direction. Illustratively, the arc length of each rotational guide 56 is generally smaller than the arc length of the guide track 34 within which each guide 56 is positioned. The arc length of the rotational guides 56 may be adjusted to increase or decrease the amount of rotational movement of the insert 16 relative to the tray 12. For example, in one particular embodiment, the arc length of the rotational guides 56 is about 10 degrees to about 40 degrees. Illustratively, the tibial tray 12 and the rotating insert 16 cooperate to provide a rotating tibial assembly.

Figure 5:
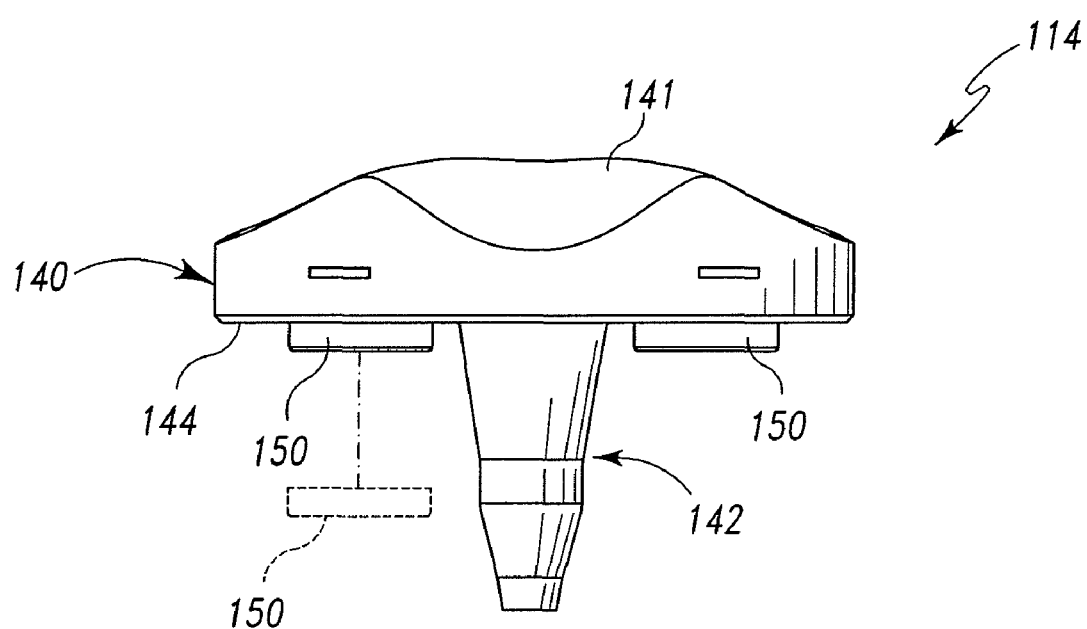
FIG. 5 is a side view of a tibial insert having removable tabs.
Figure 6:
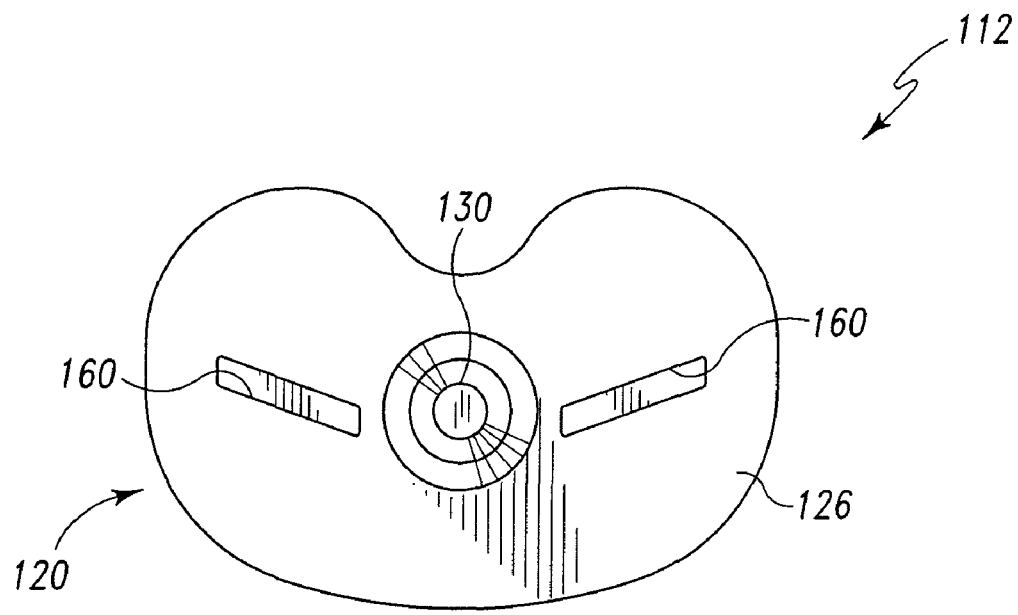
FIG. 6 is a top view of a tibial tray configured to be coupled with the tibial insert of FIG. 5.

Looking now to FIGS. 5 and 6, a tibial tray 112, as shown in FIG. 6, and a tibial insert 114, as shown in FIG. 5, cooperate to provide a prosthetic knee system which may be arranged to provide a rotating tibial assembly and a fixed or non-rotating tibial assembly, as is discussed in greater detail below. The tibial insert 114 includes a platform 140 having an upper bearing surface 141 and a stem 142 coupled to a bottom surface 144 of the platform 140. The tibial insert 114 further includes first and second removable tabs 150 which may be coupled to the bottom surface 144 of the platform 140 or which may be removed from the bottom surface 144 of the platform 140. The tabs 150 may be snapped, screwed, press-fit or otherwise coupled to the bottom surface 144 such that the tabs 150 may also be generally easily removed from the platform 140 as desired.

The tibial tray 112, shown in FIG. 6, includes a platform 120, a stem 122, and a bore 130 formed through the platform 120 and into the stem 122. Illustratively, a pair of slots 160 are formed in a top surface 126 of the platform 120. The slots 160 correspond in size, shape, and location to the removable tabs 150 of the tibial insert 114. As such, the tibial insert 114 may be used as a fixed tibial insert when the tabs 150 are coupled to the platform 120 of the tibial insert 114. In such a configuration, the tabs 150 are each received within a respective one of the slots 160 of the tibial tray 112 in order to prevent rotation of the tibial insert 114 relative to the tray 112.

However, the tibial insert 114 may also be used as a rotating tibial insert when the tabs 150 are removed from the platform 140 of the tibial insert 114. In this configuration, the tibial insert 114 is able to rotate freely relative to the tibial tray 112 about a longitudinal axis through the stem 122 of the tibial tray 112. Accordingly, the tibial tray 112 and the tibial insert 114 shown in FIGS. 5 and 6 may be configured to provide either a rotating tibial assembly or a fixed bearing assembly, as desired. Further, illustratively, the prosthetic knee system shown in FIGS. 5 and 6 includes only a single tibial tray (i.e., the tibial tray 110) and a single tibial insert (i.e., the tibial insert 112) having a component (i.e., the tabs 130) which may be selectively used to provide either the fixed or mobile bearing assemblies. While the prosthetic knee system of FIGS. 5 and 6 is shown to include tabs removably coupled to the bottom surface of a tibial insert with corresponding slots formed in the top surface of the tibial tray, it is within the scope of this disclosure to include a prosthetic knee system whereby the tabs are removably coupled to the top surface of the tibial tray and the bottom surface of the tibial insert includes slots formed to receive the tabs therein.

Figure 7:
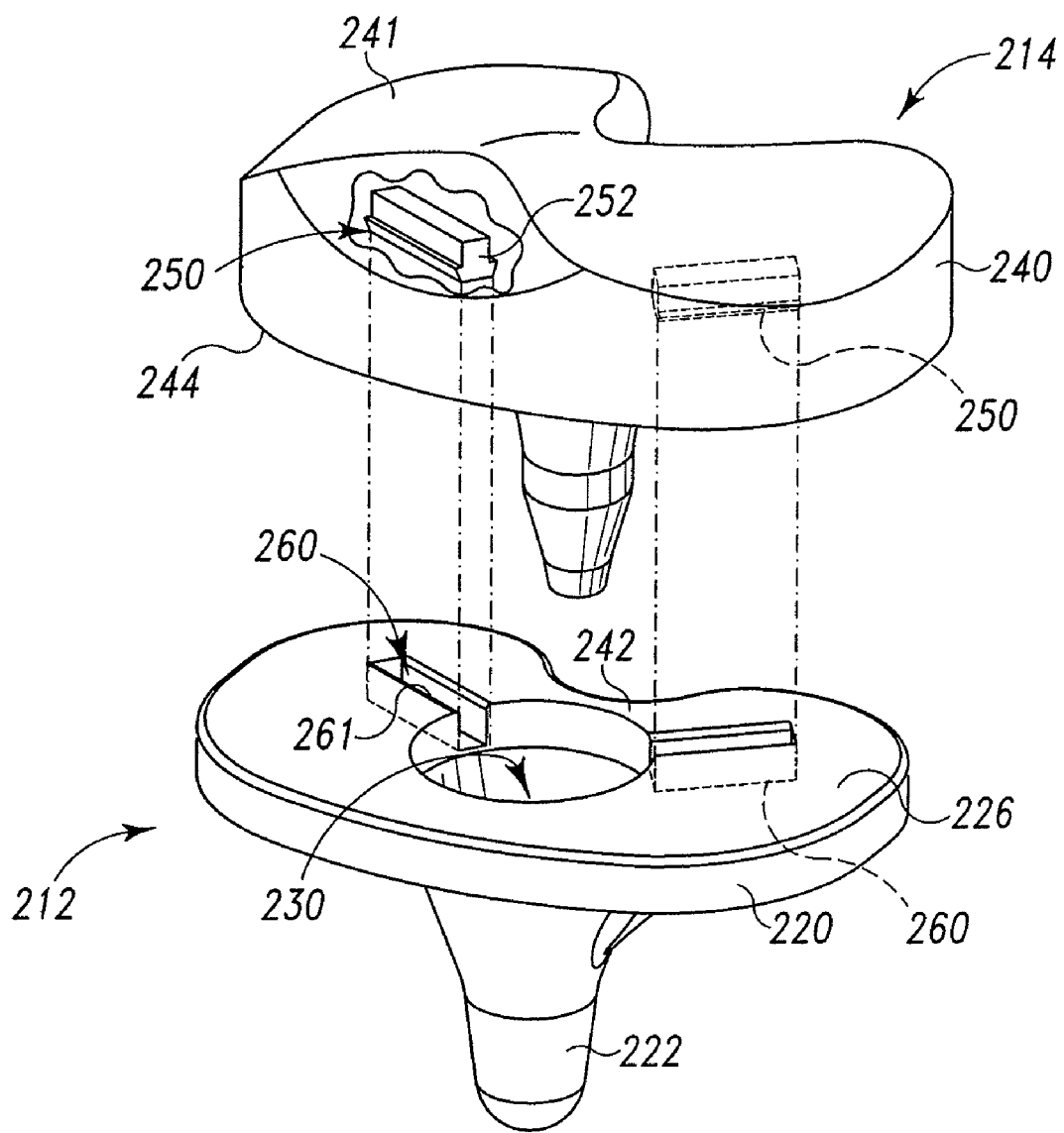
FIG. 7 is a perspective view of a fixed tibial assembly including a tibial tray, a tibial insert, and a locking rail system fixed to the tibial insert.
Figure 8:
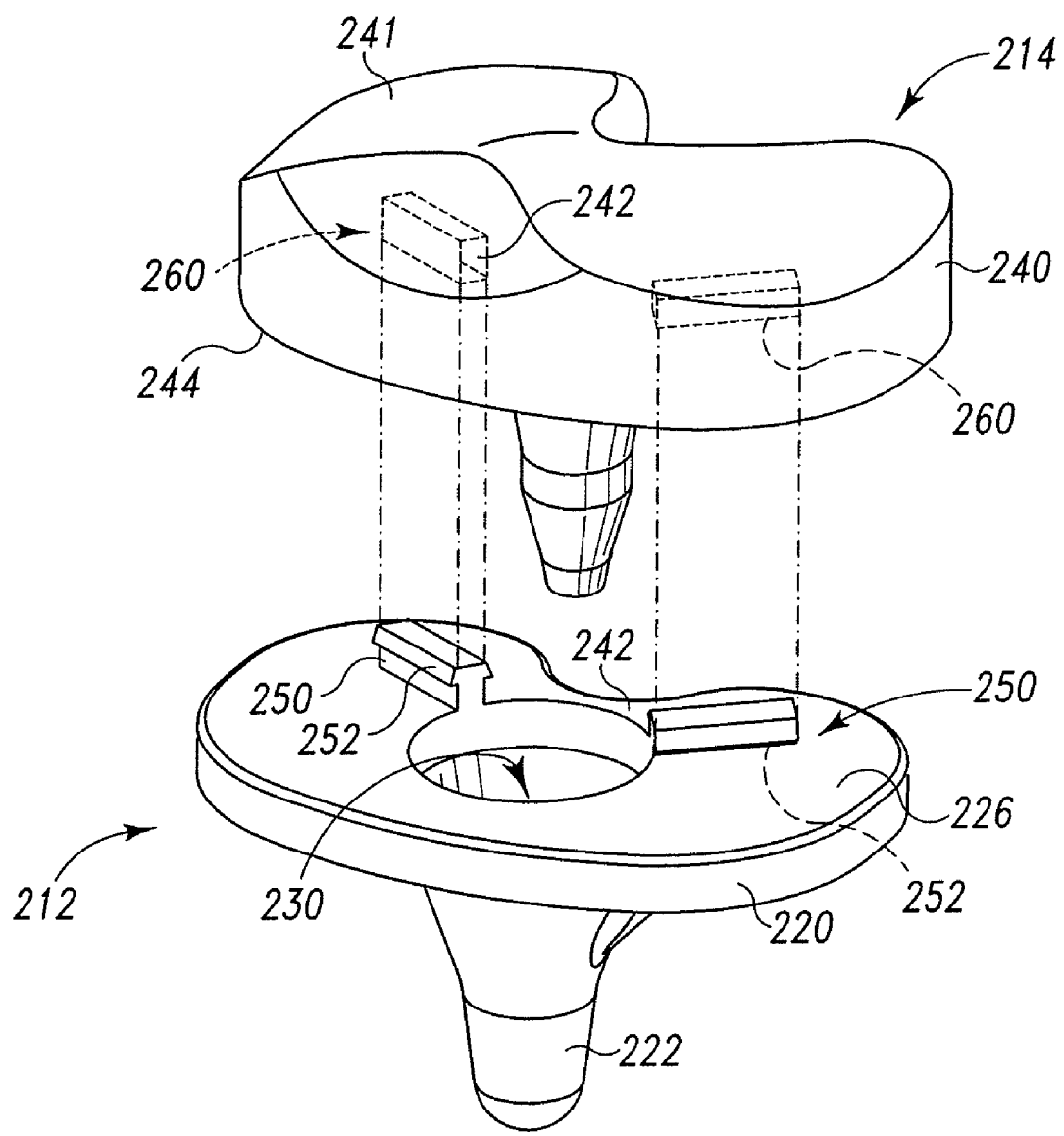
FIG. 8 is a perspective view of a fixed tibial assembly including a tibial tray, a tibial insert, and a locking rail system fixed to the tibial tray.
Figure 9:
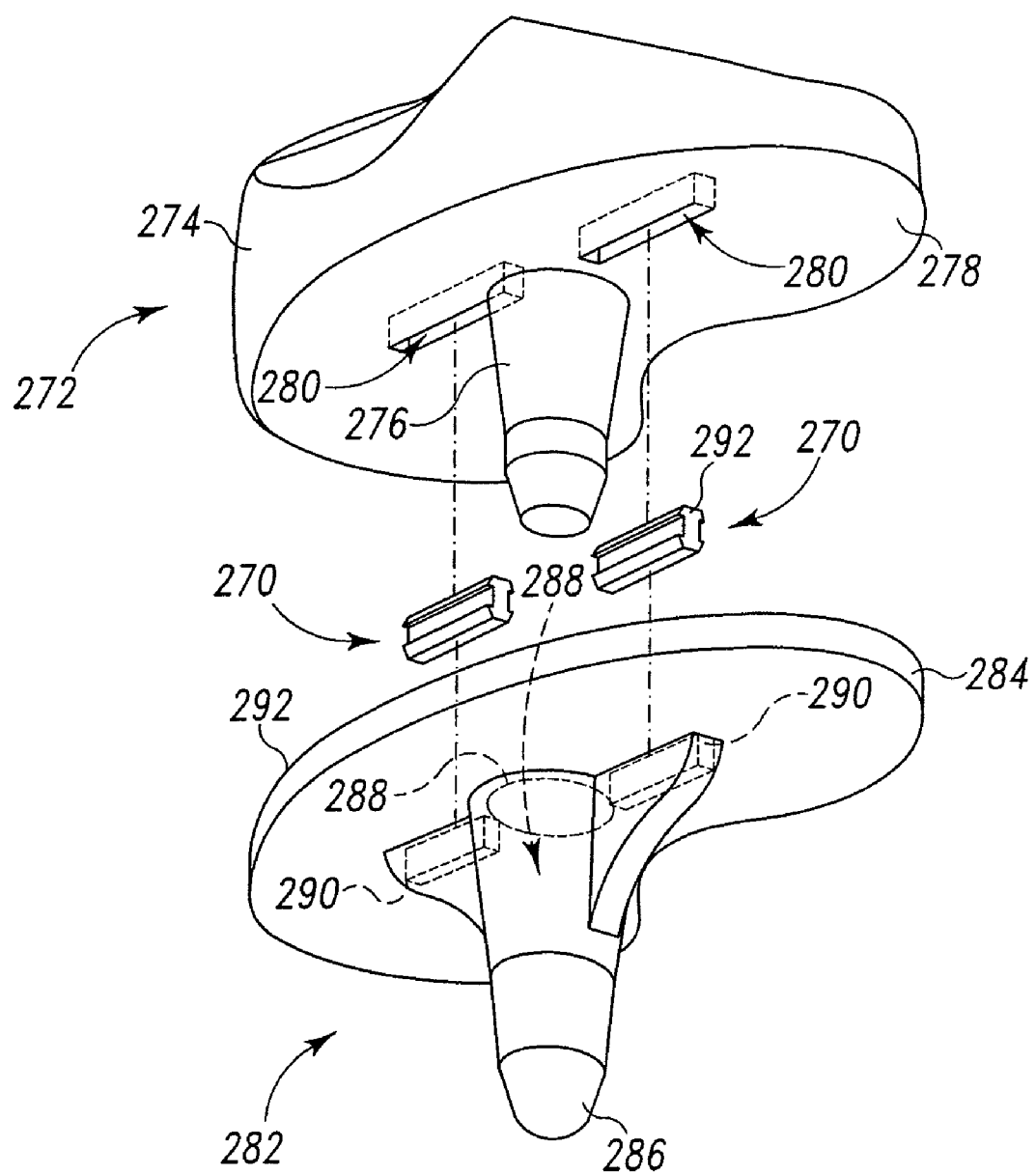
FIG. 9 is a perspective view of a tibial assembly including a tibial tray, a tibial insert, and a removable locking rail system to convert the tibial insert from a rotating tibial insert to a fixed tibial insert.

For example, FIGS. 7-9 show various prosthetic knee systems having fixed as well as removable tabs or rail systems. Looking first to FIG. 7, a tibial tray 212 and a tibial insert 214 cooperate to provide a fixed tibial assembly. The tibial insert 214 includes a platform 240 having an upper bearing surface 241 and a stem 242 coupled to a bottom surface 244 of the platform 240. The tibial insert 214 further includes first and second keys or tabs 250 coupled to the bottom surface 244 of the platform 240. Illustratively, the tabs 250 are generally rectangular in shape and include outwardly-extending flanges 252. The tabs 250 may be made from a polymer and molded with the platform 240 or attached later once the platform 240 has been molded. Alternatively, the tabs 250 may be made of metal and may be compression molded into the polymer platform 240. While the tibial insert 214 includes two fixed tabs 250, it is within the scope of this disclosure to provide any number of fixed rails extending downwardly from any location on the bottom surface 244 of the platform 240 of the tibial insert 214.

The tibial tray 212 includes a platform 220, a stem 222, and a bore 230 formed though the platform 220 and into the stem 222. The tibial tray 212 further includes a pair of slots or tracks 260 formed in a top surface 226 of the platform 220. The slots 260 correspond in size and location to the fixed tabs 250 of the tibial insert 214 are generally elongated and rectangular in shape. However, the slots 260 may be formed to include a cut-out portions (not shown) corresponding to the outwardly-extending flanges 252 of the tabs 250. Illustratively, the slots 260 are defined by curved or rounded outer edges 261. During use, the tabs 250, fixed to the bottom surface 244 of the insert 214, are each received within a respective one of the slots 260 of the tibial tray 212 in order to prevent rotation of the tibial insert 214 relative to the tray 212. The outwardly-extending flanges 252 of the tabs 250 operate to prevent lift-off of the insert 214 away from the tray 212. In order to provide a rotating tibial assembly, a rotating tibial insert (not shown) without keys 250 may be provided for use with the tray 212.

Looking now to FIG. 8, a prosthetic knee system similar to that shown in FIG. 7 is provided. As such, like reference numbers have been used to denote like features. Illustratively, the tibial tray 212 of FIG. 8 includes a pair of slots or tracks 260 formed in the bottom surface 244 of the platform 240 to receive a corresponding pair of tabs or keys 250 fixed to and extending upwardly from the tip surface 226 of the platform 220 of the tibial tray 212. The tabs 250 coupled to the platform 220 may be metal and may be formed integrally with the platform 220 or may be attached to the platform 220 at a later time. During use, the tabs 250 fixed to the top surface 226 of the tray 212 are each received within a respective one of the slots 260 of the tibial insert 214 in order to prevent rotation of the tibial insert 214 relative to the tray 212. As shown in FIGS. 7 and 8, the locking tabs 250 may be coupled to either the tray 212 or the insert 214 while the corresponding slots 260 may be formed in the other of the tray 212 or the insert 214. A separate tray (not shown) without the keys 250 may be provided for use with the insert 212 shown in FIG. 8 in order to provide a rotating knee assembly.

Looking now to FIG. 9, a prosthetic knee system similar to that shown in FIGS. 4 and 5 and showing removable tabs or rails 270 is provided in order to convert the knee system from a rotating tibial assembly to a fixed tibial assembly, as is discussed below. Illustratively, a tibial insert 272 includes a platform 274 having an upper bearing surface (not shown) and a stem 276 coupled to a bottom surface 278. A pair of slots or tracks 280 are formed in the bottom surface 278 of the platform 274. Illustratively each slot 280 is elongated and generally rectangular in shape. A tibial tray 282 of the system includes a platform 284, a stem 286, and a cavity or bore 288 formed through the platform 284 and into the stem 286 to receive the stem 276 of the insert 272 therein. Illustratively, a pair of slots or tracks 290 are formed in a top surface 292 of the platform 284. The slots 290 of the tray 282 correspond in size, shape, and location to the slots 280 of the insert 272. The knee system further includes a pair of locking tabs 270 which may each be inserted into one of the slots 280 of the insert 272 and a corresponding slot 290 of the tray 282 in order to prevent rotation of the tibial insert 272 relative to the tray 282. Each locking tab 270 includes upper and lower outwardly-extending flanges 293 to be snapped or press-fit into a respective slot 280 or 290 of the corresponding insert 272 and tray 282. Illustratively, the locking tabs 270 may be made from metal or a polymer. Accordingly, the tibial insert 272 may be used as a fixed tibial insert when the locking keys 270 are inserted into the slots 280, 290 of the tibial insert 272 and the tibial tray 282 and may also be used as a rotating tibial insert when the locking rails 270 are removed.

It should be appreciated that in some embodiments, the tab-and-slot configuration of the embodiments of FIGS. 5-9 may be incorporated with the embodiment of FIGS. 1-4 to provide a more rigid coupling of the tibial insert 14 to the tibial tray 12. For example, one or more of the tabs 150, 250, 270 may be coupled to or integral with the bottom surface 44 of the tibial insert 14 and received in one or more slots defined in the top surface 26 of the tibial tray 12.

Looking now to FIGS. 10-13, yet another prosthetic knee system including non-rotating and rotating tibial assemblies is provided. The prosthetic knee system includes a tibial tray 312, a fixed or non-rotating tibial insert 314 (shown in FIGS. 10 and 11), and a rotating tibial insert 316 (shown in FIGS. 12 and 13). Illustratively, the tibial tray 312 and the non-rotating insert 314 cooperate to provide a fixed tibial assembly while the tibial tray 312 and the rotating insert 316 cooperate to provide a rotating tibial assembly.

The tibial tray 312 includes a platform 320 and a stem 322 coupled to the bottom surface 324 of the platform 320. The platform 320 includes a center stepped section to define an upper platform 340 and a lower platform 342. The lower platform 342 is larger than the upper platform 340 to define an outer ledge 344 of the platform 320.

Looking now to FIGS. 10 and 11, the fixed tibial insert 314 includes an upper bearing surface 315, a bottom surface 346, and a recess or cavity 348 formed in the bottom surface 346 and sized to receive the upper platform 340 of the tibial tray 312 therein. In such a position, the bottom surface 346 of the tibial insert 314 is configured to engage the ledge 344 of the lower platform 342 of the tray 312. As such, when the upper platform 340 of the tibial tray 312 is received within the recess 348 of the non-rotating tibial insert 314, the insert 314 is prevented from rotating relative to the tray 312. As shown in FIGS. 10 and 11, the tibial insert 314 is sized such that an outer perimeter of the lower platform 342 of the tibial tray 312 is generally the same size as an outer perimeter of the tibial insert 314. However, in some embodiments, the outer perimeter of the lower platform 342 of the tibial tray 312 may be slightly larger than the size of the outer perimeter of the tibial insert 314 to provide greater surface area for supporting the tibial insert 314 such that the tibial tray 312 can accommodate tibial inserts of varying sizes.

Figure 13:
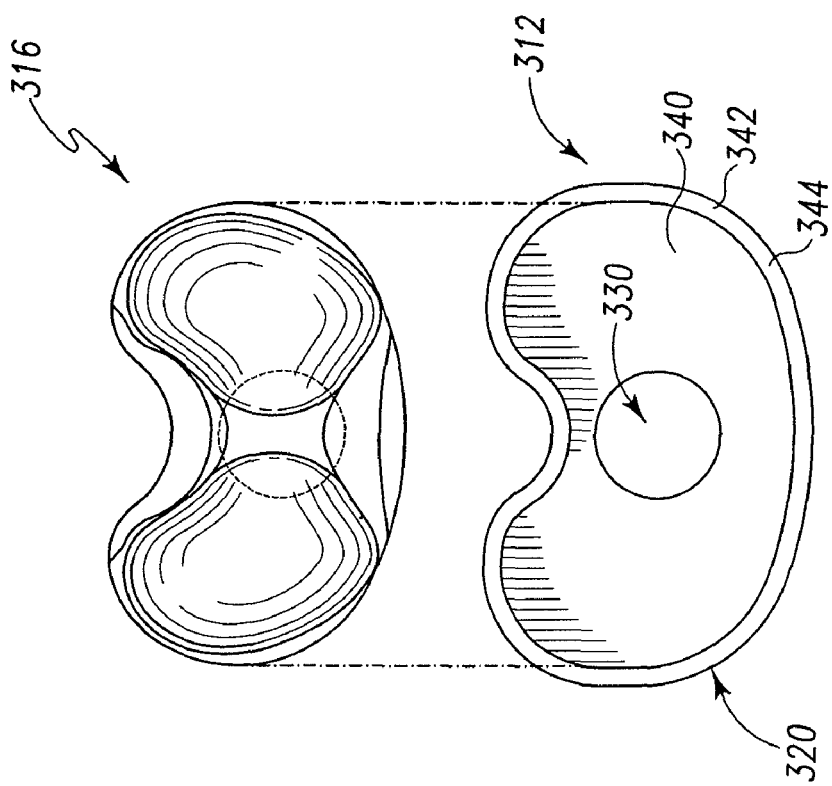
FIG. 13 is a top view of the tibial tray and the tibial insert of FIG. 12.
Figure 12:
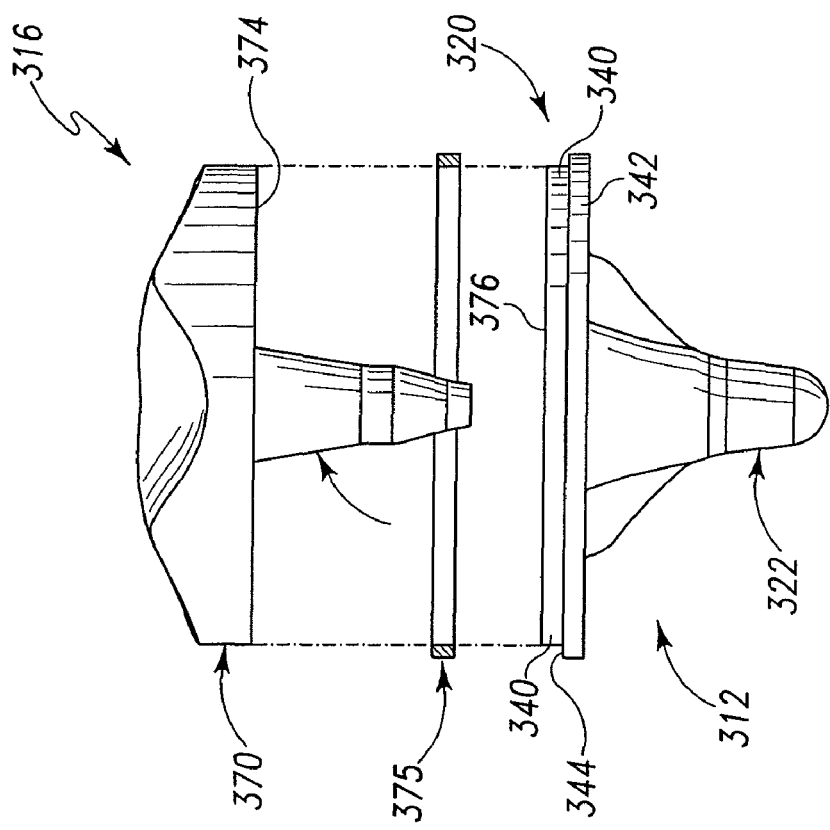
FIG. 12 a side view of the tibial tray of FIGS. 10 and 11 and a rotating tibial insert configured to be coupled with the tibial tray.

Looking now to FIGS. 12 and 13, the rotating tibial insert 316 includes a platform 370 and a stem 372 coupled to the bottom surface 374 of the platform 370 and configured to be received within a bore 330 of the tibial tray 312. Illustratively, the rotating tibial insert 316 is sized such that an outer perimeter of the bottom surface 374 of the platform 370 is generally the same size as the outer perimeter of upper platform 340 of the tibial tray 312 and is configured to rest on an upper surface 376 of the upper platform 340 of the tray 312 for rotation relative to the tray 312. A metal ring 375 may be provided for use with the rotating tibial insert 316. Illustratively, the metal ring 375 may be configured for placement around the upper platform 340 of the tibial tray 312 in order to surround the upper platform 340 in order to further support any unsupported portions of the polymer platform 370 of the rotating tibial insert 316 to prevent any possible cold flow of the polymer platform 370 during use. Illustratively, the metal ring 375 may be rigidly fixed to the tibial tray 312 to prevent any metal-on-metal movement between the ring 375 and the tray 312. As such, the metal ring 375 may include flexible tabs (not shown) configured to be received within undercut portions of the upper and/or lower platform portions 340, 342 of the tibial tray 312.

Figure 14:
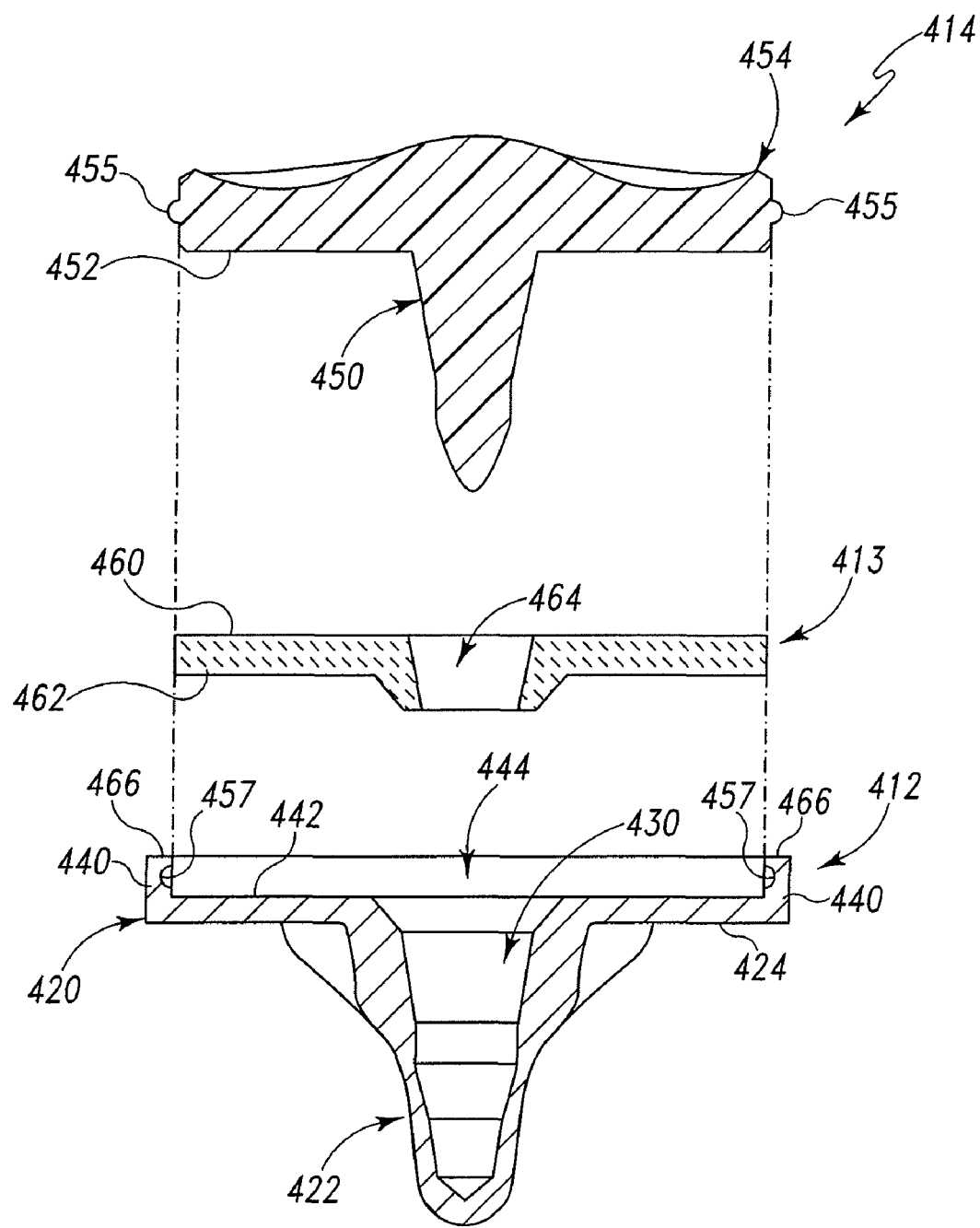
FIG. 14 is a sectional view of a prosthetic knee system including a tibial tray, a tibial spacer, and a tibial insert.

Looking now to FIG. 14, another prosthetic knee system is provided which includes a tibial tray 412, a tibial insert 414, and a spacer 413. Illustratively, the tray 412 and the tibial insert 414 cooperate to provide a non-rotating tibial assembly while the tray 412, the spacer 413, and the insert 414 cooperate to provide a rotating tibial assembly. The tibial tray 412 includes a platform 420 and a stem 422 coupled to a bottom surface 424 of the platform 420. A bore 430 of the tray 412 is formed through the platform 420 and into the stem 422. The platform 420 of the tray 412 includes an outer rim 440 extending upwardly from an upper surface 442 of the platform 420. The outer rim 440 extends around the periphery of the platform 420 and cooperates with the upper surface 442 of the platform 420 to define a cavity 444 therein.

In a first or fixed configuration, a stem 450 of the tibial insert 414 is received within the bore 430 of the tibial tray 412 such that a bottom surface 452 of the tibial insert 414 is adjacent to and engaged with the upper surface 442 of the platform 420 of the tibial tray 412. As such, the outer rim 440 of the tibial tray 412 surrounds a portion of the platform 454 of the tibial insert 414 in order to prevent rotation of the tibial insert 414 relative to the tibial tray 412. Illustratively, the platform 454 of the tibial insert 414 may include one or more locking tabs 455 to be received within grooves or slots 457 formed in the outer rim 440 of the tray 412 in order to further fix the tibial insert 414 relative to the tray 412.

In a second, or rotating configuration, the spacer 413 is placed within the cavity 444 of the tibial tray 412 and the insert 414 is placed onto the spacer 413. As shown in FIG. 14, the spacer 413 includes an upper surface 460, a lower surface 462, and an aperture 464 formed therethrough. In the rotating configuration, the lower surface 462 of the spacer 413 is adjacent to and engaged with the upper surface 442 of the platform 420 of the tibial tray 412. Further, the upper surface 460 of the spacer 413 is generally aligned or flush with an upper surface 466 of the outer rim 440 of the tibial tray 412. The stem 450 of the tibial insert 414 is received through the aperture 464 of the spacer 413 and into the bore 430 of the tibial tray 412 such that the bottom surface 452 of the tibial insert 414 is adjacent to and engaged with the upper surface 460 of the spacer 413.

In the second configuration, the tibial insert 414 is able to rotate relative to both the tibial tray 412 and the spacer 413. The spacer 413 remains generally stationary relative to the tibial tray 412. As such, the tibial tray 412 and the tibial insert 414 shown in FIG. 14 cooperate to define a non-rotating tibial assembly while the tibial tray 412, the tibial insert 414, and the spacer 413 cooperate to define a rotating tibial assembly.

Figure 15:
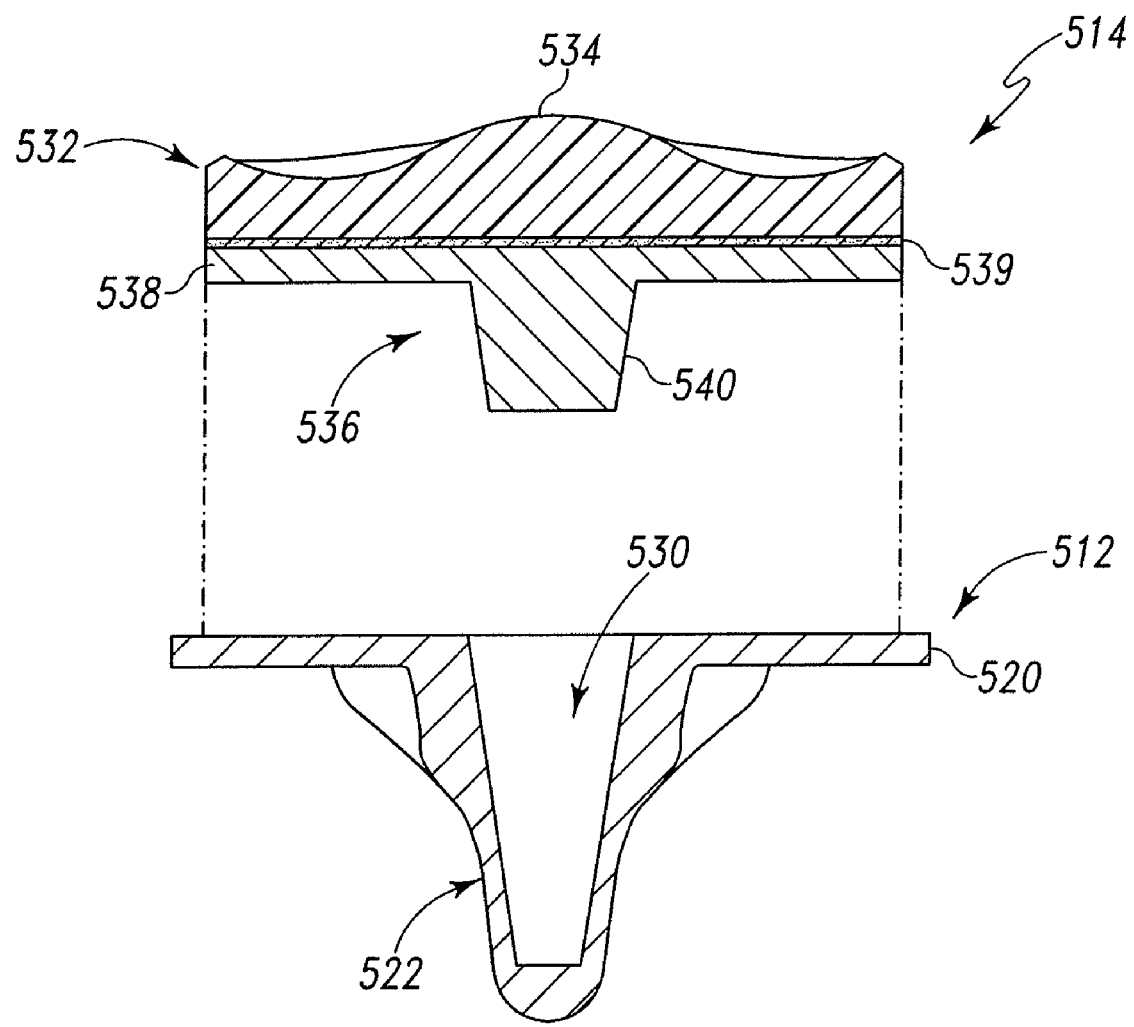
FIG. 15 is a sectional view of a tibial tray and a non-rotating tibial insert including a metal base having a tapered stem configured to be coupled with the tibial tray.

Looking now to FIG. 15, another knee prosthesis system is provided. The knee prosthesis system includes a tibial tray 512 and a fixed tibial insert 514. A rotating tibial insert (not shown) similar to the tibial insert 414 provided in FIG. 14 may also be included in this knee prosthesis system. As with many of the other tibial trays disclosed herein, the tibial tray 512 shown in FIG. 15 includes a stem 522, a platform 520, and a cavity or bore 530 formed to receive a portion of the tibial insert 514 therein. The fixed tibial insert 514 includes a bearing 532 defining an upper bearing surface 534. Illustratively, the bearing 532 is made of a polymer such as ultra high molecular weight polyethylene (UHMWPE), for example. The fixed tibial insert 514 further includes a base or base plate 536 coupled to the bearing portion 532. Illustratively, the base 536 includes a backing 538 coupled to the bearing 532 and a stem 540 coupled to the backing 538. Illustratively, the base 536 is made from a metal such as titanium or cobalt chromium, for example. As shown in FIG. 15, a macro-texturized layer 539 of the stem portion 536, such as Porocoat® porous coating, for example, provides a surface into which the UHMWPE bearing 532 may be compression molded. The macro-texturized layer 539 operates to provide a physical interlock between the bearing 532 and the metal base 536. Alternatively, a bonding agent may be used to adhere the bearing component 532 to the metal base 536. Such techniques are discussed within U.S. Patent Application Publication No. US 2006/0155383, titled ORTHOPAEDIC BEARING AND METHOD FOR MAKING THE SAME, the disclosure of which is hereby incorporated by reference herein.

The stem 540 of the base 536 as well as the bore 530 of the tibial tray 512 are each provided with coordinating metal-to-metal Morse tapers in order to lock the two components together in a fixed relationship. In other words, when the stem 540 of the fixed tibial insert 514 is press-fit into the bore 530 of the tibial tray 512, the Morse taper of the bore 530 and stem 540 operate to prevent relative movement between the insert 514 and the tray 512 to prevent rotating movement of the insert 514 relative to the tray 512. The metal base 536 of the fixed tibial insert 514 may also prevent "cold flow" of the insert 514 into the bore 530 of the tray 512. Further, it is contemplated that the metal base 536 may operate to provide stiffness to the UHMWPE bearing 532 including the bearing surface 534 in order to minimize stress on the tibial insert 514.

A separate all-poly tibial insert (not shown), such as the tibial insert 414 shown in FIG. 14, may be used with the tray 512 of FIG. 15 in order to provide a rotating tibial assembly.

Figure 16:
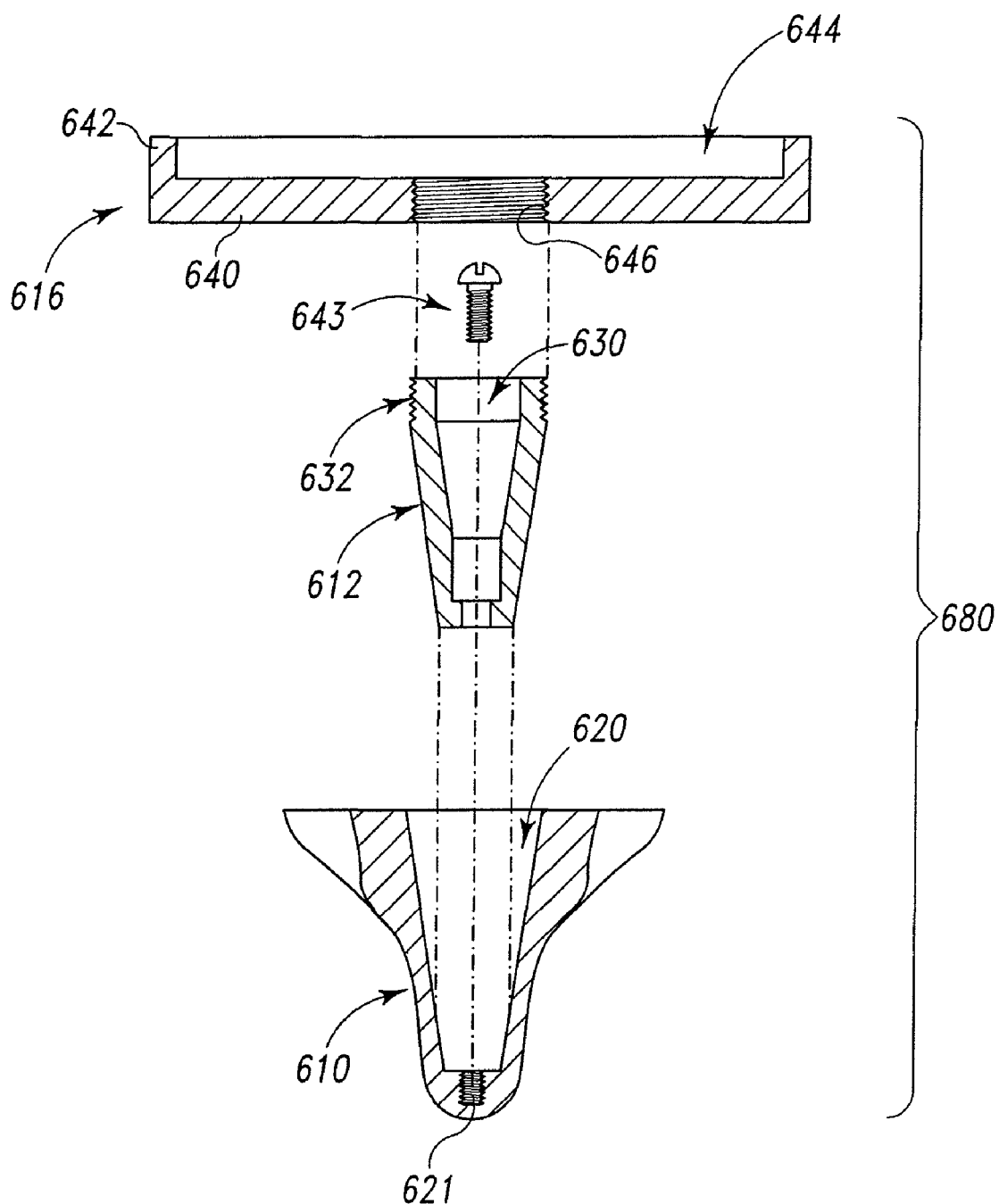
FIG. 16 is a sectional view of a modular tibial tray for use with a non-rotating tibial insert.
Figure 17:
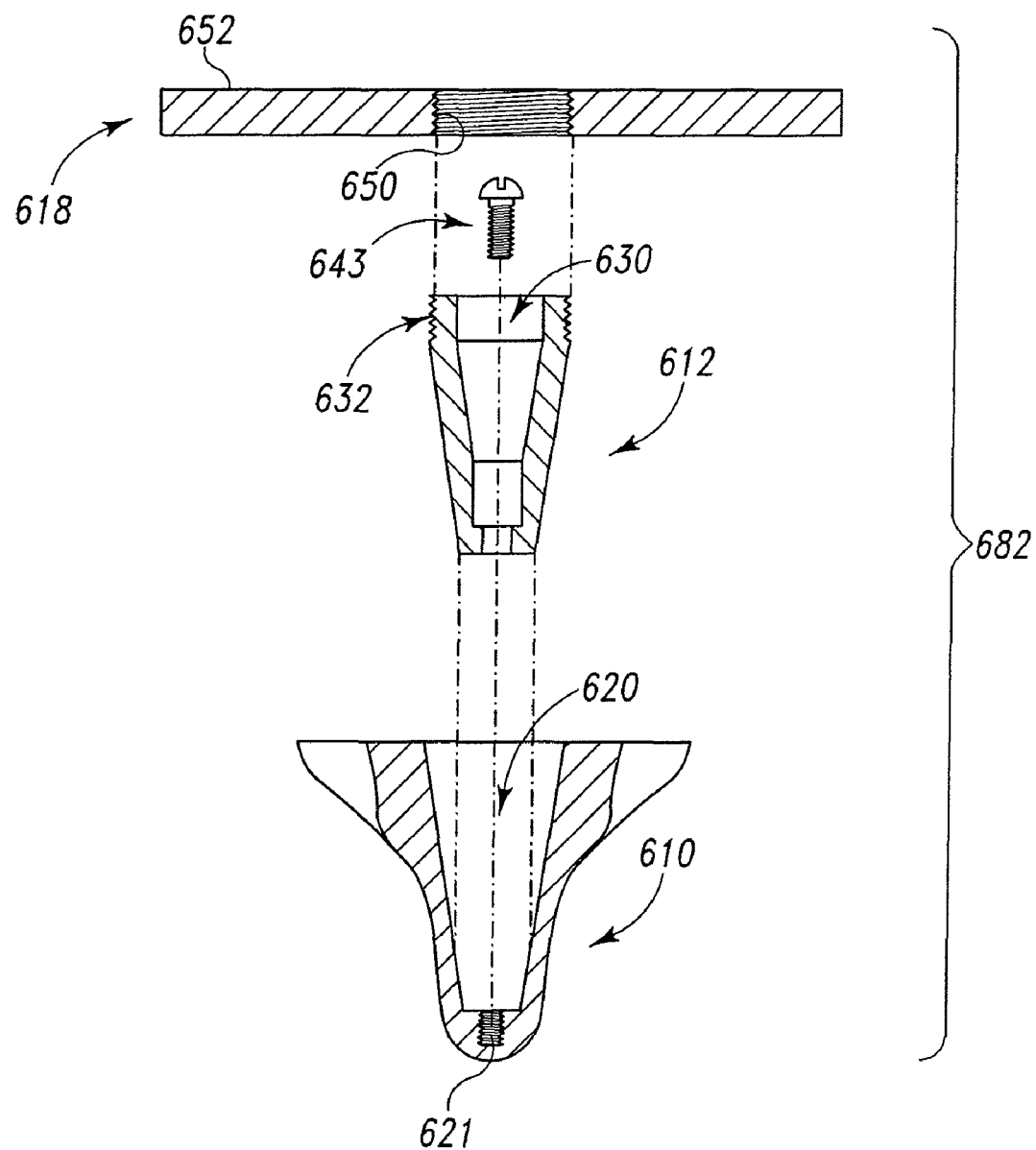
FIG. 17 is a sectional view of another modular tibial tray for use with a rotating tibial insert.

Looking now to FIGS. 16 and 17, another knee prosthesis system is provided. The knee prosthesis system includes a modular tibia tray for use with a tibial insert (not shown), such as the tibial insert shown in FIG. 14, for example, which may be configured as a fixed tray (see FIG. 16) whereby the tibial insert is prevented from rotating relative to the fixed tray or as a mobile tray (see FIG. 17) whereby the tibial insert is able to rotate relative to the rotating tray.

The modular tibial tray includes a stem or keel portion 610 a hub portion 612, a non-rotating platform 616 (shown in FIG. 16) and a rotating platform 618 (shown in FIG. 17). A threaded screw 643 is also provided in order to couple the hub portion 612 and the stem portion 610 together. The stem portion 610 includes a bore 620 configured to receive the hub portion 612 therein. The hub portion 612 may be press-fit into the bore 620 of the stem portion 610. Illustratively, the screw 643 may be received into and partially through the bore 630 of the hub portion to be threaded into a recessed bore 621 of the stem portion 610. The hub portion 612 includes a bore 630 configured to receive the stem of a tibial insert (not shown) therein. The hub portion 612 further includes a threaded neck 632, as shown in FIGS. 16 and 17.

The fixed platform 616 shown in FIG. 16 includes a bottom wall 640 and an outer rim 642 extending upwardly from the bottom wall 640 around the periphery of the bottom wall 640 to define a cavity 644 therein. A threaded aperture 646 is formed through the bottom wall 640 of the fixed platform 616. When the non-rotating tibial tray is assembled, the hub portion 612 is press-fit into the bore 630 of the stem portion 612 and/or coupled to the stem portion by the screw 643 while the platform 616 is threaded onto the neck 632 of the hub portion 612. As such, the stem of the tibial insert (not shown) is received into the bore 630 of the hub portion 612 such that the bottom surface of the platform of the tibial insert is adjacent to and engaged with the upper surface of the bottom wall 640 of the fixed platform 616. At least a portion of the platform of the tibial insert is received within the cavity 644 of the fixed platform 616 in order to prevent rotation of the tibial insert relative to the fixed platform 616.

Looking now to FIG. 17, the modular tibial tray further includes the rotating platform 618 configured for use with a tibial insert, such as the tibial insert shown in FIG. 14, for example. The rotating platform 618 includes a threaded aperture 650 configured to receive the threaded neck 632 of the hub portion 612 in order to coupled the hub portion 612 with the rotating platform 618. In this configuration, the stem of a tibial insert is received through the aperture 650 of the rotating platform 618 and into the bore 630 of the hub portion 612. A bottom surface of the tibial insert is positioned adjacent to and engaged with a top surface 652 of the rotating platform 618 such that the tibial insert is able to rotate relative to the rotating platform 618.

Therefore, a fixed tibial assembly includes the fixed tibial tray 680 shown in FIG. 16 as well as a tibial insert, such as the tibial insert shown in FIG. 14, for example. Alternatively, a rotating tibial assembly of the prosthetic knee system shown in FIGS. 16 and 17 includes a rotating tibial tray 682 shown in FIG. 17 as well as a coordinating tibial insert, such as the tibial insert shown in FIG. 14, for example.

Figure 18:
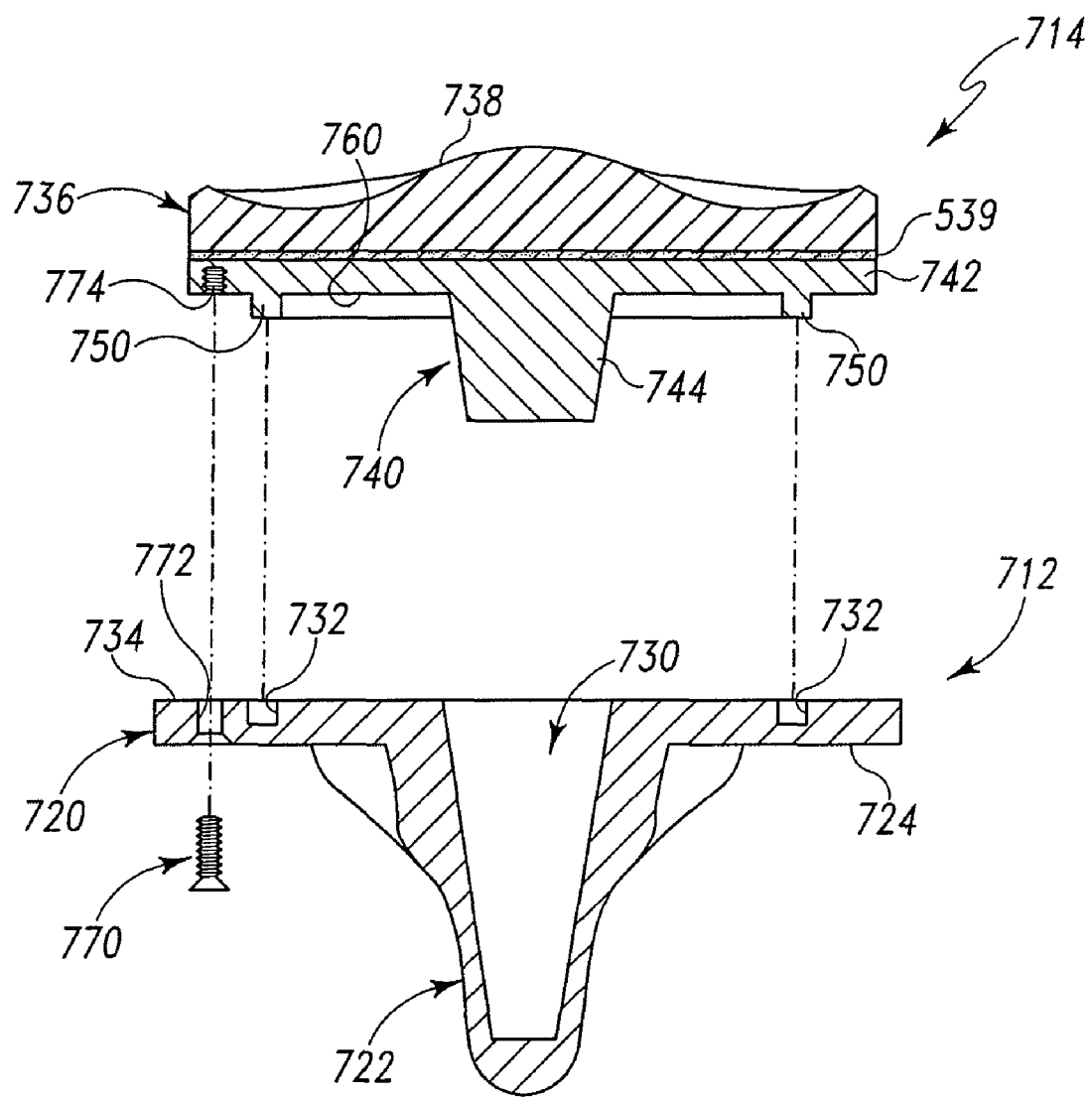
FIG. 18 is a sectional view of a tibial tray and a tibial insert configured to be coupled to the tray.
Figure 19:
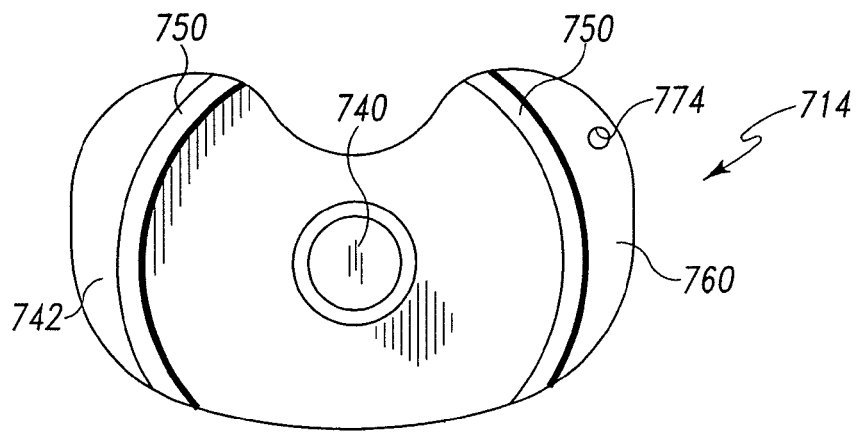
FIG. 19 a bottom view of the rotating tibial insert of FIG. 18 including two curved rails.
Figure 20:
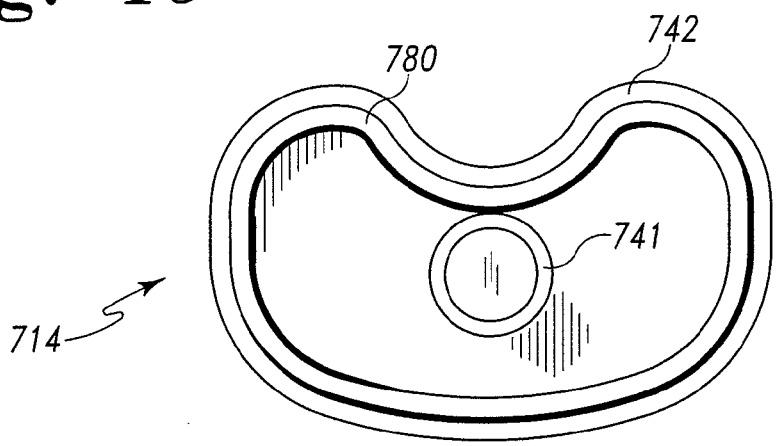
FIG. 20 is a bottom view of an alternative tibial insert for use with the tibial tray of FIG. 18 including a rail extending around a perimeter of the platform of the tibial insert.
Figure 21:
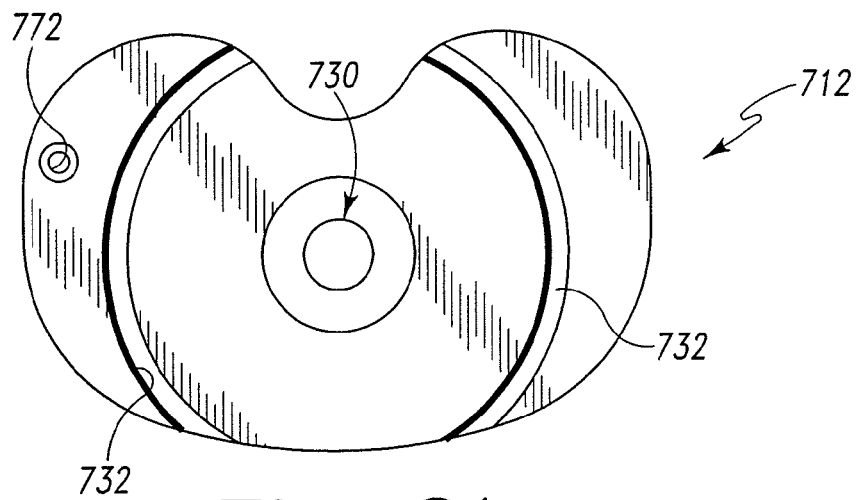
FIG. 21 is a top view of the tibial tray of FIG. 18 including two guide tracks formed therein.

Looking now to FIGS. 18-21, a prosthetic knee system includes a tibial tray 712 and a tibial insert 714. The tibial tray 712 includes a platform 720, a stem 722 coupled to the bottom surface 724 of the platform 720 and a bore 730 configured to receive a stem of the tibial insert 714 therein. The platform 720 includes a track defining grooves 732 formed in the upper surface 734 of the platform 720, as shown in FIGS. 18 and 21, for example. Similar to the tibial insert 514 shown in FIG. 15, the tibial insert 714 includes a bearing portion 736 defining an upper bearing surface 738 and a stem portion 720 coupled to the bearing portion 736. Illustratively, the bearing portion 736 is made of a polymer such as UHMWPE, for example. The stem portion 740 includes a backing 742 coupled to the bearing portion 736 and a stem 744 coupled to the backing 742. Illustratively, the stem portion 740 is made from a metal such as titanium or cobalt chromium, for example. The stem portion 740 further includes two curved rails 750 coupled to the bottom surface of the backing 742 of the stem portion 740, as shown in FIGS. 18 and 19, for example.

In use, the stem 744 of the tibial insert 714 is received within the bore 730 of the tibial tray 712 and the rails 750 are each received within the corresponding grooves or tracks 732 formed in the platform 720 of the tibial tray 712 such that the bottom surface 760 of the platform 742 of the tibial insert 714 is adjacent to and engaged with the upper surface of the platform 720 of the tibial tray 712. In this configuration, the tibial insert 714 is able to rotate relative to the tibial tray 712 about a longitudinal axis through the stem 722 of the tibial tray 712. The rails 750 and the tracks 732 operate to guide and constrain such rotational movement of the insert 714 relative to the tray 712. In order to fix the tibial insert 714 relative to the tibial tray 712, a threaded screw 770 may be inserted through a countersunk bore 772 through the platform 720 of the tibial tray 712 and into a threaded bore 774 formed in the bottom surface 760 of the platform 742 of the tibial insert 714. As such, the tibial insert 714, the tibial tray 712, and the locking screw 770 cooperate to provide a non-rotating tibial assembly while the tibial insert 714 and the tibial tray 712 cooperate to provide a rotating tibial assembly, as discussed above. As shown in FIG. 20, an alternative rail 780 of the tibial insert 714 provides a closed path around a perimeter of the platform 742. This alternative rail 780 is provided for use with an alternative tibial tray to provide a fixed tibial assembly without the use of any threaded screw 770, as is discussed below in regards to FIG. 87.

As noted above, the stem portion 740 of the tibial insert 714 is made from metal such that the rail(s) 750 or 780 of the stem portion 740 is/are made from metal as well in order to slide within the corresponding metal tracks 732 of the tibial tray 712. Alternatively, the metal rail(s) 750 or 780 may be molded directly into the bottom surface of the polymer bearing portion 736 of the insert 714 without the use of the metal backing 742 of the stem portion 740.

Figure 86:
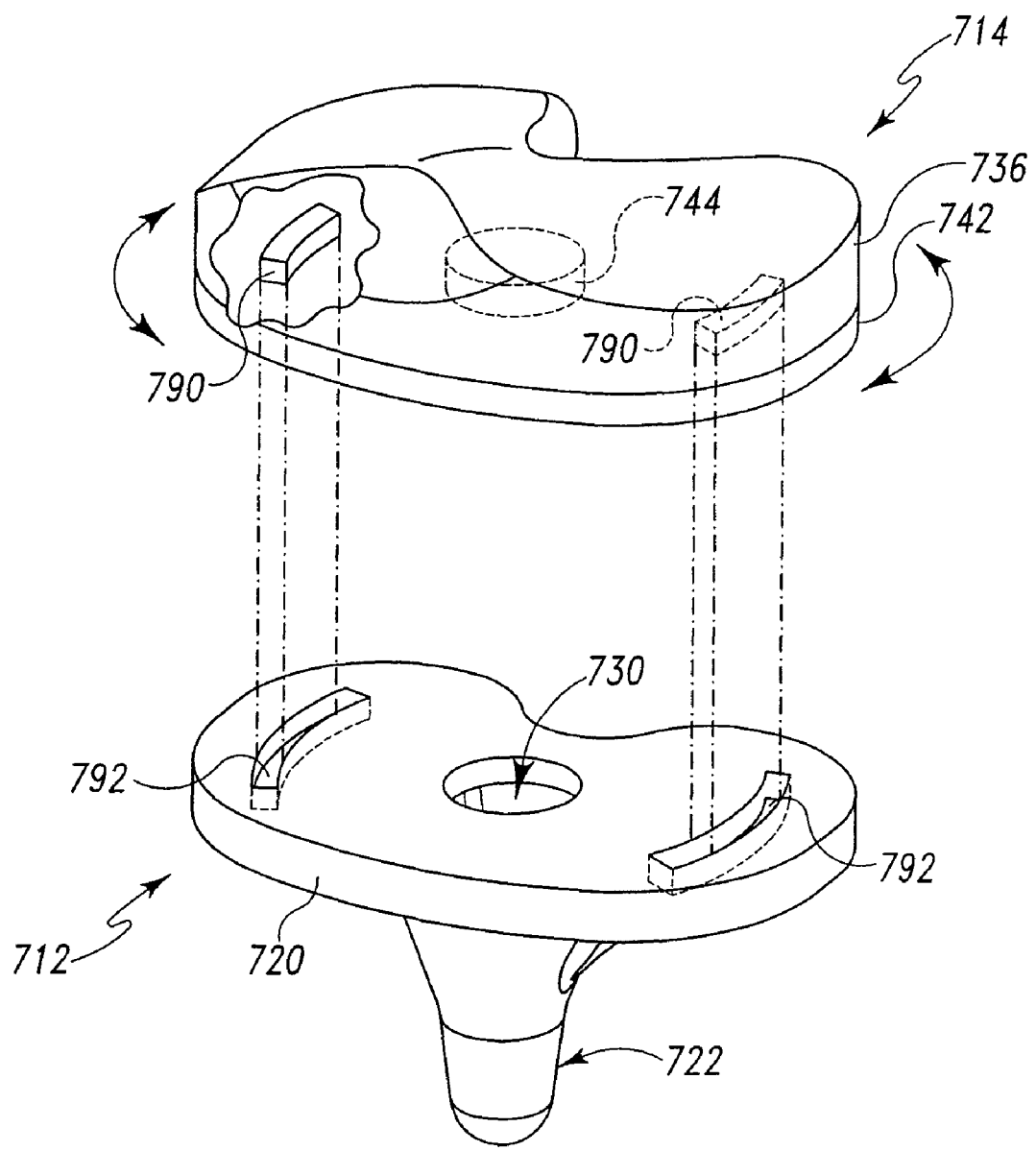
FIG. 86 is a perspective view of a rotating tibial assembly including a track system to guide the rotating movement of the tibial insert relative to the tibial tray.

Looking now to FIG. 86, alternative rails or tabs 790 of the tibial insert 714 and alternative tracks or grooves 792 of the tibial tray 712 are provided. Similar to the rails 750 and corresponding grooves 732 described above in regards to FIGS. 18, 19, and 21, the tabs 790 and tracks 792 operate to guide and constrain rotational movement of the insert 714 relative to the tray 721. Further, similar to that shown in FIG. 18, a locking screw 770 may be provided to fix the relative movement between the tibial insert 712 and the tray 714. Alternatively, the tabs 790 may have a tab or projection (not shown) to be received within an undercut feature (not shown) of the corresponding tracks 792 in order to prevent lift-off of the tibial insert 712 relative to the tray 714.

Figure 87:
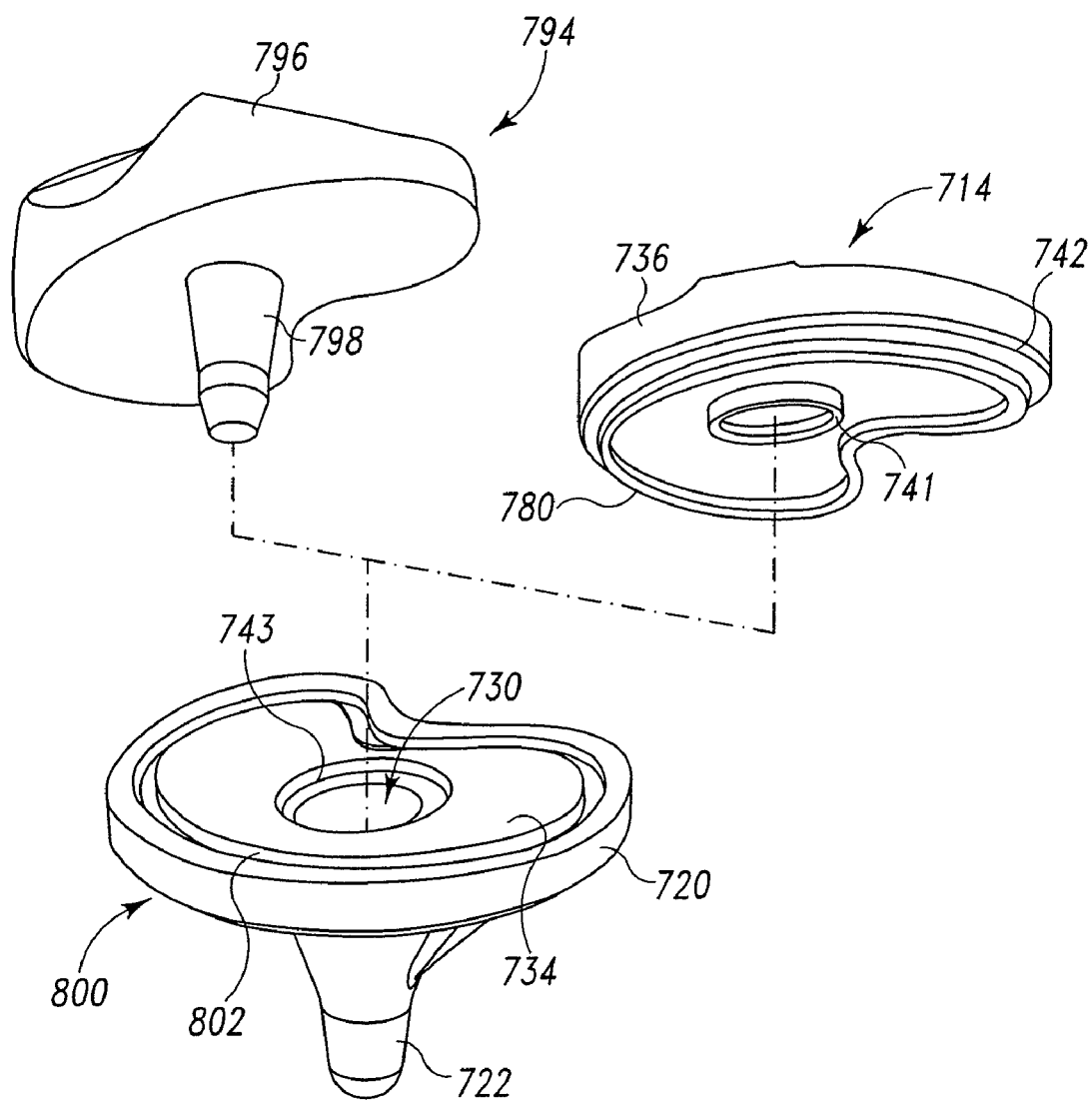
FIG. 87 is a perspective view of a tibial system including a tibial tray having a recessed track formed therein, a rotating tibial insert, and a fixed tibial insert having a rail to be received within the recessed track of the tray.

Looking now to FIG. 87, a prosthetic knee assembly includes a rotating tibial insert 794 having a platform 796 and a stem 798 coupled thereto. The tibial insert 714 having the continuous rail 780 about the perimeter of the platform 742 (also shown in FIG. 20) provides the fixed tibial insert. A tibial tray 800 may be used with either the rotating tibial insert 794 or the fixed tibial insert 714. Illustratively, the tibial tray 800 includes the platform 720, the stem 722 coupled thereto, and the bore 730 formed through the platform 720 and into the stem 722. A recessed track 802 is formed around the perimeter of the top surface 734 of the platform 720. The track 802 defines a closed path and corresponds in size and shape to the continuous track or rail 780 of the fixed tray 714 shown in FIGS. 20 and 87. Illustratively, the insert 714 includes a center hub or ring 741 configured to be received within a recessed portion 743 formed in the platform 720 of the tray 800 around the bore 730. Illustratively, the track 780 of the insert 714 is made of metal and is formed integrally with the metal backing 742 compression molded to the polymer platform portion 736. Alternatively, the metal track 780 may be compression molded directly to the polymer platform portion 736. In use, the stem 798 of the rotating tibial insert 794 may be inserted into the bore 730 of the tibial tray 800 to provide a rotating tibial assembly. Alternatively, the hub 741 and rail 780 of the fixed tibial insert 714 may be received within the corresponding recessed portion 743 and track 802 of the tibial tray to prevent rotation of the tibial insert 714 relative to the tray 800. The fixed tibial insert 714 may further include one or more flexible tabs (not shown) while the tibial tray 800 may include an undercut portion (not shown) in order to receive the flexible tabs therein and further couple the fixed tibial insert 714 to the tray 800.

Figure 22A:
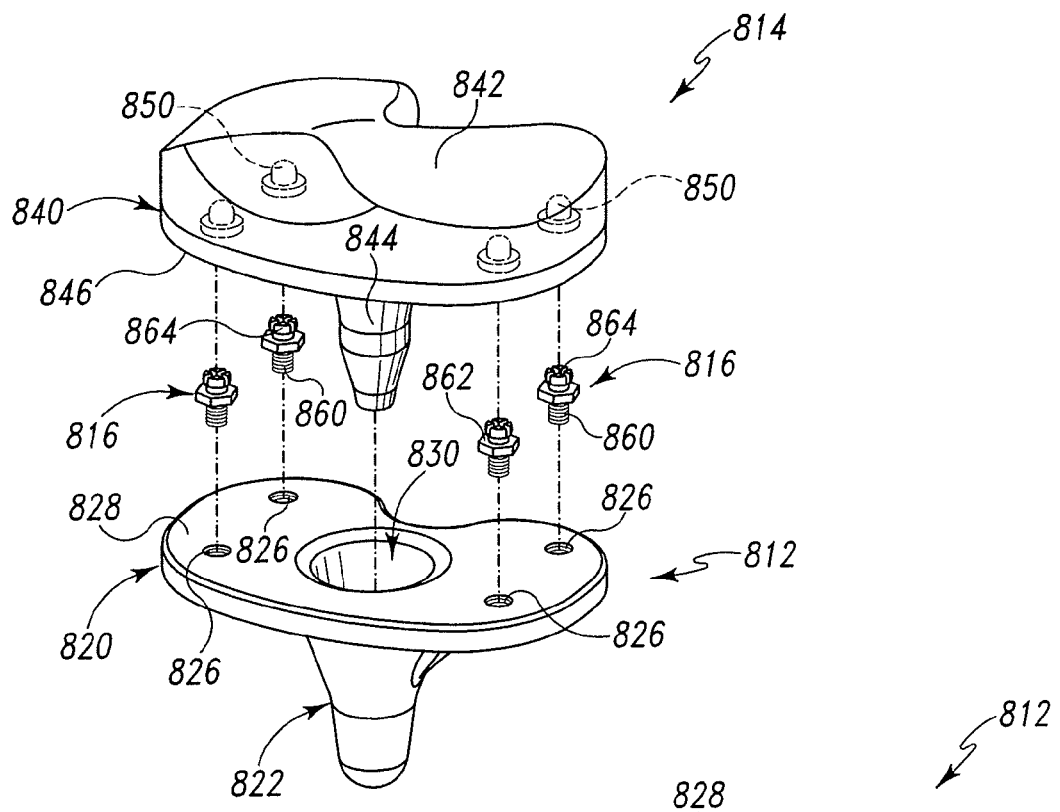
FIG. 22a is a perspective view of a tibial tray, a tibial insert configured to be coupled with the tibial tray, and four threaded posts configured to be coupled to the tibial tray and the tibial insert when the tibial insert is to be used as non-rotating tibial insert.
Figure 22B:
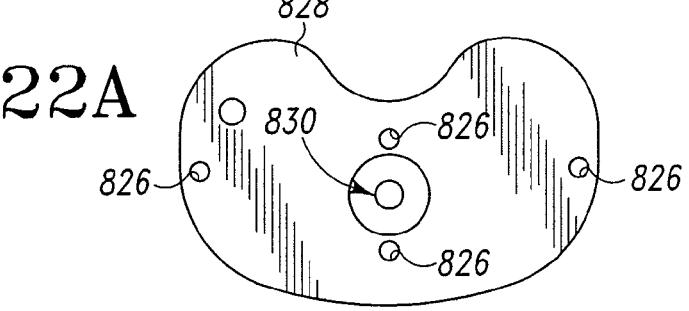
FIG. 22b is a top view of the tibial tray of FIG. 22a showing an alternative configuration for a plurality of threaded bores of the tibial tray.
Figure 23:
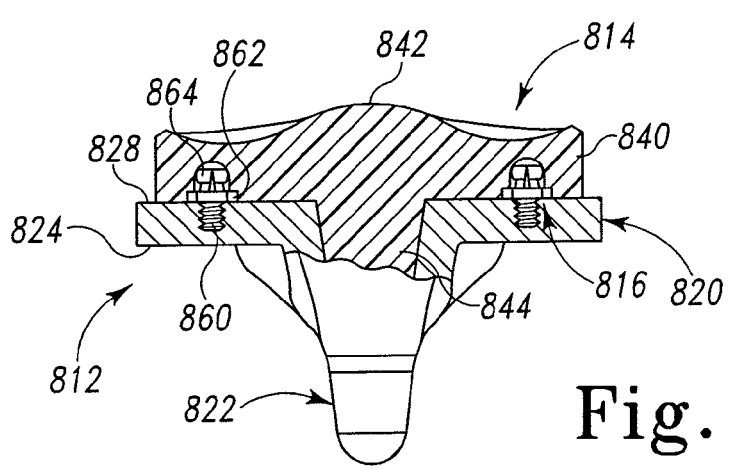

Looking now to FIGS. 22a, 22b, and 23, another prosthetic knee assembly includes a tibial tray 812, a tibial insert 814, and four locking posts 816. Illustratively, the tibial tray 812 and the tibial insert 814 (without use of the posts 816) cooperate to provide a rotating tibial assembly while the tibial tray 812, tibial insert 814, and the posts 816 cooperate to prove a fixed tibial assembly.

Illustratively, the tibial tray 812 includes a platform 820 and a stem 822 coupled to a bottom surface 824 of the platform 820. Four threaded bores 826 are formed in the upper surface 828 of the platform 820. The tibial insert 814 includes a platform 840 having an upper bearing surface 842 and a stem 844 coupled to a bottom surface 846 of the platform 840. Four countersunk bores 850 are formed in the bottom surface 846 of the platform 840. Each locking post 816 includes a threaded stem 860, a hexagonal washer 862, and a slotted head 864.

In a first configuration providing the fixed tibial assembly, each post 816 is threaded into a respective threaded bore 826 of the platform 820 of the tibial tray 812 such that the hexagonal washer 862 is engaged with the upper surface 828 of the platform 820. The stem 844 of the tibial insert 814 is received within the bore 830 of the tibial tray 812 and the platform 840 of the tibial insert 814 is snapped onto the exposed heads 864 of the posts 816 such that each head 864 is received within a respective bore 850 of the platform 840 of the tibial insert 814. Illustratively, the head 864 of each post 816 is slotted such that portions of each head 864 may deflect or collapse inwardly during installation to create a bias upon the inner wall of the respective bore 850 within which each post 816 is received. In other words, the size of each bore 850 is smaller than the un-collapsed size of each head 864 in order to maintain the respective head 864 in slight compression within the bore 850 to assist in retaining the insert 814 against the tray 812. In such a configuration, the tibial insert 814 is prevented from rotating relative to the tibial tray 812. In a second configuration, the posts 816 are not coupled to the tibial tray 812 and the tibial insert 814, when received upon the tray 812, is permitted to rotate relative to the tibial tray 812. In such a configuration, the bores 850 of the polymer tibial insert 814 may be filled or plugged with a metal post (not shown) in order to prevent any cold flow of the polymer platform 840 into the bores 850 when the locking posts 816 are not being used. Accordingly, The posts 816 may be selectively used to convert the prosthetic knee system from a rotating tibial assembly to a fixed tibial assembly.

Illustratively, as shown in FIG. 22a, the threaded bores 826, countersunk bores 850, and locking posts 816 are positioned generally under a load bearing portion (i.e., below the condylar surfaces 842) of the tibial insert 814. Alternatively, as shown in FIG. 22b, two of the threaded bores 826 of the tray 812 may be positioned anteriorly and posteriorly of the bore 830 and within close proximity to the bore 830 while two other threaded bores 826 may be positioned medially and laterally of the bore 830 near an outer periphery of the platform 820 of the tray 812. Accordingly, the countersunk bores 850 of the tibial insert 814 may be located in positions which correspond to the alternatively placed bores 826. As such, the locking posts 816 received within the alternatively placed bores 826, 850 are not positioned directly under any major load bearing portions of the tibial insert 814.

Figure 24:
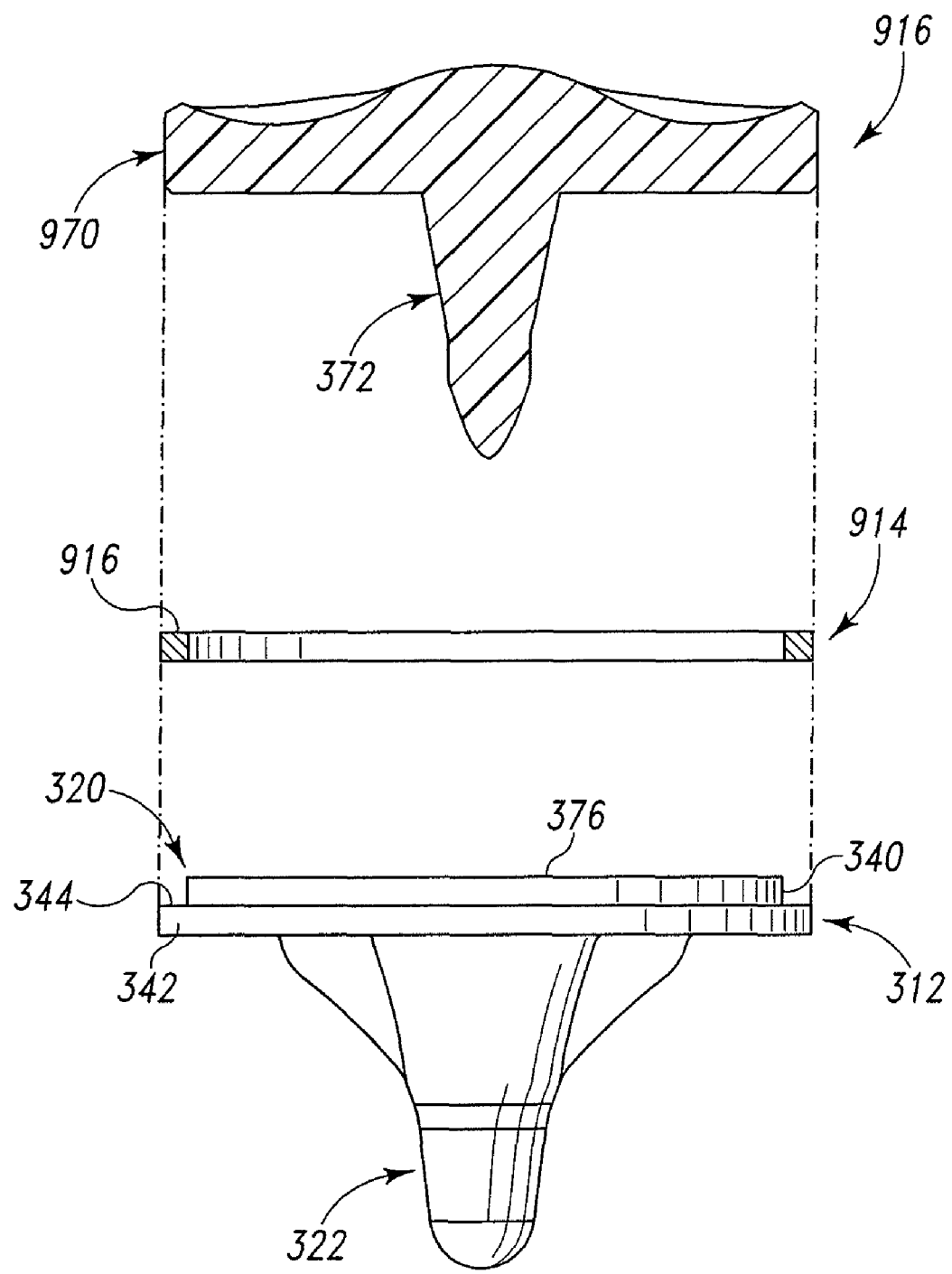
FIG. 24 is a part-side, part-sectional view of a rotating tibial assembly including a rotating tibial insert, a tibial tray, and a ring.

Looking now to FIG. 24, another prosthetic knee system includes the tibial tray 312 of FIGS. 10-13, a metal ring 914, and a tibial insert 916 similar to the tibial insert 314 shown in FIGS. 12 and 13. The prosthetic knee system shown in FIG. 24 is similar to that shown in FIGS. 10-13; as such, like reference numerals have been used to denote like components. In particular, FIG. 24 shows the tibial tray 312 shown in FIG. 12 which may be used either with the tibial insert 314 shown in FIGS. 10-11 to provide a fixed tibial assembly or with the tibial insert 316 shown in FIG. 12-13 to provide a rotating tibial assembly. Further, as shown in FIG. 24, the tibial tray 312 may be used with the metal ring 914 which is sized to rest upon the outer ledge 344 of the lower platform 342 in order to surround the upper platform 340 and is positioned such that an upper surface 916 of the metal ring 914 is generally flush with the upper surface 376 of the upper platform 340. As such, the metal ring 914 effectively operates to increase the footprint or size of the surface upon which the platform of any tibial insert may rest. By increasing the size of this surface, a tibial insert, such as the tibial insert 916 shown in FIG. 24, which has a platform 970 having a footprint larger than that of the platform 370 of the tibial insert 316 shown in FIG. 12, for example, may be used. In other words, a wider tibial insert, such as the tibial insert 916, having a bottom platform surface defining a larger platform surface area may be used. As such, the metal ring 914 allows the tibial tray 312 to be used with tibial inserts of varying sizes.

Figure 25:
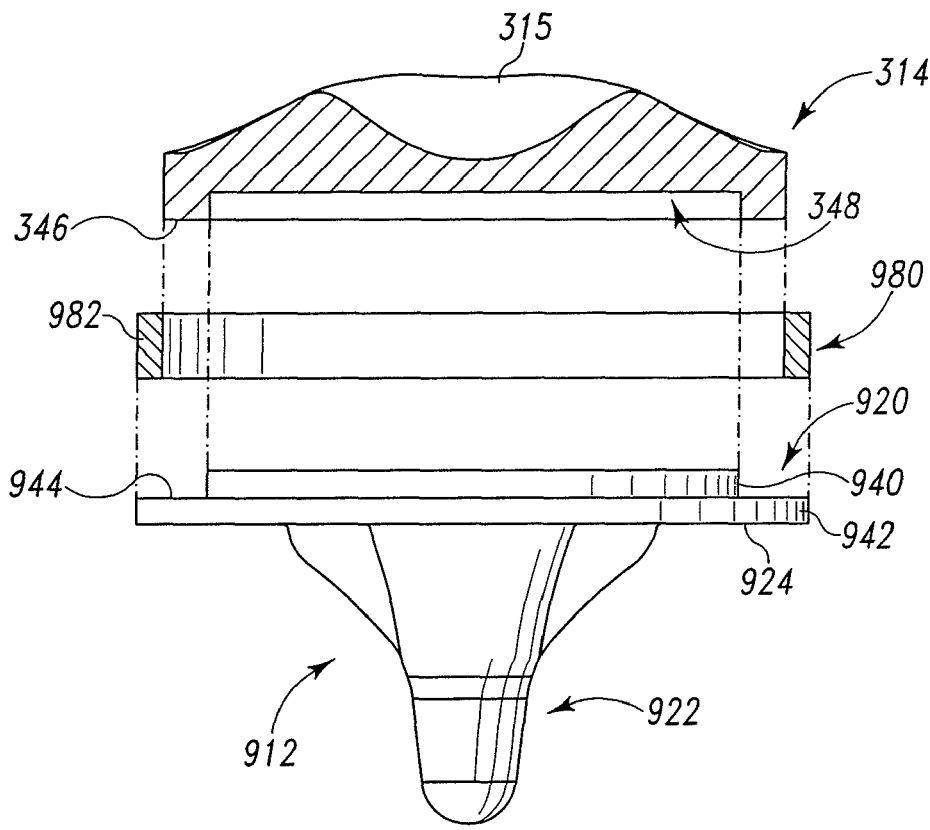
FIG. 25 is an exploded, part-side, part-sectional view of a non-rotating tibial assembly including a non-rotating tibial insert, a tibial tray, and a ring.
Figure 26:
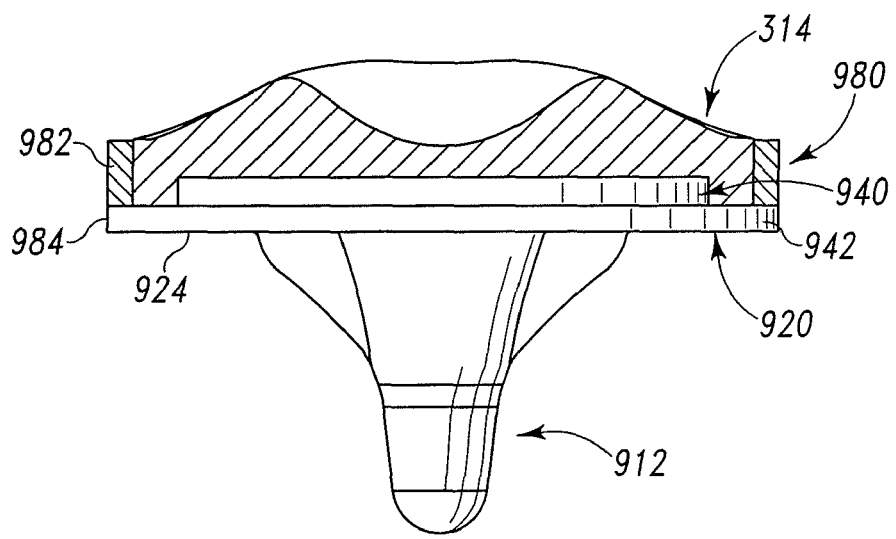
FIG. 26 is an assembled, sectional view of the tibial system of FIG. 25.

Looking now to FIGS. 25-26, still another prosthetic knee assembly is provided. Various components of the prosthetic knee assembly of FIGS. 25-26 are the same as or similar to the components shown in FIGS. 10-11; as such, like reference numerals are used to denote like components. A tibial tray 912 shown in FIGS. 25 and 26 includes a platform 920 and a stem 922 coupled to the bottom surface 924 of the platform 920. The platform 920 includes a center stepped section to define an upper platform 940 and a lower platform 942. The lower platform 942 is larger than the upper platform 940 to define an outer ledge 944 of the platform 920.

The fixed tibial insert 314 includes the recess 348 to receive the upper platform 940 of the tibial tray 912 therein. In such a position, the fixed tibial insert 314 is prevented from rotating relative to the tray 912. As shown in FIGS. 25 and 26, the tibial insert 314 is sized such the lower platform 942 of the tibial tray 912 extends beyond an outer perimeter of the tibial insert 314. A locking metal ring 980 is further provided to fit around the fixed tibial insert 314, as shown in FIG. 26. Illustratively, the metal ring 980 is sized for positioning on the portion of the ledge 944 of the lower platform 942 of the tibial tray 912 which extends beyond the outer perimeter of the tibial insert 314. In this position, an outer surface 982 of the metal ring 980 is generally flush with the outer surface 984 of the lower platform 942 of the tray 912. The locking metal ring 980 may be friction-fit, taper-fit, or snap-fit around the tibial insert 314 in order to further prevent the rotational movement of the tibial insert 314 relative to the tibial tray 912 as well as any micro-motion between the two components.

Figure 27:
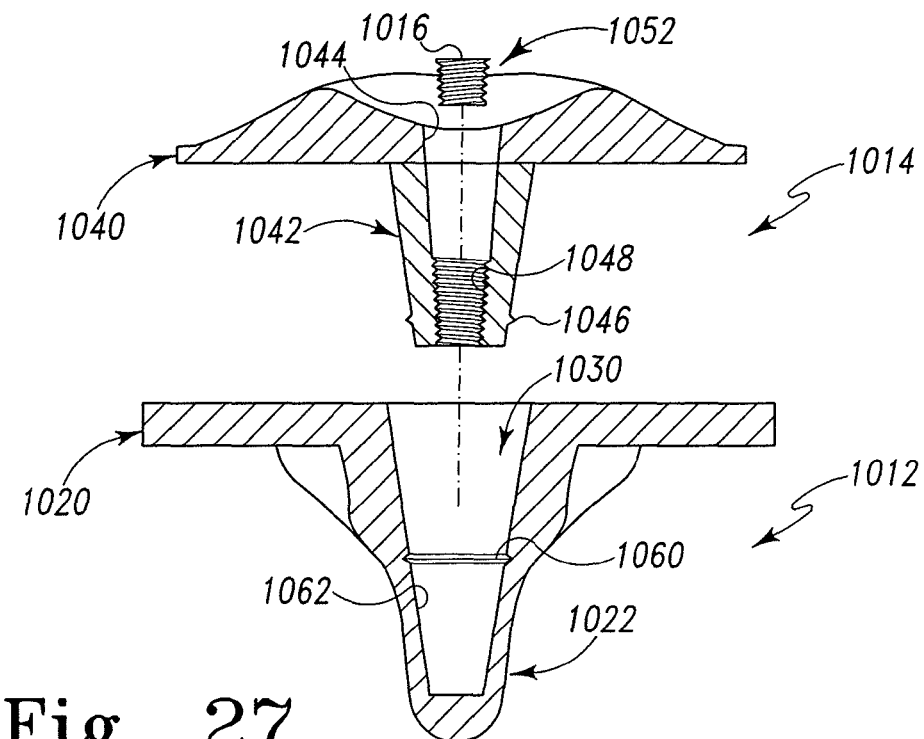
FIG. 27 is an exploded, sectional view of another prosthetic knee system including a tibial tray, a tibial insert, and a fastener.
Figure 28:
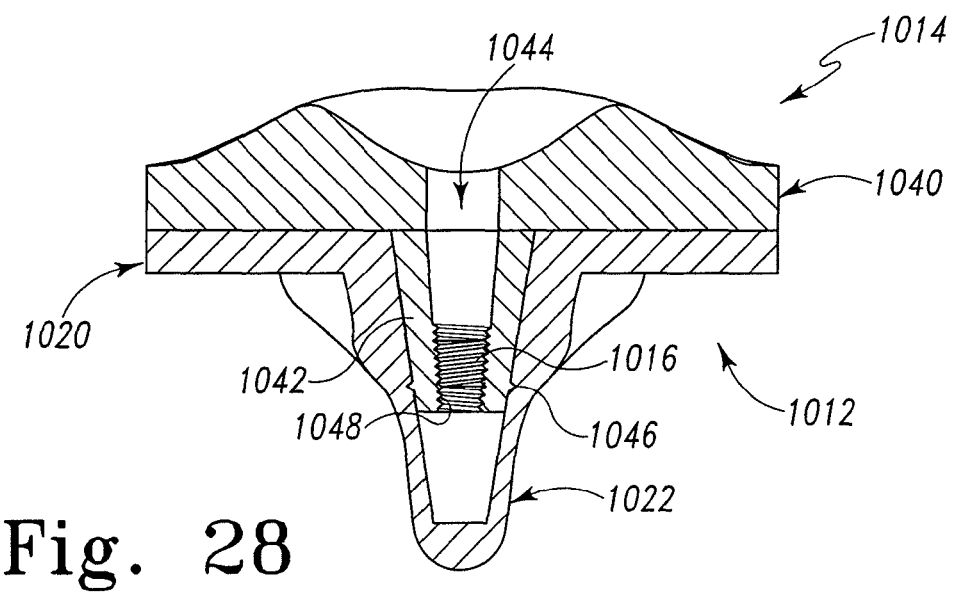
FIG. 28 is an assembled, sectional view of the prosthetic knee system of FIG. 27.
Figure 29:
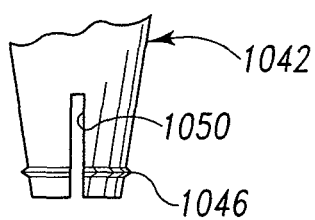
FIG. 29 is a side view of a portion of the stem of the tibial tray of the prosthetic knee system of FIGS. 27-28.
Figure 30:
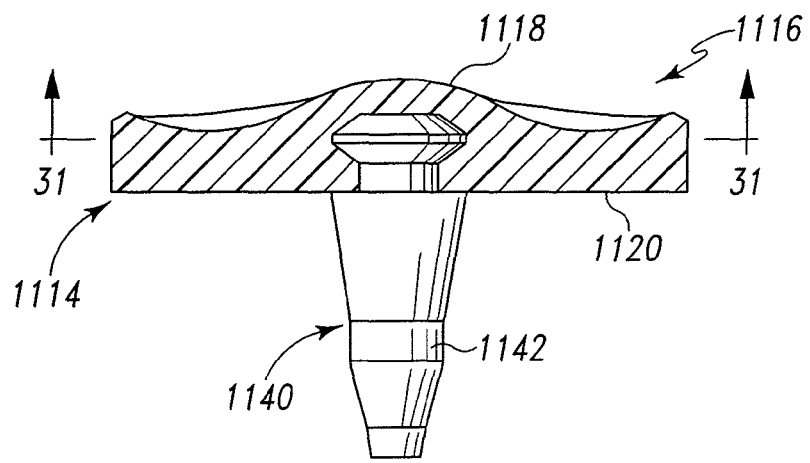
FIG. 30 is a part-sectional, part-side view of a tibial insert including a platform and a stem removably coupled to the platform.
Figure 31:
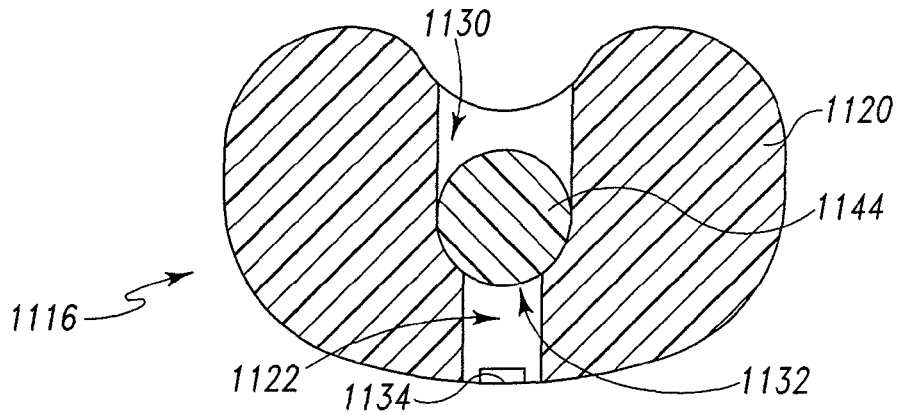
FIG. 31 is a bottom, sectional view taken along line 31-31 of the tibial insert of FIG. 30 showing a track formed in the platform to permit anterior/posterior glide of the platform relative to the stem.

Looking now to FIGS. 27-29, another prosthetic knee assembly includes a tibial tray 1012, a tibial insert 1014, and a set screw 1016. The tibial tray 1012 includes a platform 1020, a stem 1022, and a bore 1030 through the platform 1020 and into the stem 1022. The tibial insert 1014 similarly includes a platform 1040, a stem 1042, and a tapered bore 1044 through the platform 1040 and the stem 1042. The stem 1042 of the tibial insert 1014 includes an outer rim 1046. Further, the distal end of the bore 1044 is threaded to include threads 1048, as shown in FIG. 27. Looking to FIG. 29, the distal end of the stem 1042 of the tibial insert 1014 further includes a slit 1050 to allow the distal end of the stem 1042 to be narrowed and widened. The set screw 1016 includes outer threads 1052.

In a first, rotational configuration, the stem 1042 of the tibial insert 1014 is received within the bore 1030 of the tibial tray 1012 such that the annular, outer rim 1046 of the tibial insert 1014 is positioned within an annular groove 1060 formed in inner surface 1062 of the stem 1022 of the tibial tray 1012. Without the use of the set screw 1016, the tibial insert 1014 is able to rotate relative to the tibial tray 1012 about a longitudinal axis running through the stem 1022 of the tray 1012. The outer rim 1046 of the tibial insert 1014 positioned within the groove 1060 of the tibial tray 1012 aides in preventing lift-off of the tibial insert 1014 relative to the tibial tray 1012 during use.

In a second, fixed configuration, the set screw 1016 is received within the bore 1044 of the tibial insert 1014 and is threaded into the distal end of the tapered bore 1044 of the tibial insert 1014. As the set screw 1016 is threaded distally within the tapered bore 1044, the distal end of the stem 1042 is forced to expand outwardly against the inner surface 1062 of the stem 1022 of the tibial tray 1012. As such, the stem 1042 of the tibial insert 1014 becomes press-fit into the stem 1022 of the tibial tray 1012 in order to prevent rotational movement of the tibial insert 1014 relative to the tibial tray 1012.

Looking now to FIGS. 30-33, a modular tibial insert 1114 for use with a tibial tray (not shown) is provided. Illustratively, the tibial insert 1114 includes a platform 1116, an anterior-posterior-glide (APG) stem 1152 (shown in FIG. 33) for selective use with the platform 1116, and a rotating-platform stem (RP) 1140 (shown in FIGS. 30 and 32) for selective use with the platform 1116 as well. Accordingly, the modular tibial insert 1114 disclosed in FIGS. 30-33 provides an APG tibial insert including the platform 1116 and the APG stem 1152 as well as rotating or mobile tibial insert including the RP platform 1116 and the stem 1140. Illustratively, the modular tibial insert 1114 may be used during minimally-invasive or traditional knee replacement surgeries.

Figure 32:
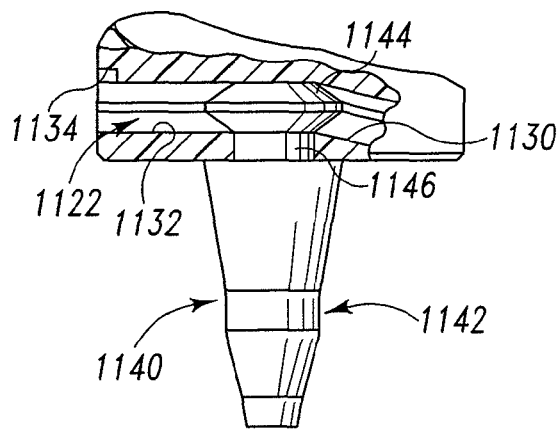
FIG. 32 is a side view with portions broken away of the tibial insert of FIGS. 30 and 31.

The platform 1116 includes an upper bearing surface 1118, a bottom surface 1120, and an anterior/posterior track 1122 formed in the bottom surface 1120 of the platform 1116. The anterior/posterior track 1122 includes an angled or ramped portion 1130, as shown in FIG. 32, as well as a straight portion 1132 which is generally parallel to the bottom surface 1120 of the platform 1116. A notch 1134 is further formed within the anterior/posterior track 1122, as shown best in FIG. 31.

The RP stem 1140 includes a tapered stem portion 1142, a head portion 1144, and a narrowed neck portion 1146 coupled to and positioned between both the stem portion 1142 and the head portion 1146. Illustratively, the head portion 1142 is generally axially symmetrical about a longitudinal axis along the stem portion 1144. In use, the RP stem 1140 is first inserted into a bore formed in a corresponding tibial tray (not shown) and the platform 1116 is slid onto the head portion 1144 of the RP stem 1140. In other words, the head portion 1144 of the stem 1140 is positioned within the track 1122 and travels along the track 1122 to a central location of the track 1122 where the head portion 1144 is locked into place relative to the platform 1116 to provide a rotating tibial insert able to rotate about an axis through the stem 1140 relative to the tibial tray upon which it rests.

Figure 33:
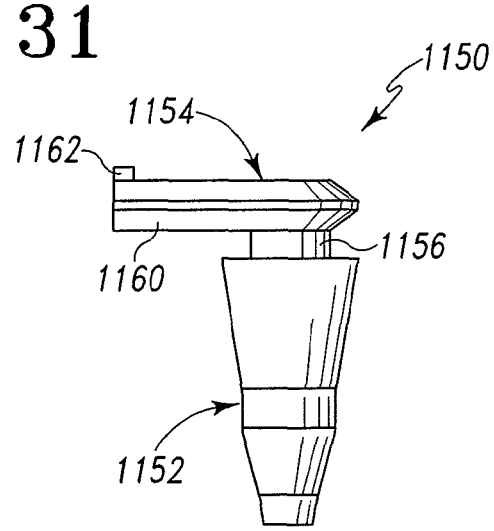
FIG. 33 is a side view of an alternative stem for use with the tibial insert of FIGS. 30-32.

As noted above, the modular tibial insert of FIGS. 30-33 further includes an anterior-posterior-glide (APG) stem 1152 (shown in FIG. 33) including a tapered stem portion 1152, a head portion 1154, and a narrowed neck portion 1156 coupled to and positioned between both the stem portion 1152 and the head portion 1154. As shown in FIG. 33, the head portion 1152 includes a posteriorly-extending glide arm 1160. A removable stopper 1162 may be selectively coupled to an anterior end of the arm 1160 and/or received within an anterior notch 1134 of the track 1122 of the platform 1116.

In use, the APG stem 1150 is first inserted into a bore formed in a corresponding tibial tray (not shown) and the platform 1116 is slid onto the head portion 1154 of the APG stem 1150 such that the glide arm 1160 is positioned within the track 1122. The removable stopper 1162 may then be positioned either within the notch 1134 formed in the track 1122 of the platform 1116 or on the anterior end of the glide arm 1160. The stopper 1162 operates to prevent anterior motion of the platform 1116 relative to the APG stem 1150 beyond a certain predetermined point while posterior motion of the platform 1116 relative to the APG stem is illustratively not limited. Illustratively, the APG insert described herein is similar to other known APG inserts disclosed in U.S. Patent Application Publication Nos. US2004/0204765 and US2003/0195634 each titled PROSTHETIC KNEE WITH REMOVABLE STOP PIN FOR LIMITING ANTERIOR SLIDING MOVEMENT OF BEARING, for example.

Figure 34A:
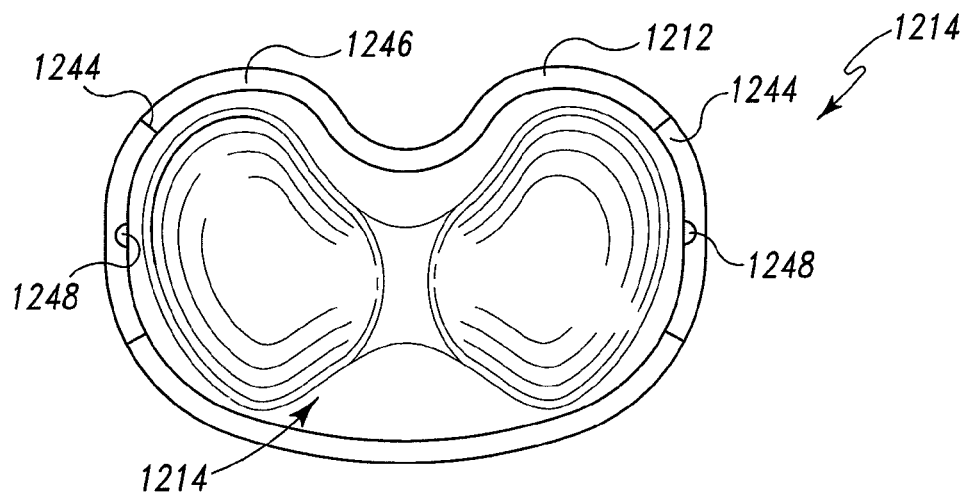
FIG. 34a is a top view of a orthopaedic prosthesis assembly including a tibial tray having two peripheral rails and a fixed tibial insert retained in a fixed position relative to the tibial tray.
Figure 34B:
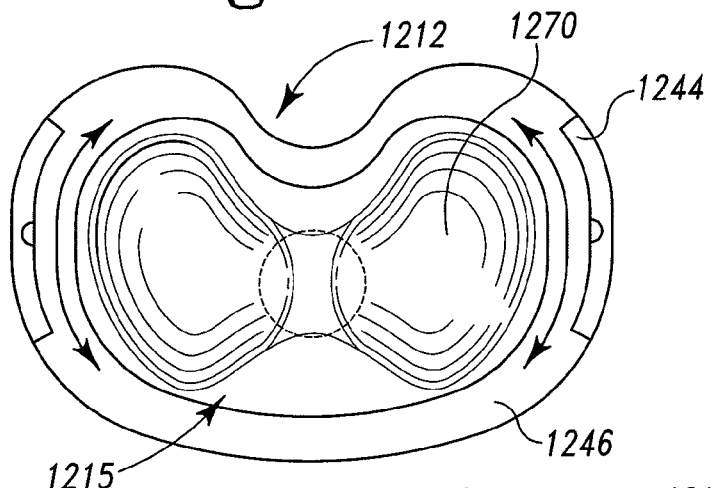
FIG. 34b is a top view of a rotating tibial assembly including the tibial tray shown in FIG. 34a and a rotating tibial insert free to rotate relative to the tibial tray.
Figure 35:
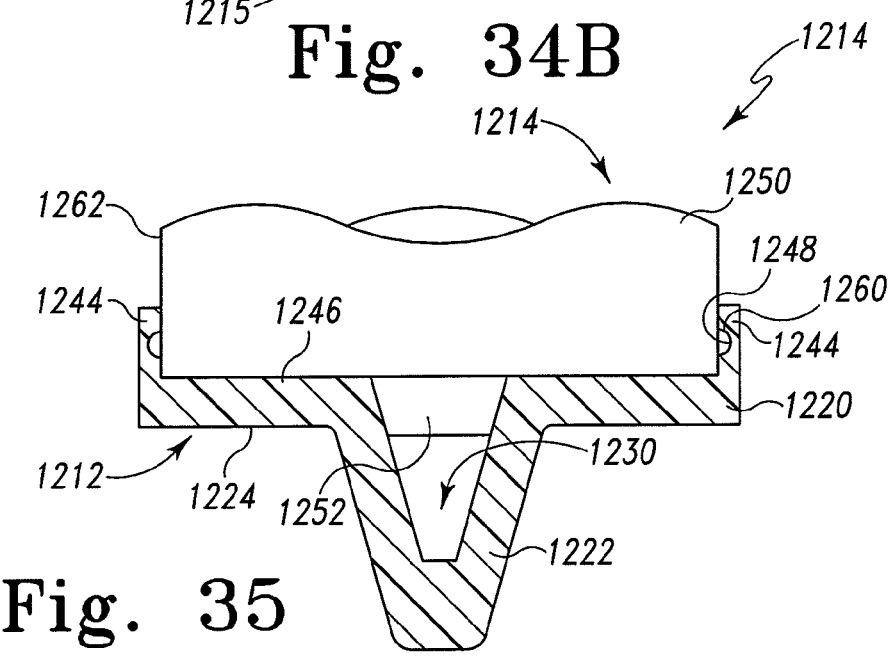
FIG. 35 is a sectional view of the tibial tray and the fixed tibial insert of FIG. 34a showing the tibial insert received within the rails of the tibial tray.
Figure 36:
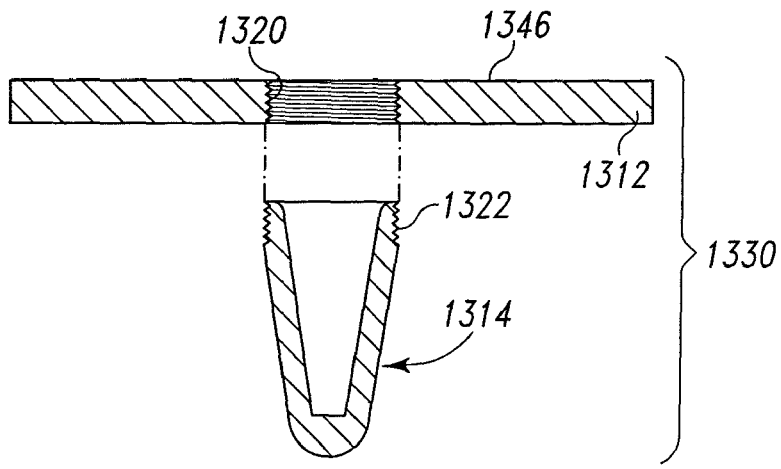
FIG. 36 is a sectional view of a modular tibial tray including a platform component and a mobile stem component.

Looking now to FIGS. 34a, 34b, and 35, another prosthetic knee system includes a fixed tibial insert 1214, a mobile tibial insert 1215, and a tibial tray 1212. The tibial tray 1212 includes a platform 1220 and a stem 1222 coupled to a bottom surface 1224 of the platform 1220. Medial and lateral rails 1244 of the tibial tray 1212 extend upwardly from an upper surface 1246 of the platform 1220. Illustratively, the peripheral rails 1244 are positioned laterally or outwardly from the center of the tray 1212. As is discussed below, the rails 1244 operate as a peripheral capture mechanism to maintain the fixed tibial insert 1214 therein. Further, each peripheral rail 1244 includes a notch or recess 1248, as shown in FIG. 35.

The fixed tibial insert 1214, shown in FIGS. 34a and 35 includes a platform 1250 and a stem 1252 configured to be received within a cavity or bore 1230 of the tray 1212. The platform 1250 of the insert 1214 further includes flexible tabs 1260 extending from a side wall 1262 of the platform 1250. Illustratively, the platform 1250 of the fixed insert 1214 is sized to be received within the peripheral rails 1244 of the tray 1212 such that the flexible tabs 1260 are received within the corresponding notches 1248 of each wall 1244. As such, the outer, peripheral rails 1244 of the tray 1212 create a partial "skirt" to contain the tibial insert 1214 therein and to prevent rotation of the tibial insert 1214 relative to the tibial tray 1212. The notches 1248 and corresponding tabs 1260 operate to further couple the insert 1214 to the tray 1212 to prevent lift-off of the insert 1214 relative to the tray 1212 during use.

The rotating tibial insert 1215, shown in FIG. 34b, includes a platform 1270 smaller than the platform 1250 of the fixed tibial insert 1215 such that clearance or space between the peripheral rails 1244 of the tray 1212 and the platform 1270 allows the platform 1270 to rotate relative to the tray 1212. In other words, the platform 1270 of the rotating tibial insert 1215 is sized to enable the insert 1215 to rotate within the periphery capture mechanism, or rails 1244, of the tibial tray 1212. Accordingly, the tibial insert 1215 and the tray 1212 cooperate to provide a rotating tibial assembly.

Figures 39, 40:
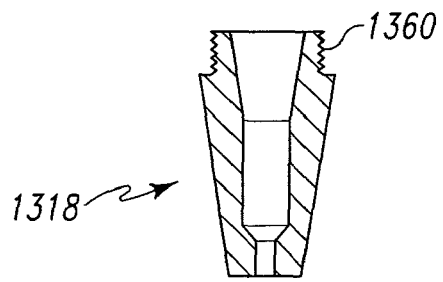
FIG. 39 is a bottom view of the fixed stem component of FIGS. 37 and 38.
FIG. 40 is a sectional view of a revision stem component configured to be coupled to the platform component shown in FIG. 36.

Looking now to FIGS. 36-39, another prosthetic knee assembly includes a modular tibial tray assembly including a platform 1312 (shown in FIGS. 36 and 38), a rotating-insert stem 1314 (shown in FIG. 36), a fixed-insert stem 1316 (shown in FIGS. 37 and 38), and a revision stem 1318 (shown in FIG. 40). In a first configuration, a threaded aperture 1320 of the platform 1312 is threaded onto a threaded proximal end 1322 of the rotating-insert stem 1314. In such a configuration, the platform 1322 and stem 1314 cooperate to provide a tibial tray 1330 for use with a tibial insert (such as the tibial insert 414 shown in FIG. 14, for example) which is able to rotate relative to the tibial tray 1330.

In another configuration, the platform 1312 is coupled to the fixed-insert stem 1316. The fixed-insert stem 1316 includes a stem portion 1340 having a threaded proximal end 1342 and a T-shaped head portion 1344 coupled to the proximal end 1342 of the stem 1316. The threaded aperture 1320 of the platform 1312 is threaded onto the proximal end 1342 of the stem 1316 such that the head portion 1344 of the stem 1316 is positioned above an upper surface 1346 of the platform 1312. In such a configuration, the platform 1312 and the fixed-insert stem 1316 cooperate to provide a tibial tray 1348 for use with a tibial insert 1350 as discussed below.

Figures 37, 38:
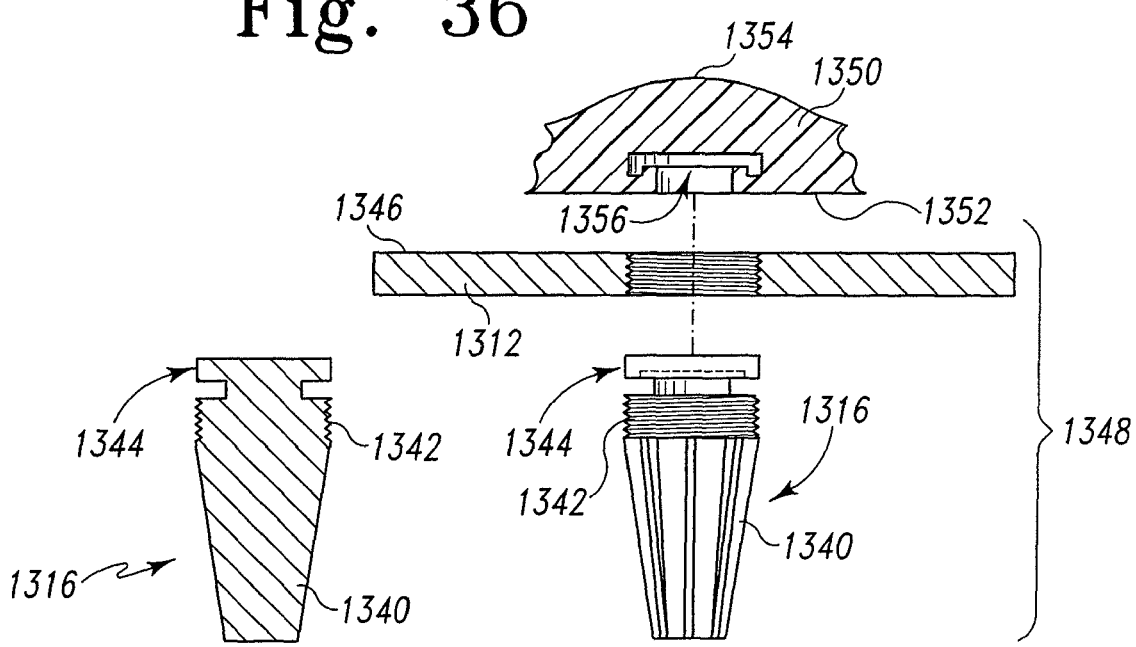
FIG. 37 is a sectional view of a fixed stem component able to be coupled to the platform component shown in FIG. 36.
FIG. 38 is a side view of the fixed stem component of FIG. 37 and a fixed tibial insert (shown in section) configured to be coupled to the fixed stem component.

The fixed tibial insert 1350, as shown in FIG. 38, includes a bottom surface 1352, an upper bearing surface 1352 and a T-shaped bore 1356 formed in the bottom surface 1352 of the insert 1350. The fixed tibial insert 1350 may be snapped onto the fixed-insert stem 1316 such that the head portion 1344 of the stem 1316 is received within the bore 1356 of the fixed tibial insert 1350. Illustratively, the head portion 1344 of the stem 1316 may be square-shaped or generally non-circular in shape when viewed in a plan view while the corresponding bore 1356 of the fixed tibial insert 1350 may define a coordinating shape formed to receive the head portion 1344 therein. By providing a non-circular shape of the head portion 1344 and the bore 1356, the fixed tibial insert 1350 is prevented from rotating relative to the tray 1348.

Illustratively, the stem portion 1340 of the fixed-insert stem 1316 is splined, as shown in FIG. 39, such that the stem portion 1340 may be compressed and expanded as desired. Further, the prosthetic knee assembly shown in FIGS. 36-40 includes the revision stem 1318 having a threaded proximal end 1360, as shown in FIG. 40. Similar to that described above, the platform 1312 may be threadably coupled to the revision stem 1318 for use as a revision tibial tray.

Figure 41:
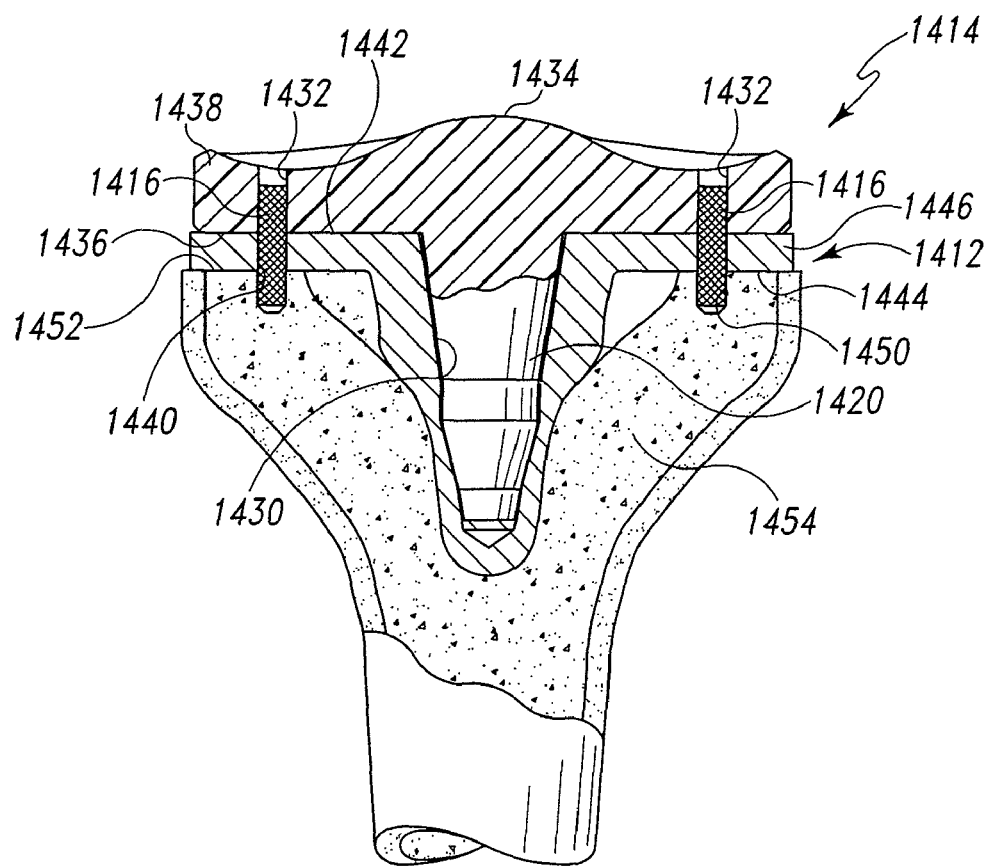
FIG. 41 is a part-sectional view of a prosthetic knee system including a tibial insert, a tibial tray, and a plurality of locking posts.
Figure 42:
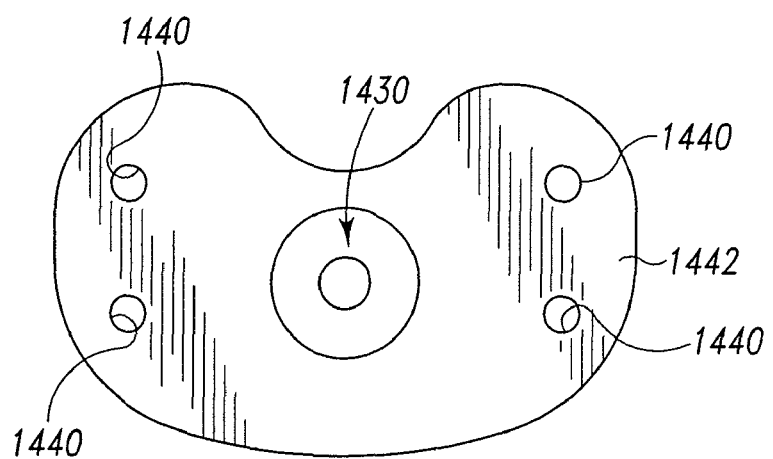
FIG. 42 is a top view of the tibial tray of FIG. 41 including through-holes for receiving the locking posts to fix the tibial bearing relative to the tibial tray.
Figure 43:
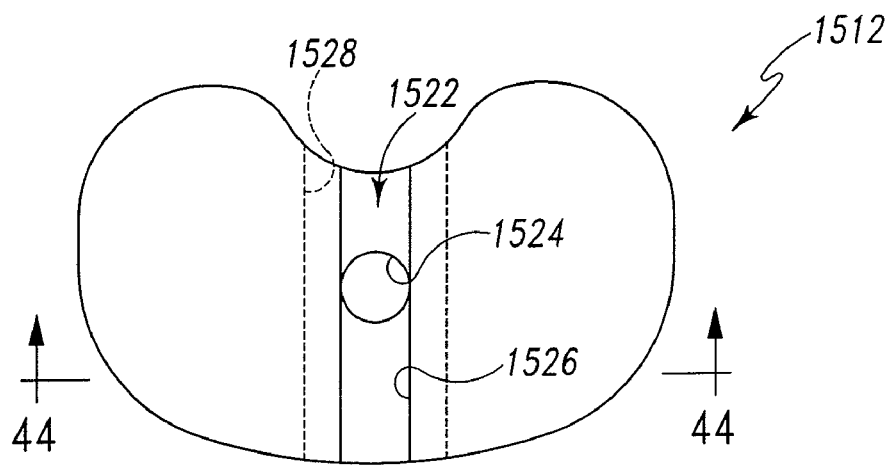
FIG. 43 is a bottom view of a platform component of a modular tibial insert including an opening and a guide track formed in a bottom surface of the platform component.

Looking now to FIGS. 41 and 42, a prosthetic knee system includes a tibial tray 1412, a tibial insert 1414, and four locking posts 1416. In a first configuration, a stem 1420 of the tibial insert 1414 is received within a bore 1430 of the tibial tray 1412. The tibial insert 1414 includes four through-holes 1432 extending from an upper bearing surface 1434 to a bottom surface 1436 of the platform 1438 of the insert 1414. The holes 1432 of the tibial insert 1414 are aligned with four through-holes 1440 of the tibial tray 1412 which each extend from a top surface 1442 to a bottom surface 1444 of the platform 1446 of the tray 1412. One of the posts 1416 is then received within the holes 1432, 1440 of the tibial insert 1414 and the tibial tray 1412 in order to prevent rotation of the tibial insert 1414 relative to the tibial tray 1412. As such, the tibial insert 1414, the tibial tray 1412, and the locking posts 1416 cooperate to provide a fixed tibial assembly. Illustratively, the locking posts 1416 may be metal locking posts.

Additionally, as shown in FIG. 41, a surgeon or other technician may drill bores 1450 into the surgically-prepared surface 1452 of the patient's tibia 1454 upon which the platform 1446 of the tibial tray 1412 rests. Such bores 1450 may be positioned to align with the through-holes 1432, 1440 of the insert 1414 and tray 1412 in order to receive a portion of one of the posts 1416 therein. Illustratively, in order to prevent lift-off of the insert 1414 relative to the tray 1412, the posts 1416 and coordinating holes 1432, 1440 may be configured to provide a press-fit, slip-fit, taper-fit, or threaded locking connection.

Of course, the tibial tray 1412 may include blind holes (not shown) formed in the top surface 1442 of the platform 1446 of the tray 1412 rather than the through-holes 1440 shown. As such, it becomes unnecessary to drill aligning bores into the patient's tibia 1454 and shorter posts may be received through the platform 1438 of the tibial insert 1414 and into the blind holes of the tibial tray. Further, the tibial insert 1414 may include blind holes (not shown) formed into the bottom surface 1436 of the platform 1438 of the tibial insert 1414 rather than the through-holes 1432 shown in FIG. 41. Pins (not shown) may then be provided which are received into the blind holes such that the tibial insert with the pins extending downwardly therefrom may be snapped into the blind holes formed in the tray in order to couple the insert to the tray and prevent relative rotational movement therebetween.

Figure 88:
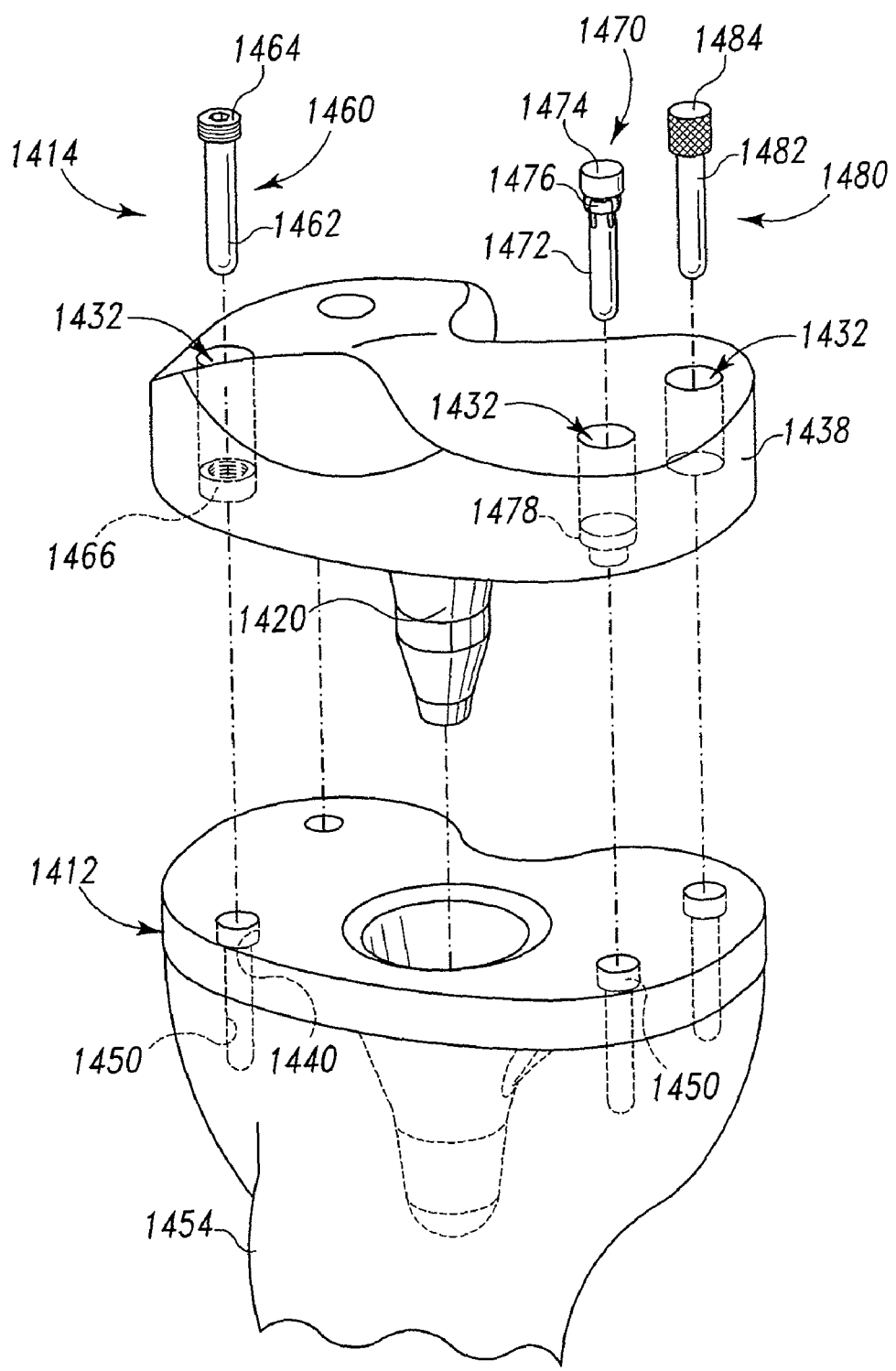
FIG. 88 is a perspective view of the prosthetic knee system shown in FIGS. 41 and 42 showing alternative locking pins for insertion into the tray, the insert, and/or the tibia to prevent movement of the insert relative to the tray.

Looking now to FIG. 88, alternative locking post designs which may be used in addition to or in place of the locking posts 1416 are provided for use with the prosthetic knee system of FIGS. 41 and 42. For example, a first alternative locking post 1460 includes a body 1462 and a threaded head 1464 coupled to the body 1462. Accordingly, the corresponding through-hole 1432 of the tibial insert 1414, includes a threaded insert 1466 (or any threaded end) such that the threaded head 1464 of the post 1416 may be threaded into the insert 1466 in order to secure the post 1461 to the tibial insert 1414. A second alternative locking post 1470 includes a body 1472 and a head 1474 having a locking flange 1476. Accordingly, the corresponding through-hole 1432 includes a cut-out portion 1478 to receive the head 1474 and locking flange 1476 of the post 1470 therein in order to prevent relative movement of the pin 1470 and the tibial insert 1414. Finally, a third alternative locking post 1480 includes a body 1482 and a knurled head 1484 coupled to the body 1482 such that the knurled outer surface of the head 1482 may be press-fit and secured to the smooth inner walls of the corresponding through-hole 1432 formed in the polymer insert 1414. Similar to the locking posts 1416, the alternative locking posts 1460, 1470, and 1480 may be metal as well. As further noted in FIG. 88, the through-holes 1432 formed in the tibial insert 1414 may form rounded edges, rather than sharp edges, within the bearing surface 1434 of the platform 1438 of the insert 1414. Further, while the through-holes 1432 of the insert 1414 and the corresponding holes 1440 of the tray 1412 are shown in particular locations, it is within the scope of this disclosure to orient or position any number of holes 1432, 1440 for receiving various locking pins in any suitable location within the insert 1414 and the tray 1412.

While various locking pins have been shown, it is within the scope of this disclosure to include locking pins which are press-fit, slip-fit, threaded, knurled, tapered, or which include any other suitable locking feature to enable the pins to be fixedly coupled to the tibial insert. As noted above, it is within the scope of this disclosure for the patient's tibia 1454 to be prepared to accept locking pins therein (i.e., including bores 1450 drilled into the surface 1452) or to be non-prepared (i.e., without bores 1450 drilled into the surface 1452) in which case the locking pins may be sized of a suitable length accordingly. Further, the tibial insert 1414 may be configured to include a blind hole or holes (not shown) formed in the bottom surface 1436 of the platform 1438 (rather than the through-holes 1432) within which the locking pin(s) may be received and the tibial tray 1412 may similarly be configured to include a blind hole or holes (not shown) formed in the top surface 1442 of the platform 1446 of the tray 1412 (rather than the through holes 1440) within which the locking pin(s) may be received. Further, while the locking pins 1416, 1460, 1470, 1480 are shown as separate components, it is within the scope of this disclosure for such locking pins to be integral with or compression molded into the underside or bottom surface 1436 of the platform 1438 of the insert 1414 to provide a fixed tibial insert. With such a configuration, a separate rotating tibial insert may be provided for use with the tray 1412 in order to provide a rotating tibial assembly.

In another configuration of the prosthetic knee system shown in FIGS. 41, 42, and 88 the tibial insert 1414 may be used with the tibial tray 1412 without the use of the posts 1416, 1460, 1470, 1480. As such, the tibial insert 1414 is able to rotate relative to the tibial tray 1412 to provide a rotating tibial assembly. Metal plugs (not shown) may be provided to fill the through-holes 1432 in order to prevent any possible cold flow of the polymer platform 1438 into the holes 1432.

Figure 44:
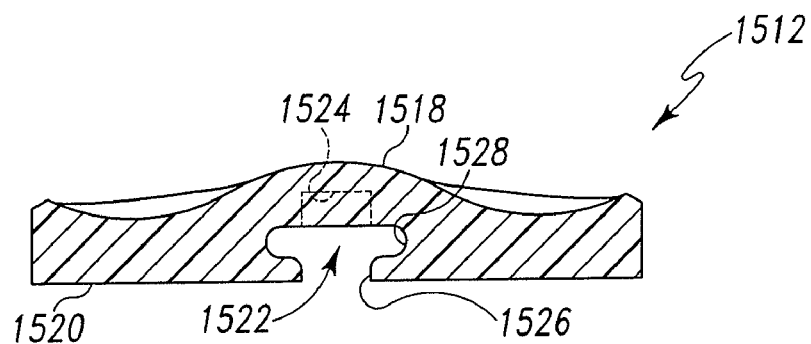
FIG. 44 is a sectional view taken along line 44-44 of the platform component of FIG. 43.

Looking now to FIGS. 43-46, a modular tibial insert system includes a platform 1512 (shown in FIGS. 43 and 44) and a stem 1514. Illustratively, the stem 1514 may be converted for use as an anterior-posterior-glide (APG) stem and a rotating-platform (RP) stem. Illustratively, the platform 1512 includes an upper bearing surface 1518 and a bottom surface 1520. A track 1522 is provided in the bottom surface 1520 of the platform 1512. Illustratively, the track 1522 extends along an anterior/posterior direction and is generally T-shaped when viewed is cross-section, as shown in FIG. 44, to include a narrowed neck portion 1526 and a wider head portion 1528.

The stem 1514 of the modular tibial insert system includes a stem portion 1515, a threaded neck 1517 movable up and down relative to the stem portion 1515, and a guide arm 1516 coupled to the neck 1517. Illustratively, the guide arm 1516 includes an internal shaft 1519 in communication with the neck 1517 to create a worm gear therebetween. The shaft 1519 may be rotated clockwise or counterclockwise using an Allen wrench, for example, in order to move the neck 1517 upwardly or downwardly relative to the stem portion 1515 in order to convert the stem 1514 from an RP stem to an AGP stem, as is discussed below.

The track 1522 of the platform 1512 is configured to receive the guide arm 1516 therein. When the neck 1517 of the stem 1514 is in a lowered position (not shown), such that the upper end of the neck 1517 is positioned in-line with or below the guide arm 1516, the platform 1512 is free to move in an anterior/posterior direction to define an APG tibial insert. The track 1522 and coordinating guide arm 1516 operate to guide the anterior/posterior movement of the platform 1512 on the stem 1516.

Figures 45, 46:
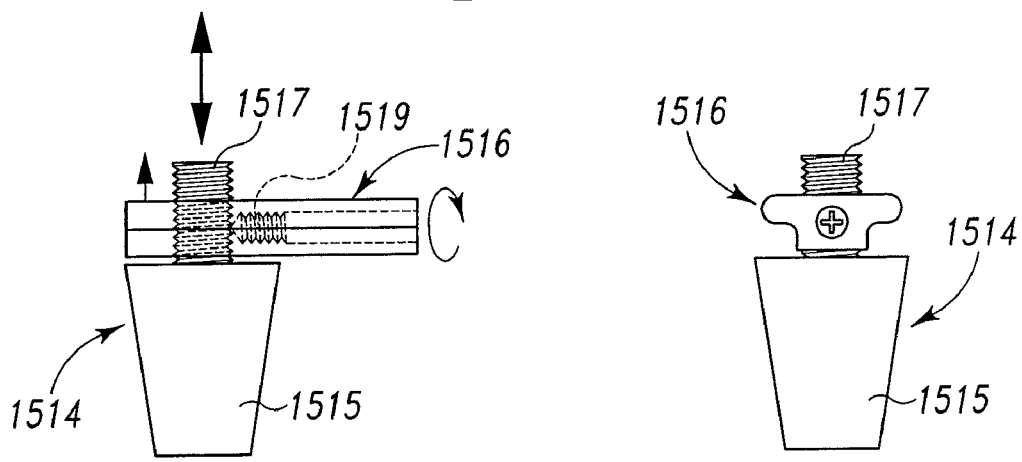
FIG. 45 is a side view of a stem component configured to be coupled to the platform component of FIGS. 43 and 44 in order to form a modular tibial insert.
FIG. 46 is a front view of the stem component of FIG. 45.

Alternatively, the neck 1517 of the stem 1514 may be moved to a raised position, as shown in FIGS. 45 and 46, for example, once the guide arm 1516 is received within the track 1522 of the platform 1522. In the raised position, the upper end of the neck 1517 of the stem 1514 is received within a central bore 1524 formed in the platform 1512. In such a configuration, the platform 1512 is prevented from moving in an anterior/posterior direction relative to the stem 1514. Accordingly, the stem 1514 and the platform 1512 form an RP tibial insert when the neck 1517 of the stem is in the raised position.

Figure 47:
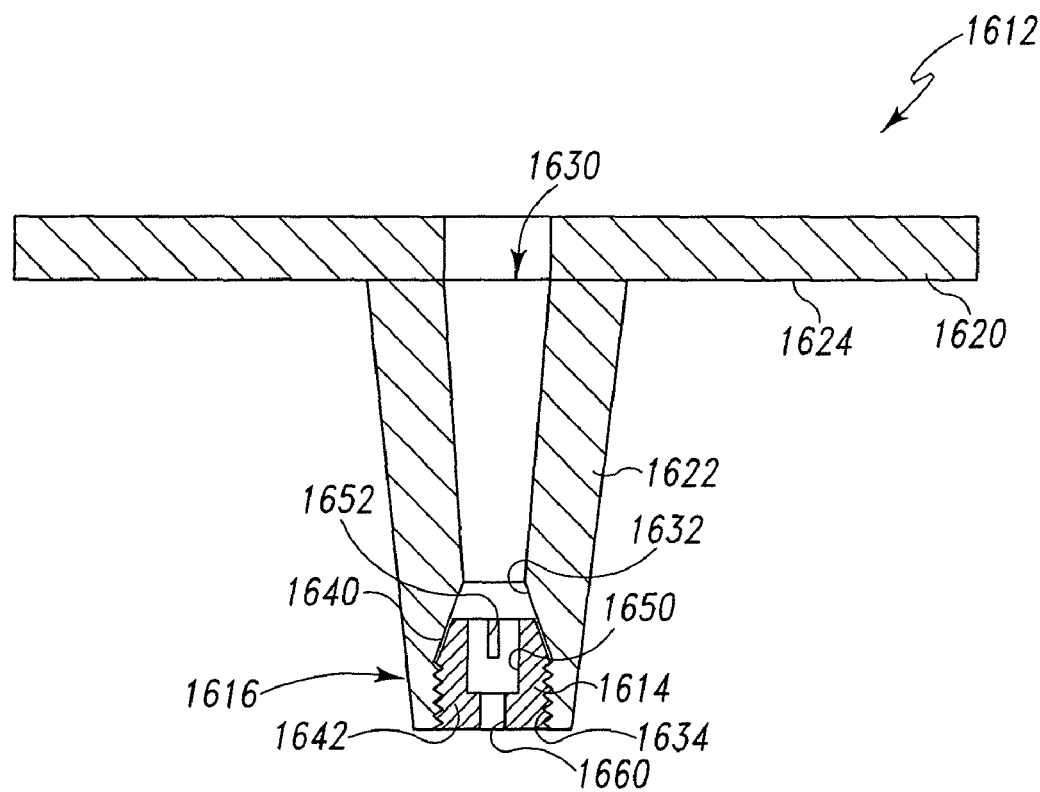
FIG. 47 is a sectional view of a tibial tray including a threaded collet within a distal portion of the stem of the tibial tray.
Figure 48:
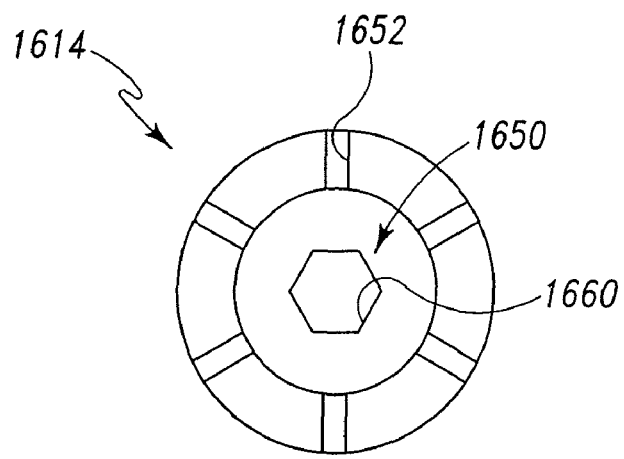
FIG. 48 is an end view of the threaded collet of FIG. 47.

Looking now to FIGS. 47 and 48, another prosthetic knee system includes a tibial tray 1612 and a collet 1614 received within a distal end 1616 of the tibial tray 1612. As shown in FIG. 47, the tibial tray 1612 includes a platform 1620, a stem 1622 coupled to a bottom surface 1624 of the platform 1620, and a bore 1630 formed through the platform 1620 and into the stem 1622. Illustratively, a distal end of the bore 1630 includes both a tapered portion 1632 and a threaded portion 1634, as shown in FIG. 47.

The collet 1614 is positioned within the distal end of the bore 1630 and includes a tapered head portion 1640 and a threaded body portion 1642 configured to be threaded into the threaded portion 1634 of the bore 1630. The collet 1614 includes a central bore 1650 and multiple slots 1652 formed through the tapered head portion 1640 to permit the outer wall portions of the tapered head portion 1640 of the collet 1614 to be compressed or expanded as discussed in greater detail below. The collet 1614 may also include a hexagonal bore 1660 in communication with the central bore 1650 for use with a hexagonal wrench or other similar tool, as is discussed below.

In use, the stem of a tibial insert (not shown) is received within the bore 1630 of the tibial tray 1612 such that a distal end of the stem of the tibial insert is received within the central bore 1650 of the collet 1614. The collet 1614 may be tightened or loosened to prevent or permit rotation of the tibial insert relative to the tibial tray 1612, as discussed below. Illustratively, the tibial insert may include a bore formed therethrough such that a hexagonal wrench may be received through the platform and stem of the tibial tray to engage the hexagonal bore 1660 of the collet 1614 in order to tighten or loosen the collet 1614.

In the tightened position, collet 1614 is moved upwardly within the bore 1630 of the tibial tray such that the tapered walls 1632 of the bore 1630 of the tibial tray 1612 urge the tapered head portion 1640 of the collet 1614 to compress around the distal end of the stem of the tibial insert received within the central bore 1650 of the collet 1614 in order to prevent relative rotational movement therebetween. In other words, the tapered head portion 1640 of the collet 1614 is flexible and is able to be squeezed or contracted around the distal end of the stem of the tibial insert when moved upwardly within the bore 1630. Alternatively, when the collet 1614 is moved downwardly within the bore 1630, the tapered head portion 1640 of the collet 1614 is able to expand and loosen its grip on the distal end of the tibial insert 1612. As such, the untightened, or downward position, the collet 1614 does not substantially interfere with the rotating motion of the tibial insert relative to the tray 1612.

Figure 49:
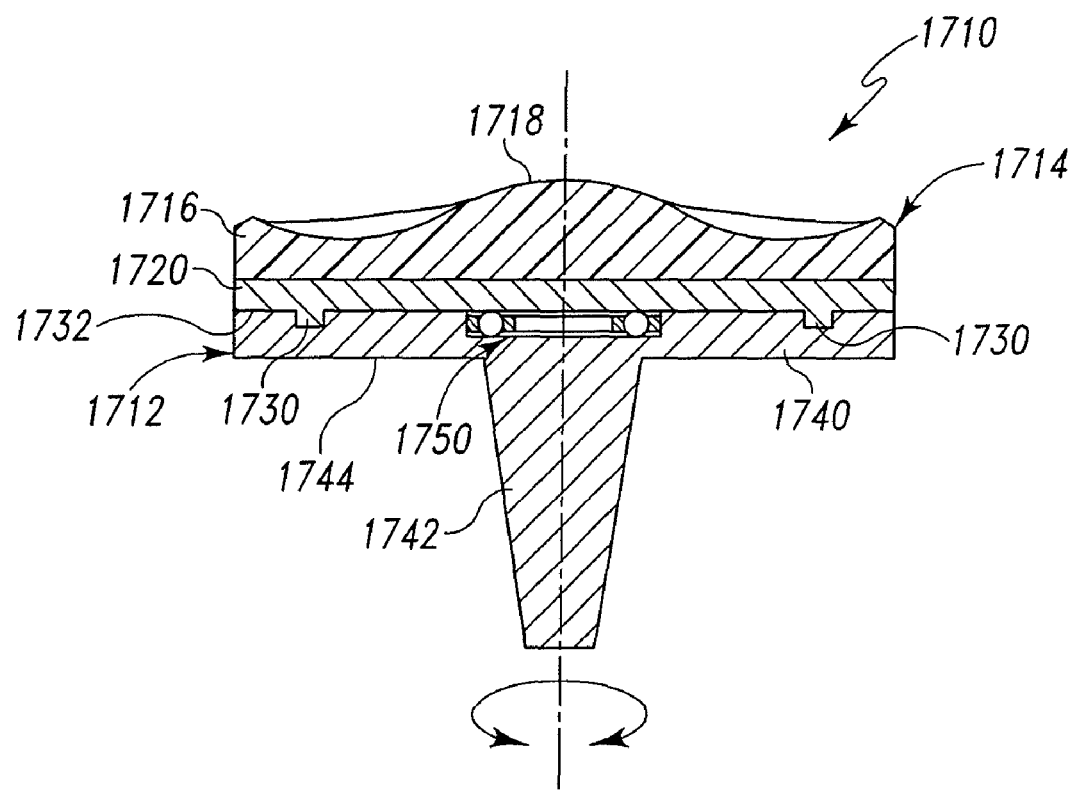
FIG. 49 is a sectional view of a tibial tray and a tibial insert coupled to the tray showing the tibial insert including an upper, polymer and a lower, metal base configured to be coupled to the metal tibial tray.
Figure 50:
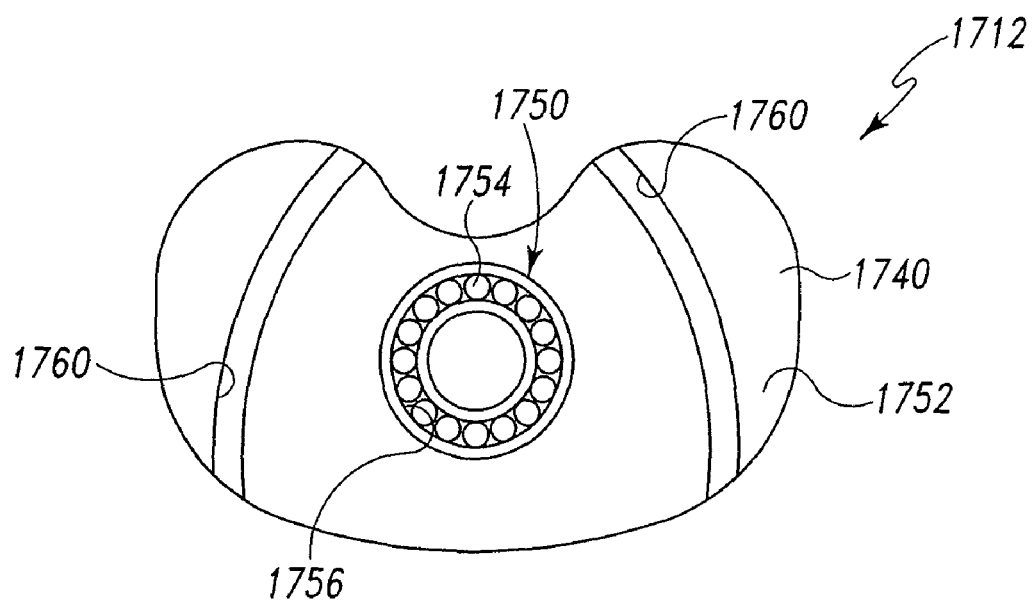
FIG. 50 is a top view of the tibial tray of FIG. 49 including a bearing system.

Looking now to FIGS. 49 and 50, a tibial assembly 1710 includes a tibial tray 1712 and a rotating tibial insert 1714. The rotating tibial insert 1714 includes a bearing portion 1716 defining an upper bearing surface 1718. Illustratively, the bearing portion 1716 is made of a polymer such as UHMWPE, for example. The tibial insert 1714 further includes a metal backing portion 1720 coupled to the bearing portion 1716 and includes a pair of rails 1730 extending downwardly from a bottom surface 1732 of the metal backing portion 1720.

The tibial tray 1712 includes a platform 1740 and a stem 1742 coupled to a bottom surface 1744 of the platform 1740. The platform 1740 further includes a roller bearing system 1750 incorporated into a top surface 1752 of the platform 1740. Illustratively, the roller bearing system 1750 includes a plurality of roller bearings 1754 set in a circular track 1756 coupled to the platform 1740. The platform 1740 further includes a pair of guide tracks 1760 formed to receive the downwardly-extending rails 1730 of the tibial insert 1714 therein. The roller bearings 1754 of the roller bearing system 1750 are metal and are adjacent to and engaged with the bottom surface 1732 of the metal backing portion 1720 of the tibial insert 1714. As such, the roller bearing system 1750 operates to decrease friction between the tibial insert 1714 and the tibial tray 1712 as the tibial insert 1714 is urged to rotate relative to the tibial tray 1714. The guide tracks 1760 and the rails 1730 cooperate to guide and constrain the rotational movement of the tibial insert 1714 relative to the tibial tray 1712.

Figure 51A:
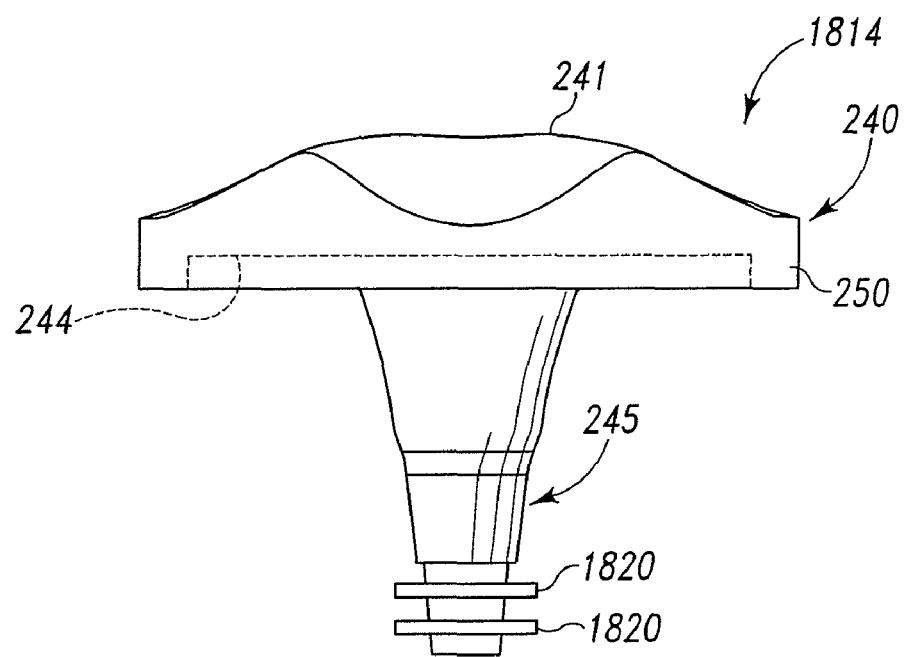
FIG. 51a is a side view of a tibial insert including a stem having flanges or pegs coupled thereto.
Figure 51B:
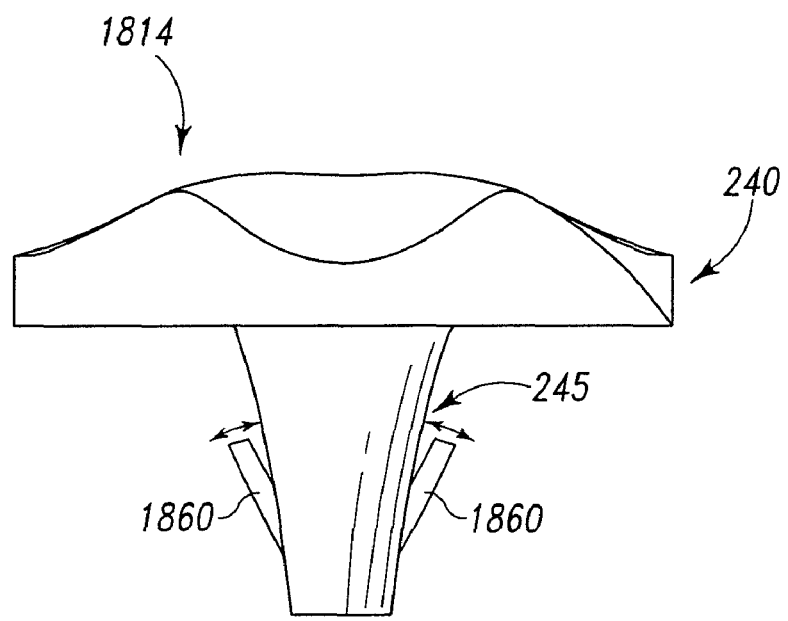
FIG. 51b is a side view of a tibial insert including a stem having flexible tabs coupled thereto.

Looking now to FIG. 51a, a fixed tibial insert 1814 for use with a tibial tray (not shown) is provided. The tibial insert 1814 is similar to the tibial insert 214 shown in FIG. 2. As such, like reference numerals have been used to denote like components. The tibial insert 1814 of FIG. 51a further includes flanges or pegs 1820 coupled to the distal end of the stem 245. The pegs 1820 of the tibial insert 1814 are flexible and may be snapped into corresponding annular grooves formed in the bore of the tibial tray (not shown) into which the stem 245 is received. The pegs 1820 aide in preventing lift-off of the tibial insert 1814 relative to the tibial tray. In an alternative embodiment, the stem 245 of the tibial insert 1814 may include flexible tabs 1860, as shown in FIG. 51b, which may be received within corresponding slots or an annular groove formed into the bore of the stem of a corresponding tibial tray in order to prevent lift-off of the insert relative to the tray.

Figure 52:
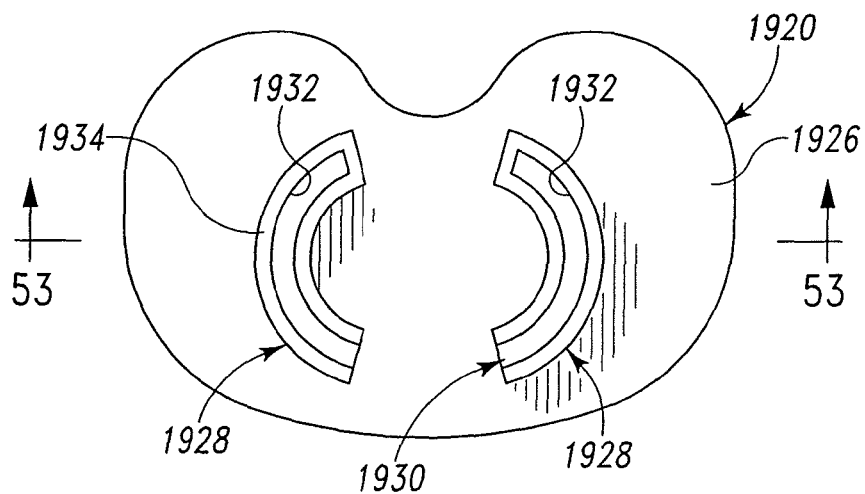
FIG. 52 is a bottom view of a platform component of a modular tibial tray including a pair of generally "C-shaped" guide tracks.
Figure 53:
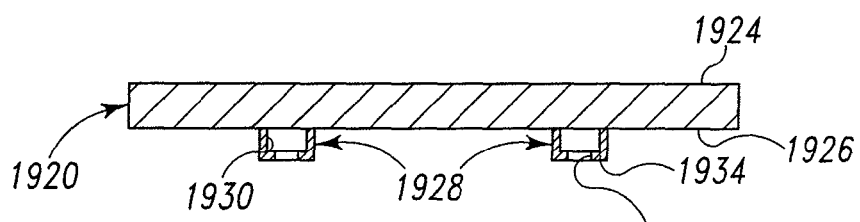
FIG. 53 is a sectional view taken along lines 53-53 of the platform component of FIG. 52.
Figure 54:
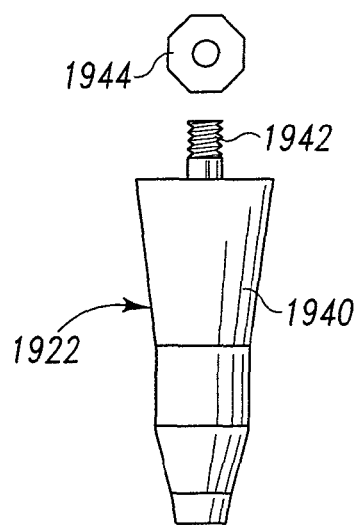
FIG. 54 is a side view of a stem component of the modular tibial tray including a threaded shaft and a locking bolt configured to be received within either one of the guide tracks of the platform component shown in FIGS. 52 and 53.

Looking now to FIGS. 52-54, a modular tibial tray is provided which includes a platform 1920, shown in FIGS. 52 and 53, and a stem 1922, shown in FIG. 54, which may be secured to the platform 1920 in a variety of positions. Looking first to FIGS. 52 and 53, the platform 1920 includes a top surface 1924, a bottom surface 1926, and a pair of generally C-shaped guide tracks 1928 coupled to the bottom surface 1926 of the platform 1920. The ends of each guide track 1928 are open to an inner channel or passageway 1930 of each track 1928. An opening or slot 1932 is formed in a bottom wall 1926 between two inner-extending lips of each guide track 1928 to provide communication with the inner passageway 1930. The stem 1922 includes a stem body 1940 and a mounting end having a threaded neck 1942 extending upwardly from the stem body 1940. A locking bolt 1944 of the stem 1922 is configured to be coupled to the threaded neck 1942.

In use, the locking bolt 1944 is coupled to the threaded neck 1942 and received through one of the ends of one of the guide tracks 1928 of the platform 1920 such that the neck 1942 of the stem 1922 is received through the slot 1934 of the particular guide track 1928 and the locking bolt 1944 is received within the channel 1930. The stem 1922 may then be moved along the chosen guide track 1928 to position the stem 1922 as desired by the surgeon or other technician.

Once the stem 1922 is properly positioned relative to the platform 1920, the locking bolt 1944 may be tightened further onto the neck 1942 of the stem 1922 to prevent relative movement between the stem 1922 and the platform 1920. In other words, the chosen guide track 1928 operates to capture the locking bolt 1944 therein and once the stem 1922 is in the desired position along the track 1928, the stem 1922 can be tightened into the locking bolt 1944 to fix the stem 1922 in place relative to the platform. Illustratively, therefore, the modular tibial tray shown in FIGS. 52 and 53 provides an offset stem 1922 which may be positioned off-center either medially or laterally on the platform 1920 and which may be positioned posteriorly or anteriorly along the particular offset guide track 1928.

Figure 55:
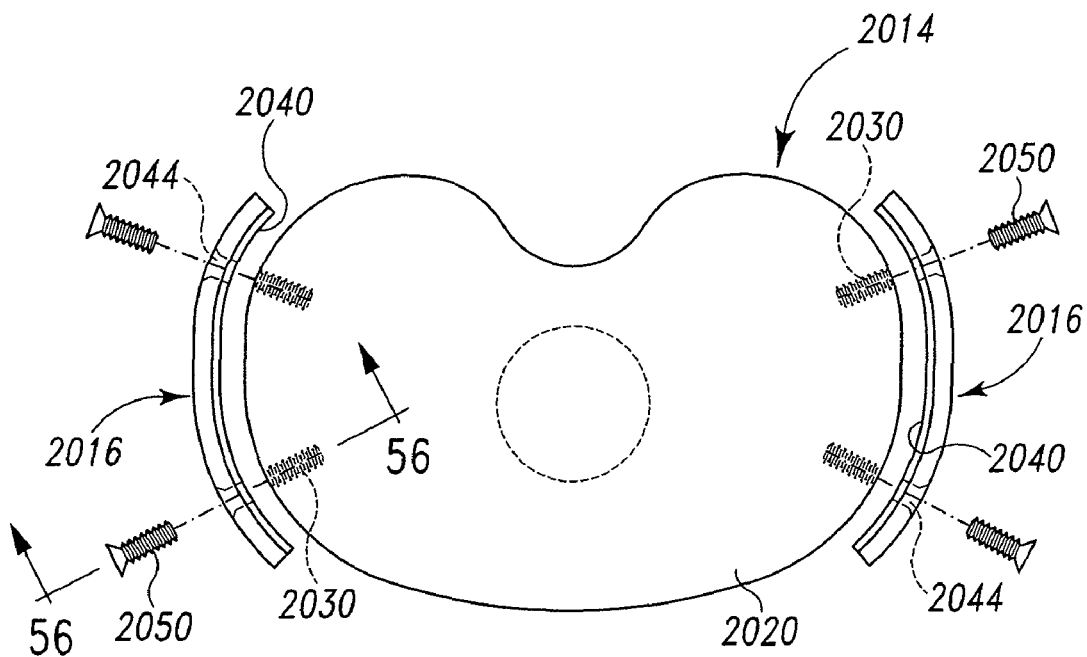
FIG. 55 is a top view of a tibial assembly including a tibial insert, a tibial tray, and a pair of metal clamps configured to be coupled to the tibial insert and the tibial tray in order to prevent relative movement between the tibial insert and the tibial tray.
Figure 56:
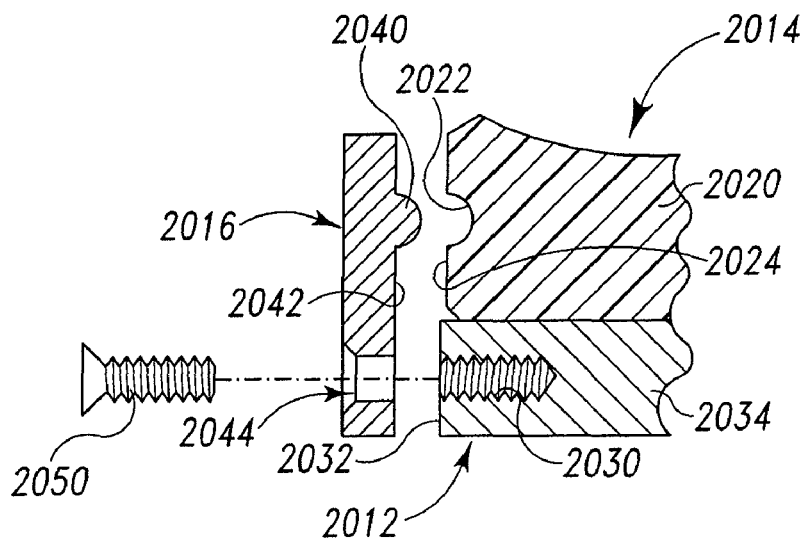
FIG. 56 is a sectional view taken along line 56-56 of a portion of the tibial assembly of FIG. 55 showing one of the metal clamps including a tab to be received within a peripheral groove of the tibial insert and a screw to be received within the tibial tray in order to couple the clamp to the tibial insert and the tibial tray and prevent relative movement therebetween.

Looking now to FIGS. 55 and 56, a prosthetic knee assembly includes a tibial tray 2012, a tibial insert 2014, and a pair of clamps 2016 configured to be used with the tibial insert 2014 and the tibial tray 2012 to provide a fixed tibial assembly. The tibial insert 2014 includes a platform 2020 having an annular groove 2022 formed in an outer, peripheral surface 2024, as shown in FIG. 56. The tibial tray 2012 includes four threaded bores 2030 formed into an outer, peripheral surface 2032 of a platform 2034 of the tray 2012. Each clamp 2016 is generally C-shaped to mate with the medial and lateral outer surfaces 2024, 2032 of each of the tibial insert 2014 and the tibial tray 2012. Each clamp 2016 further includes a rim or lip 2040 protruding from an inner surface 2042 of each clamp 2016 as well as a pair of countersunk bores 2044 configured to receive a threaded screw 2050 therethrough.

In a first, fixed configuration, the clamps are positioned adjacent the outer, peripheral walls 2024, 2032 of the tibial insert 2014 and the tibial tray 2012 such that the rim 2040 of each clamp 2016 is received within the groove 2022 of the tibial insert 2014. Further, the bores 2044 of each clamp 2016 are aligned with corresponding bores 2030 of the tibial tray 2014. One of the threaded screws 2050 is received through each of the countersunk bores 2044 of the clamps 2016 and is screwed into the respective threaded bore 2030 of the tibial tray 2014. As such, each clamp 2016 is coupled to the tibial tray 2012 and the tibial insert 2014 in order to prevent rotational movement of the tibial insert 2014 relative to the tibial tray 2012. The rim 2040 of each clamp 2016 and the groove 2022 of the tibial insert 2014 cooperate to prevent lift-off of the tibial insert 2014 relative to the tibial tray 2012. Illustratively, each clamp 2016 may be metal. In a second, rotating configuration, the clamps 2016 are not used and the tibial insert 2014 is able to rotate relative to the tibial tray 2012 to provide a rotating tibial assembly.

Figure 57:
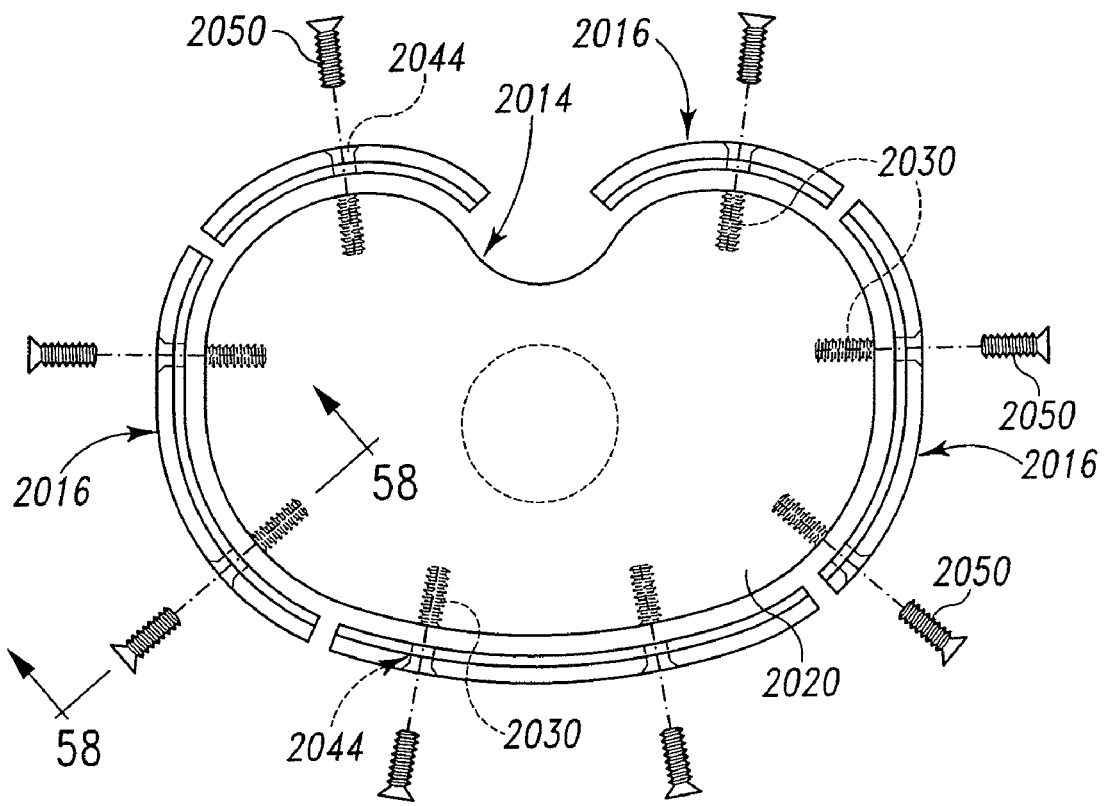
FIG. 57 is a top view of a tibial assembly similar to the tibial assembly shown in FIGS. 55 and 56 including five separate metal clamps configured to be coupled to the tibial insert and the tibial tray of the tibial assembly in order to prevent relative movement between the tibial insert and the tibial tray.
Figure 58:
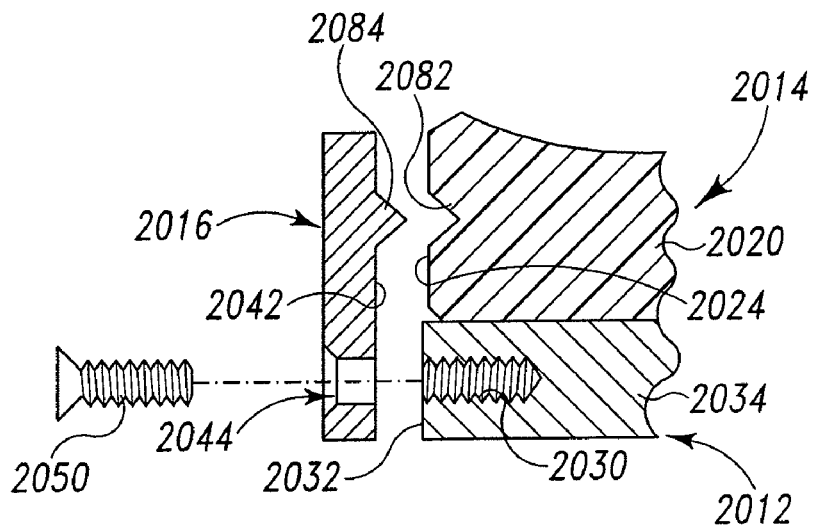
FIG. 58 is a sectional view taken along line 58-58 of a portion of the tibial assembly of FIG. 57.

Looking now to FIGS. 57 and 58, another prosthetic knee assembly is provided. The prosthetic knee assembly of FIGS. 57 and 58 is similar to the prosthetic knee assembly of FIGS. 55 and 56. As such, like reference numerals are used to denote like components. In general, the prosthetic knee assembly of FIGS. 57 and 58 provides multiple clamps 2016 to surround and capture a majority of the peripheral surfaces 2024, 2032 of each of the tibial insert 2014 and the tibial tray 2012 in order to prevent rotational movement of the tibial insert 2014 relative to the tibial tray 2012. Further, the tibial insert 2014 includes a V-shaped groove 2082 formed in the outer surface 2024 of the platform 2020 and each clamp 2016 includes a coordinating V-shaped rim or tab 2084 to be received within the V-shaped groove 2082 of the insert 2014. The coordinating V-shape designs of both the tab 2084 and the groove 2082 may operate to provide downward pressure against the tibial tray 2012 to further aide in preventing lift-off and micromotion of the tibial insert 2014 relative to the tray 2012.

Figure 59:
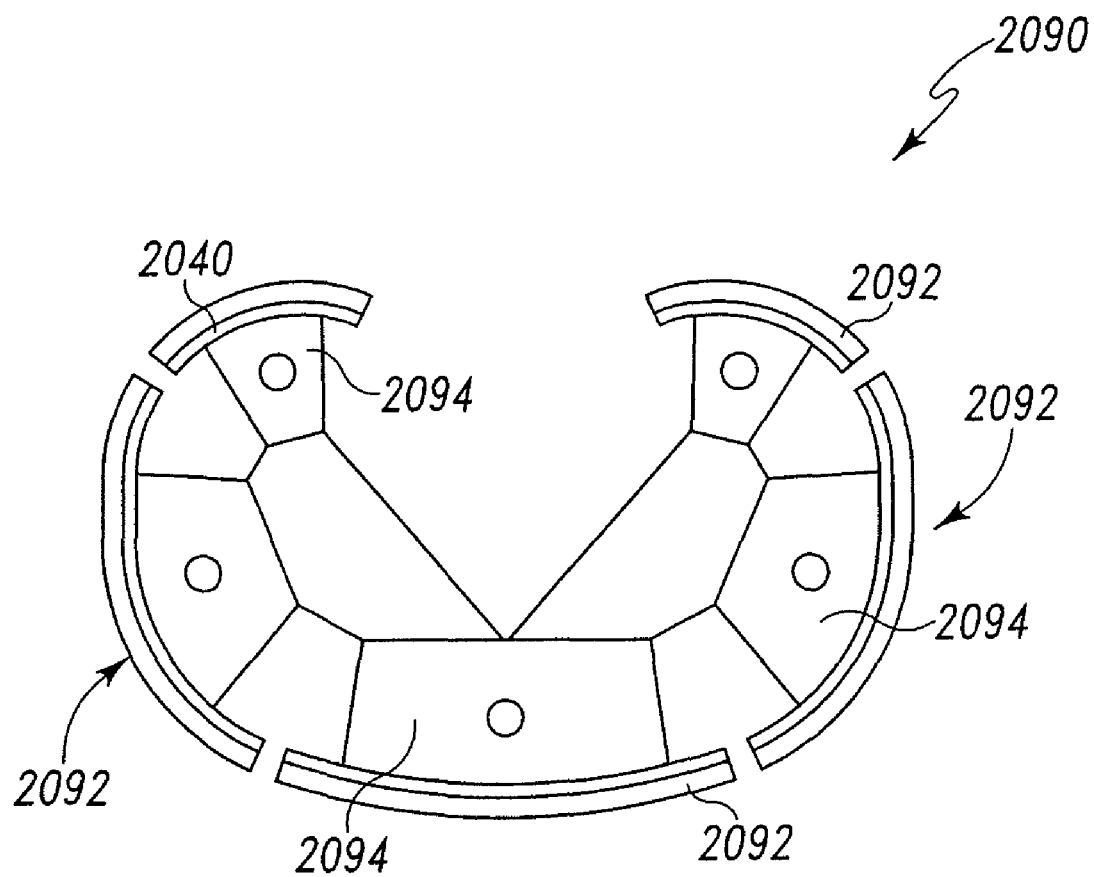
FIG. 59 is a top view of a spring-loaded clamp assembly configured to be coupled to a tibial insert and a tibial tray in order to prevent relative movement between the tibial bearing and the tibial tray.

While the clamps 216 shown in FIGS. 55-58 are modular, a non-modular clamp assembly, such as the spring-loaded clamp assembly 2090 shown in FIG. 59, may be provided. Such a non-modular clamp assembly eliminates the need for screws 2050 thus operating to reduce such additional failure mechanisms. Accordingly, the spring-loaded clamp assembly 2090 includes various spring-loaded clamp components 2092 coupled together by corresponding body portions 2094. The clamp assembly 2090 is configured to surround the platform of both a tibial insert and a tibial tray, such as the tibial insert 2014 and the tibial tray 2012 shown in FIGS. 55-58, and is somewhat flexible to allow the insert to snap into place.

Figure 60:
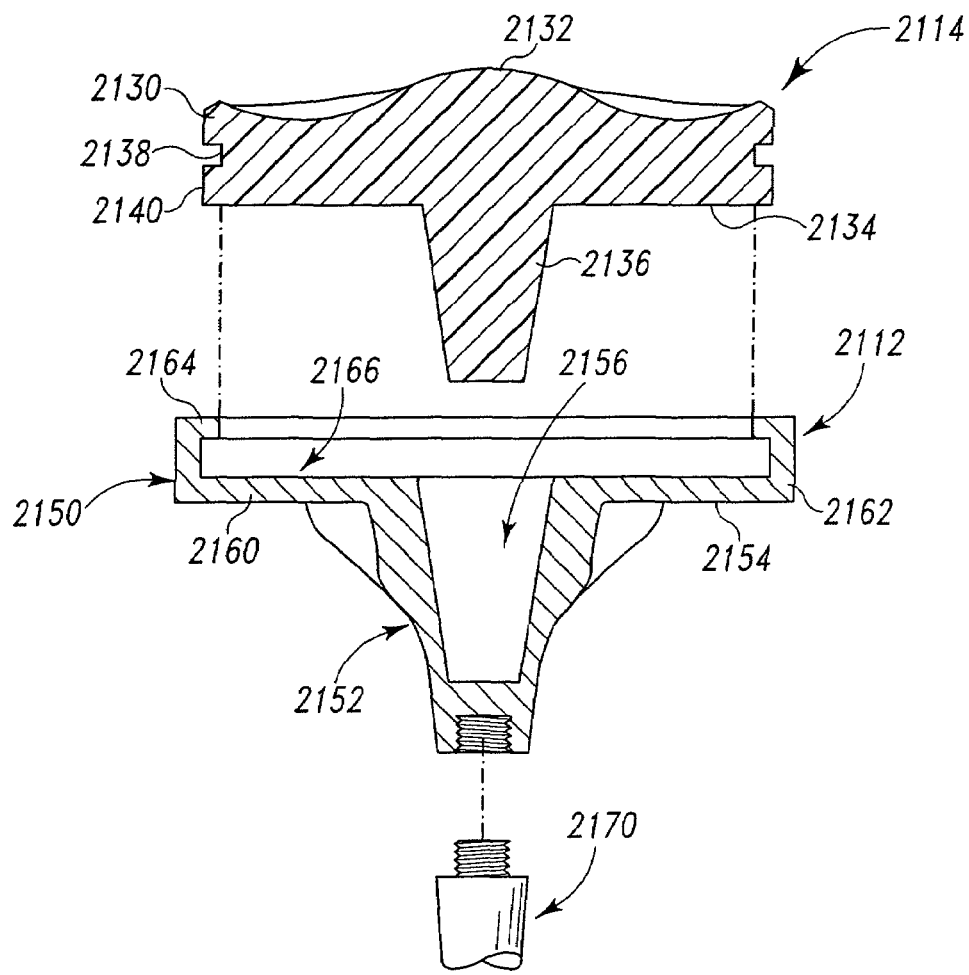
FIG. 60 is a sectional, exploded view of a fixed tibial assembly including a tibial insert and a modular tibial tray including an extendable stem component.
Figure 61:
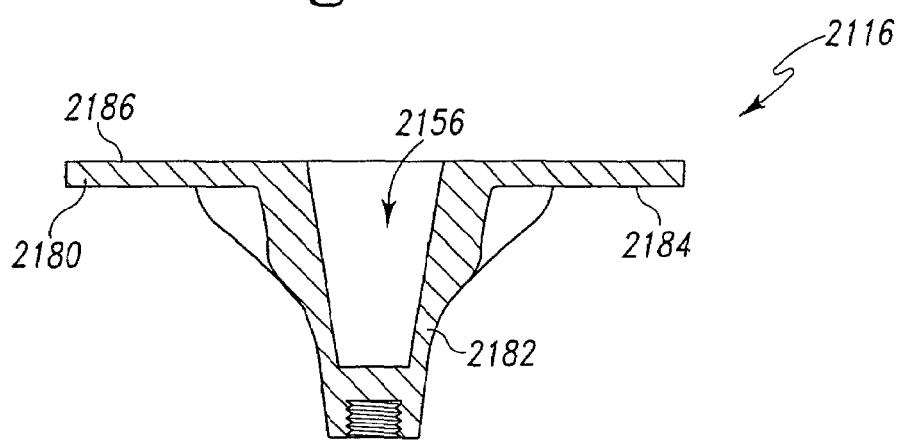
FIG. 61 is a sectional view of a modular tibial tray configured for use with the tibial insert of FIG. 60 in order to provide a rotating tibial assembly.

Looking now to FIGS. 60 and 61, another prosthetic knee system includes a tibial insert 2114 (shown in FIG. 60), a fixed tibial tray 2112 (shown in FIG. 60), and a rotating tibial tray 2116 (shown in FIG. 61). Illustratively, the tibial insert 2114 may be used with the fixed tibial tray 2112 to provide a fixed tibial assembly or with the rotating tibial tray 2116 to provide a rotating tibial assembly. The tibial insert 2114 includes a platform 2130 having an upper bearing surface 2132 and a bottom surface 2134. A stem 2136 is coupled to the bottom surface 2134 and a slot 2138 of the platform 2130 is formed within an outer peripheral or side surface 2140 of the platform 2130, as shown in FIG. 60. The slot 2138 defines a closed path in the side surface 2140.

The fixed tibial tray 2112 includes a platform 2150, a stem 2152 coupled to a bottom surface 2154 of the platform 2150 and a cavity or bore 2156 through the platform 2150 and into the stem 2152 to receive the stem 2136 of the tibial insert 2114 therein. The platform 2150 includes a bottom wall 2160, a peripheral rim 2162 extending upwardly from the bottom wall 2160, and an inner lip 2164 extending inwardly from a proximal end of the peripheral rim 2162. The bottom wall 2160, rim 2162, and inner lip 2164 cooperate to define a platform-receiving cavity or recess 2166 of the tibial tray 2112 for receiving at least a portion of the platform 2130 of the tibial insert 2114 therein. Illustratively, a stem extender 2170 may be coupled to a distal end of the stem 2152 to extend the length of the stem if so desired by the surgeon.

In use, the tibial insert 2114 is snapped into the tibial tray 2112 such that the stem 2136 of the insert 2114 is received within the bore 2156 of the tray 2112 and the inner lip 2164 of the tray 2112 is received within the slot 2138 of the insert 2114. Illustratively, the rim 2162 and inner lip 2164 of the tray 2112 may be flexible in order to allow the platform 2130 of the insert 2114 to be snapped into the platform-receiving cavity 2166 of the tray 2112. Once the tibial insert 2114 is coupled to the tray 2112, the tibial insert 2114 is fixed relative to the tray 2112. In other words, the rim 2162 of the tray 2112 operates to prevent the insert 2114 from rotating relative to the tray 2112 while the inner lip 2164 of the tray 2112 further operates to prevent lift-off of the insert 2114 relative to the tray 2112 and any micromotion between the two components.

Looking now to FIG. 61, the rotating tibial tray 2116 simply includes a platform 2180 and a stem 2182 coupled to a bottom surface 2184 of the platform 2180. The stem 2136 of the tibial insert 2114 may be received within the bore 2156 of the tray 2116 such that the bottom surface 2134 of the platform 2130 of the insert 2114 is engaged with the top surface 2186 of the platform 2180 of the tray 2116. In this configuration, the tibial insert 2114 is able to rotate relative to the tray 2116 to provide a rotating tibial assembly.

Looking now to FIGS. 62-66, another prosthetic knee system includes a tibial tray 2122 (shown in FIGS. 62, 63, 65, and 66), a fixed tibial insert 2214 (shown in FIGS. 64-66), and a rotating tibial insert (not shown) similar to the rotating tibial insert shown in FIGS. 2, 9, and/or 14, for example. Illustratively, the tibial tray 2212 and the fixed tibial insert 2214 cooperate to define a fixed tibial assembly wherein the tibial insert 2214 is not rotatable relative to the tibial tray 2212. Further, the same tibial tray 2212 and the rotating tibial insert cooperate to define a rotating knee assembly wherein the tibial insert is able to rotate relative to the tibial tray 2212.

As shown in FIGS. 62 and 63, the tibial tray 2212 includes a platform 2220, a stem 2222 coupled to a bottom surface 2224 of the platform 2220, and a bore 2230 formed through the platform 2220 and into the stem 2222. Illustratively, an opening 2240 formed in the top surface 2242 of the platform 2220 and in communication with the bore 2230 is shaped to receive a coordinating hub 2250 (shown in FIG. 64) of the fixed tibial insert 2214. In particular, the opening 2240 includes two access openings 2241. Further, two undercut recesses 2252 formed in the platform 2220 and the stem 2222 are each communication with the opening 2240 and with the bore 2230. The undercut recesses 2252 are each configured to receive a portion of the hub 2250 when the fixed tibial insert 2214 is in a locked position relative to the tibial tray 2212. As shown in FIG. 63, the recesses 2252 are each tapered downwardly within the bore 2230. Illustratively, the tapered angle 2256 may be between 1-89 degrees and is preferably approximately 3 degrees.

Looking now to FIG. 64, the fixed tibial insert 2214 includes a platform 2260 having an upper bearing surface 2262 and a bottom surface 2264. The hub 2250 is coupled to the bottom surface 2264 and configured to be received within the opening 2240 and the undercut recesses 2252 of the tibial tray 2212. Illustratively, the hub 2250 includes a center portion 2266 and two tabs 2268 extending outwardly therefrom. Further illustratively, the shape of the hub 2250 when viewed from the bottom is generally the same as the shape of the opening 2240 of the tibial tray 2212.

In use, the fixed tibial insert 2214 may be coupled to the tibial tray 2212 to define a fixed tibial assembly. Illustratively, the hub 2250 of the fixed insert 2214 is received into the opening 2240 of the tray 2212 such that the tabs 2268 are received in the access openings 2241. The fixed tibial insert 2214 is then rotated clockwise toward a locked position such that the tabs 2268 of the hub 2250 are received within the respective recesses 2252 of the tibial tray 2212. The taper of the undercut recesses 2252 provides for a snug fit between the tibial insert 2214 and the tray 2212. As such, in this locked position, the fixed tibial insert 2214 is not configured to rotate or translate relative to the tibial tray 2212. Of course, additional locking mechanisms may be used to further fix the tibial insert relative to the tray in order to prevent lift-off, rotation, and/or micromotion as is discussed throughout this disclosure.

As noted above, a rotating tibial insert such as the tibial insert shown in FIGS. 2, 9, and/or 14, for example, may be provided for use with the tibial tray 2212 such that the rotating tibial insert, when coupled to the tray 2212, is able to rotate relative to the tray.

Figure 67:
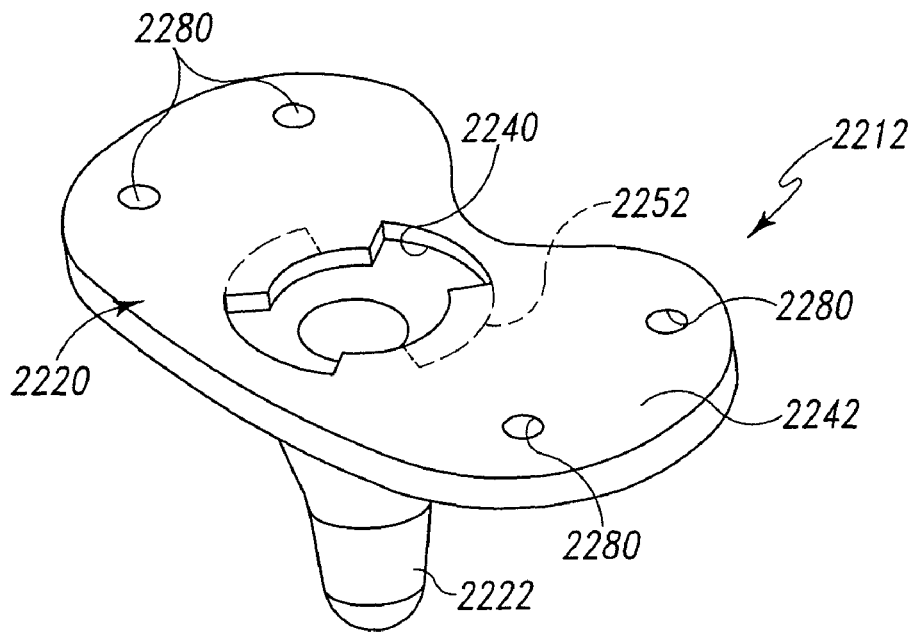
FIG. 67 is a perspective view of another tibial tray similar to the tibial tray shown in FIG. 62.
Figure 68:
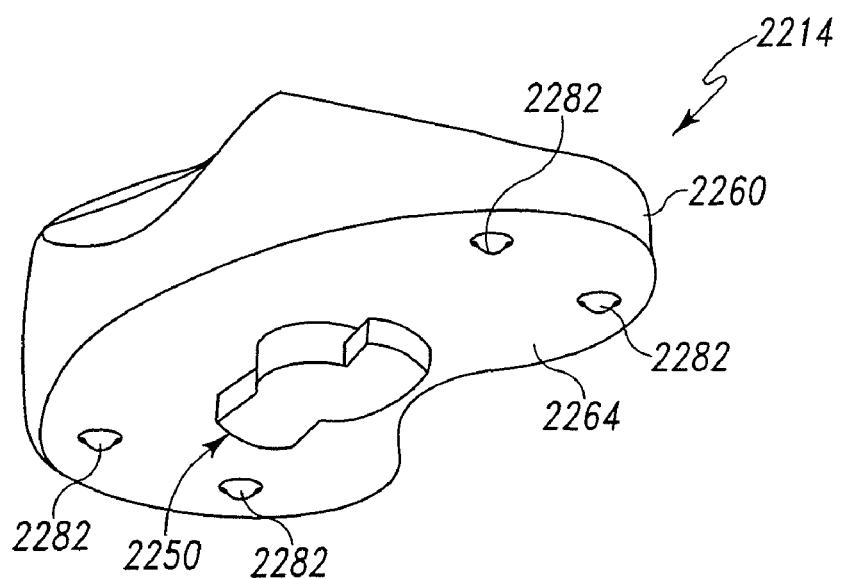
FIG. 68 is a perspective view of another tibial insert similar to the tibial insert shown in FIG. 64.

Looking now to FIGS. 67 and 68, a fixed knee assembly similar to the fixed knee assembly shown in FIGS. 62-66 is shown. As such, like reference numerals are used to denote like components. The tibial tray 2212 shown in FIG. 67 includes recesses 2280 formed in the top surface 2242 of the platform 2220. Specifically, two recesses 2280 are provided on either side of the opening 2240.

The fixed tibial insert 2214 includes protrusions 2282 extending downwardly from the bottom surface 2264 of the platform 2260. Specifically, two protrusions 2282 are provided on either side of the hub 2250 which correspond to the two recesses 2280 located on either side of the opening 2240 of the tray 2212. As such, the protrusions 2282 are received within the recesses 2280 when the fixed tibial insert 2214 is in the locked position relative to the tibial tray 2212 in order to further prevent rotation of the tibial insert 2214 relative to the tray 2212 as well as micromotion between the two components. While four protrusions 2282 and four recesses 2280 are provided, it is within the scope of this disclosure to provide any number of corresponding protrusions and recesses on the fixed tibial insert 2214 and the tibial tray 2212.

Figure 69:
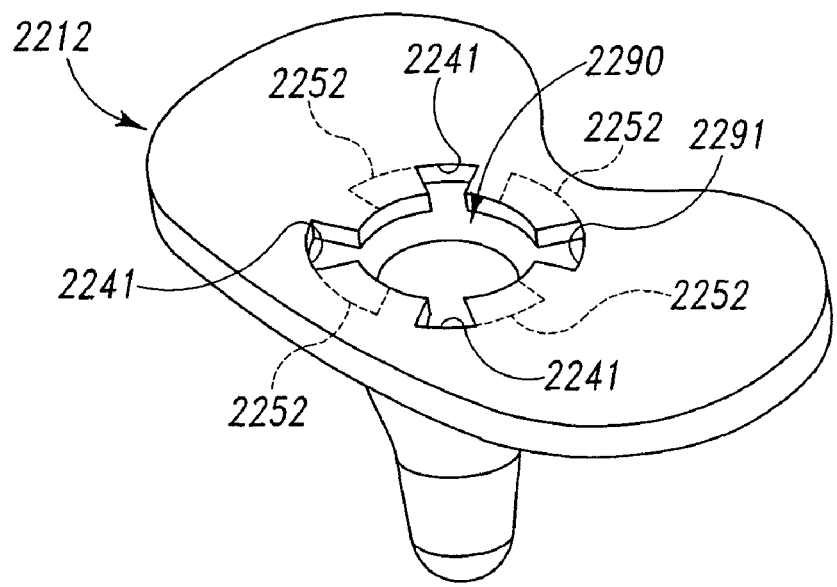
FIG. 69 is a perspective view of another tibial tray.
Figure 70:
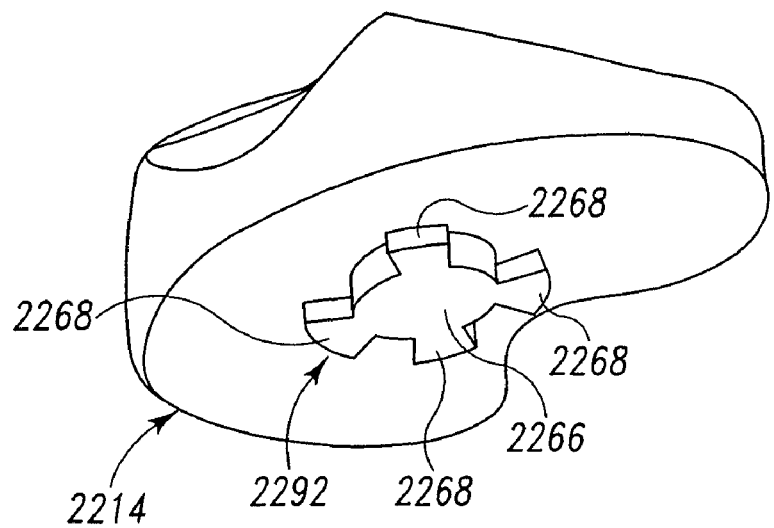
FIG. 70 is a perspective view of another tibial insert configured to be used with the tibial tray of FIG. 69.

Looking now to FIGS. 69 and 70, another fixed knee assembly similar to the fixed knee assembly shown in FIGS. 62-66 is provided. As such, like reference numerals are used to denote like component. As shown in FIG. 69, an opening 2290 of the tibial tray 2212 includes four access openings 2041 and four corresponding undercut recesses 2252. Further, a hub 2292 of the fixed tibial insert 2214 shown in FIG. 70 includes four tabs 2268 extending outwardly from the center portion 2266. Similar to the undercut recesses 2252 discussed above, the undercut recesses 2252 shown in FIG. 69 are tapered such that the hub 2292 of the fixed tibial insert 2214 is inserted into the opening 2290 of the tibial tray 2212 and is illustratively rotated counterclockwise such that the tabs 2268 of the hub 2292 are each received within a respective undercut recess 2252 of the tray 2212 in order to lock the fixed tibial insert 2214 to the tray 2212.

Figure 71:
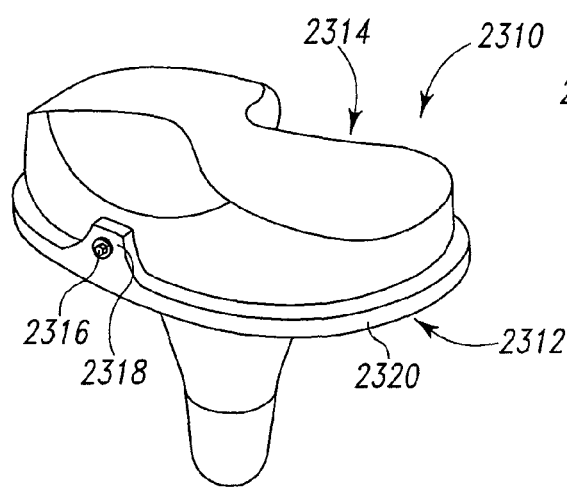
FIG. 71 is a perspective view of a prosthetic knee assembly including a tibial insert, a tibial tray, and a locking pin.
Figure 72:
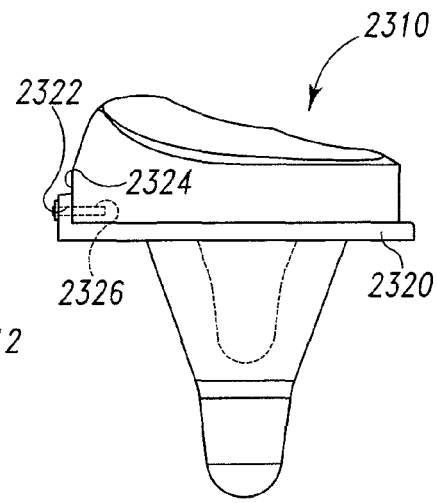
FIG. 72 is a side view of the prosthetic knee assembly of FIG. 71.

Looking now to FIGS. 71 and 72, another fixed tibial assembly 2310 includes a tibial tray 2312 and a tibial insert 2314 coupled to the tray 2312. A locking pin 2316 of the assembly couples the tibial insert 2314 to the tray 2312 to prevent rotational movement of the insert 2314 relative to the tray 2312. Illustratively, the tibial tray 2312 includes an upwardly-extending flange 2318 coupled to the platform 2320 of the tray 2312. The flange 2318 includes an aperture 2322 formed therethrough while an anterior surface 2324 of the insert 2314 includes a bore 2326 formed therein. The bore 2326 is illustratively aligned with the aperture 2322 of the flange 2318 when the tibial insert 2314 is received on the platform 2320 of the tray 2312. The locking pin 2316 is received through the aperture 2322 of the tray 2312 and into the bore 2326 of the insert 2314 in order to prevent rotational movement of the insert 2314 relative to the tray 2312. The aperture 2322 and/or the bore 2326 may be threaded such that a threaded locking pin may be screwed into the aperture 2322 and bore 2326 to more securely retain the pin therein. Although the tibial assembly 2310 is shown and described as a fixed tibial assembly, it should be understood that the tibial insert 2314 may be able to rotate relative to the tray 2312 with the removal of the locking pin 2316. In other words, the tibial insert 2314 and the tray 2312 may cooperate to provide a rotating tibial assembly as well.

Figure 73:
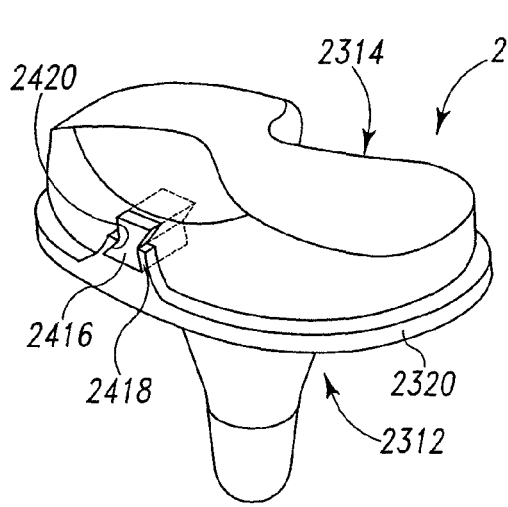
FIG. 73 is a perspective view of another prosthetic knee assembly including a tibial insert, a tibial tray, and a locking insert.
Figure 74:
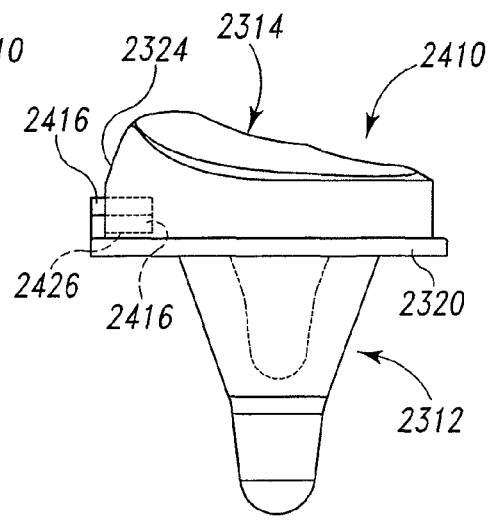
FIG. 74 is a side view of the prosthetic knee assembly of FIG. 73.

Looking now to FIGS. 73 and 74, another fixed knee assembly 2410 similar to the fixed knee assembly 2314 of FIGS. 71 and 72 is provided. As such, like reference numerals are used to denote like components. The assembly 2140 of FIGS. 73 and 74 includes a locking pin 2416 which is generally hourglass shaped and is configured to be received through a coordinating hourglass shaped bore 2426 formed in the anterior surface 2324 of the tibial insert 2314. Illustratively, the flange 2418 of the tibial tray 2312 includes a generally trapezoidal shaped cutout portion 2420 to receive the bottom half of the locking pin 2416 therein in order to fixedly coupled the tibial tray 2312 and the tibial insert 2314 together to prevent rotation of the tibial insert 2314 relative to the tibial tray 2312. Although the tibial assembly 2410 is shown and described as a fixed tibial assembly, it should be understood that the tibial insert 2414 may be able to rotate relative to the tray 2412 with the removal of the locking pin 2416. In other words, the tibial insert 2414 and the tray 2412 may cooperate to provide a rotating tibial assembly as well.

Figure 75:
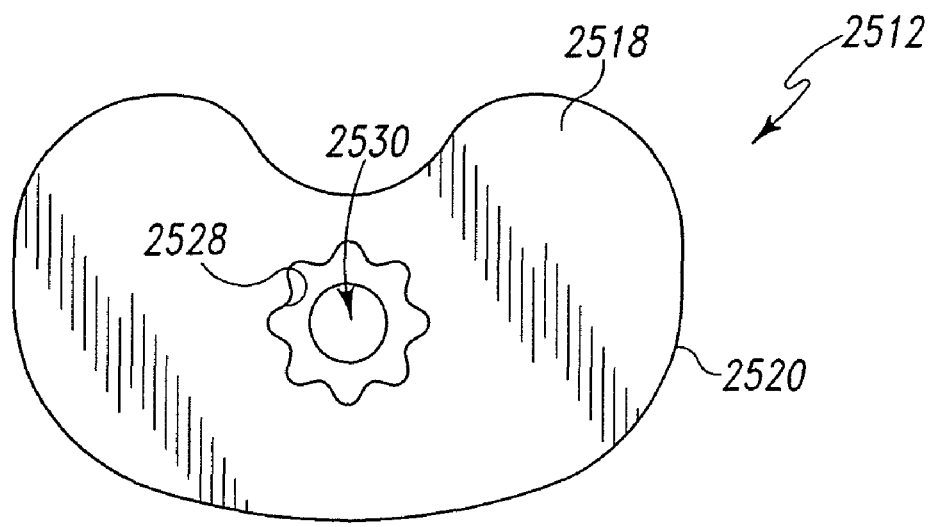
FIG. 75 is a top view of another tibial tray showing an irregularly shaped cutout formed in the platform around the bore of the tibial tray.
Figure 76:
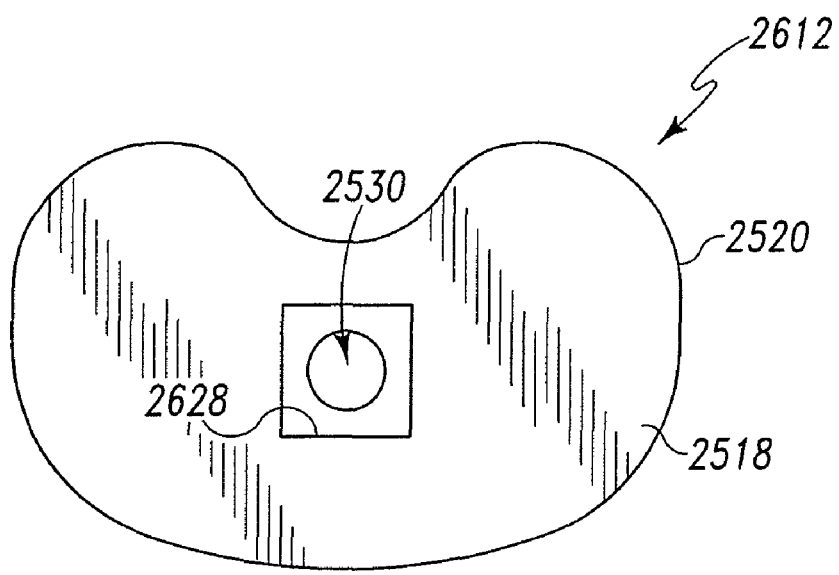
FIG. 76 is a top view of another tibial tray showing a rectangular-shaped cutout formed in the platform around the bore of the tibial tray.
Figure 77:
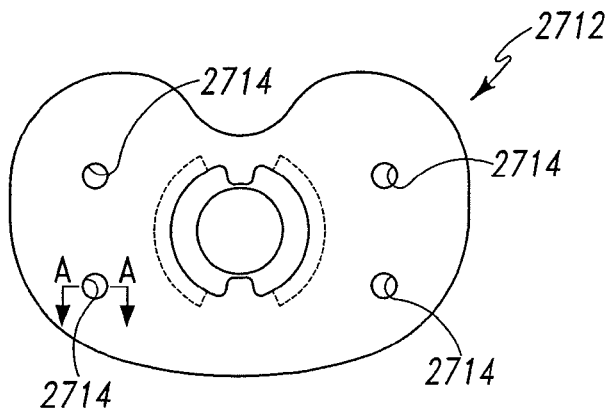
FIG. 77 is a top view of another tibial tray showing a plurality of cutout portions each configured to receive a mating tab from a corresponding tibial insert (not shown)

Looking now to FIGS. 75 and 76, illustrative trays 2512, 2612 each include a keyed recess or opening formed in the platform 2520 of the tray 2512, 2612 in order to receive a coordinating hub of a similar shape extending downwardly from the platform of a fixed tibial insert (not shown) in order to prevent rotational motion of such tibial insert with respect to the trays 2512, 2612 shown. For example, the keyed opening 2528 of the tibial tray 2512 of FIG. 75 is positioned around the bore 2530 of the tray 2512 and is irregularly shaped. The keyed opening of the tibial tray 2612 shown in FIG. 76, on the other hand, is rectangularly shaped. While such shapes are provided to receive a similarly-shaped hub of a fixed tibial insert in order to prevent rotation of the tibial insert with respect to the tray, it is within the scope of this disclosure for the keyed opening to be provided in any suitable non-circular shape such as triangle, oval, or square-shaped, for example. Further, while the keyed opening 2528, 2628 of the trays 2512, 2612 shown in FIGS. 75 and 76 are located around the bore 2530 of each tray 2512, 2612, similar openings may be provided within other portions of the platform 2518 of each tray 2512, 2612, as is shown in FIGS. 77-83 discussed below.

Looking now to FIGS. 77-83, illustrative trays 2712, 2812, 2912, 3012 each include various cutout portions, slots, or bores formed therein. For example, the cutout portions shown in FIG. 77 include four bores 2714 formed within the top surface of the tray 2712 while the cutout portions shown in FIG. 78 include four slots or elongated opening 2814 formed within the top surface of the tray 2812. Similarly, the cutout portions 2914 shown in FIG. 79 include four elongated opening interconnected with the recessed portions 34, similar to the recessed portions 34 shown in FIGS. 1 and 2) of the tray 2912 while the cutout portions shown in FIG. 80 include two curved, elongated openings 3014 independent from the recessed portions 34 of the tray 3012.

Figure 81:
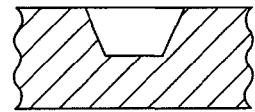
FIG. 81 is an enlarged sectional view of an exemplary cross-sectional shape of any of the openings of FIGS. 77-80.
Figure 78:
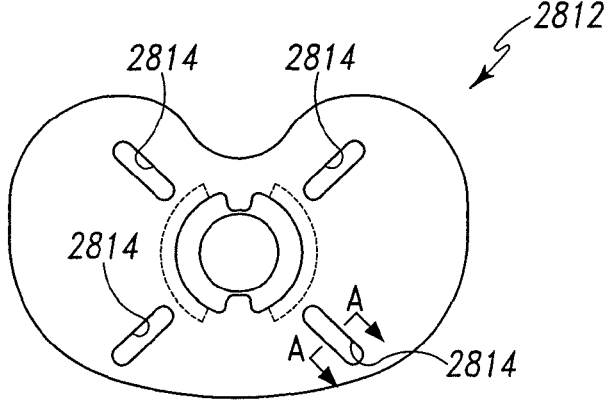
FIG. 78 is a top view of another tibial tray showing a plurality of elongated openings.
Figure 82:
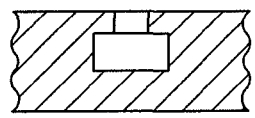
FIG. 82 is an enlarged sectional view of an exemplary cross-sectional shape of any of the openings of FIGS. 77-80.
Figure 83:
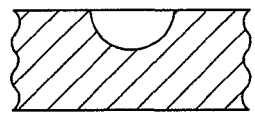
FIG. 83 is an enlarged sectional view of an exemplary cross-sectional shape of any of the openings of FIGS. 77-80.
Figure 79:
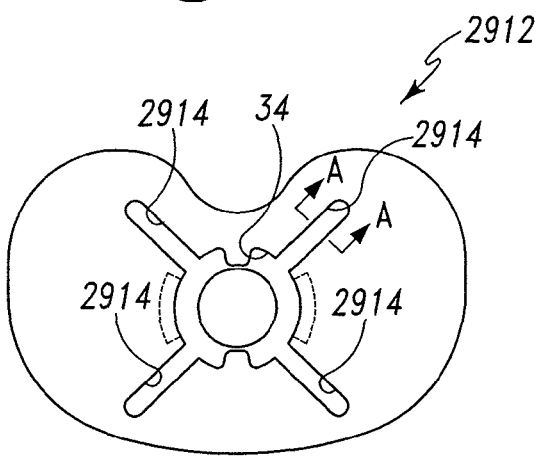
FIG. 79 is a top view of yet another tibial tray showing a plurality of interconnected openings.
Figure 80:
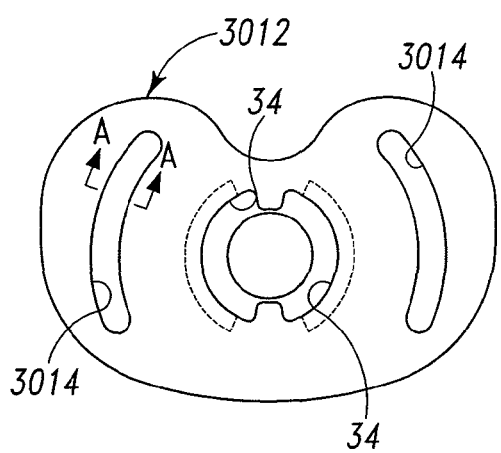
FIG. 80 is a top view of another tibial tray showing a plurality of curved openings.

Looking specifically now to FIGS. 81-83, illustrative sectional views of the elongated openings 2714, 2814, 2914, 3014 shown in FIGS. 77-80 are provided. In other words, each of the elongated openings 2714, 2814, 2914, 3014 may be formed to define any one of the cross-sectional profiles shown in FIGS. 81-83. For example, as shown in FIG. 81, the cross-section of any one of the elongated openings 2714, 2814, 2914, 3014 may tapered or trapezoidal in shape while the cross-section of any one of the cutout portions 2714, 2814, 2914, 3014 may be generally "T-shaped," as shown in FIG. 82, for example. Finally, the cross-section of any one of the cutout portions 2714, 2814, 2914, 3014 may simply be rounded, as shown in FIG. 83, and may illustratively be semi-circular. As noted above, a fixed tibial insert (not shown) may include coordinating tabs of similar shape extending downwardly from the bottom surface of the platform of such tibial insert. Such protrusions are received within the elongated openings in order to prevent rotational movement of the tibial insert relative to the particular tibial tray with which it is coupled. Such protrusions further operate to reduce or minimize any micro-motion between the two components.

Figure 84:
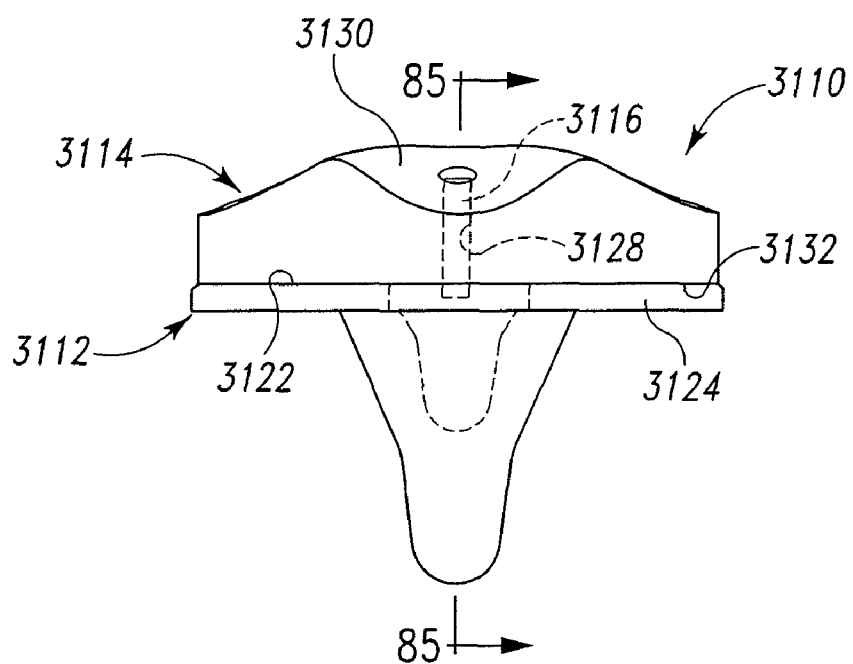
FIG. 84 is a front view of a fixed tibial assembly including a tibial tray, a tibial insert, and a locking pin.
Figure 85:
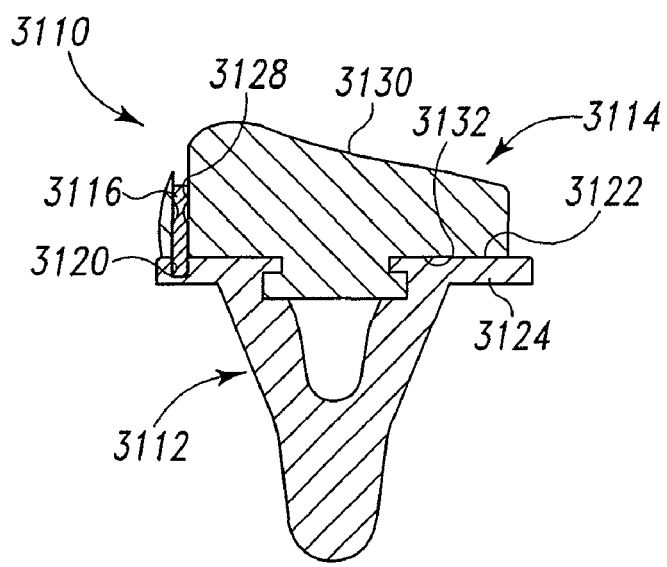
FIG. 85 is a sectional view of the fixed tibial assembly shown in FIG. 84.

Looking now to FIGS. 84 and 85, another knee assembly 3110 includes a tibial tray 3112 and a tibial insert 3114 coupled to the tray 3112. A locking pin 3116 of the assembly couples the tibial insert 3114 to the tray 3112 to prevent rotational movement of the insert 3114 relative to the tray 3112. Illustratively, the tibial tray 3112 includes a bore 3120 formed in a top surface 3122 of the platform 3124 of the tray 3112 while the tibial insert 3114 includes a through-hole 3128 extending between the upper bearing surface 3130 of the insert 3114 and the bottom surface 3132 of the platform 3134 of the insert 3114. Illustratively, the through-hole 3128 is positioned anteriorly within the insert 3114, as shown in FIG. 85.

When the tibial insert 3114 is received on the platform 3124 of the tray 3112, the hole 3128 of the insert 3114 and the bore 3120 of the tray 3112 are aligned. A locking pin 3140 of the assembly 3110 is received within the hole 3128 and the bore 3120 of the respective tibial tray 3114 and insert 3112 in order to prevent rotational movement of the tibial tray 3114 relative to the insert 3112. Although the tibial assembly 3110 is shown and described as a fixed tibial assembly, it should be understood that the tibial insert 3114 may be able to rotate relative to the tray 3112 with the removal of the locking pin 3116. In other words, the tibial insert 3114 and the tray 3112 may cooperate to provide a rotating tibial assembly as well.

Figure 89:
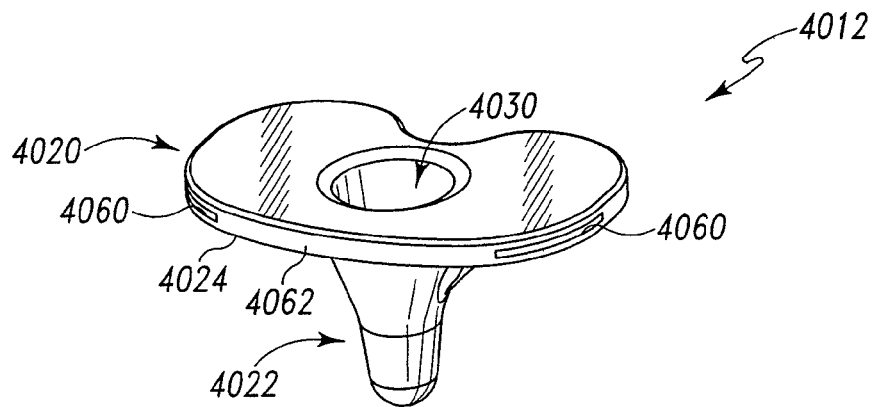
FIG. 89 is a perspective view of another embodiment of a tibial tray.
Figure 90:
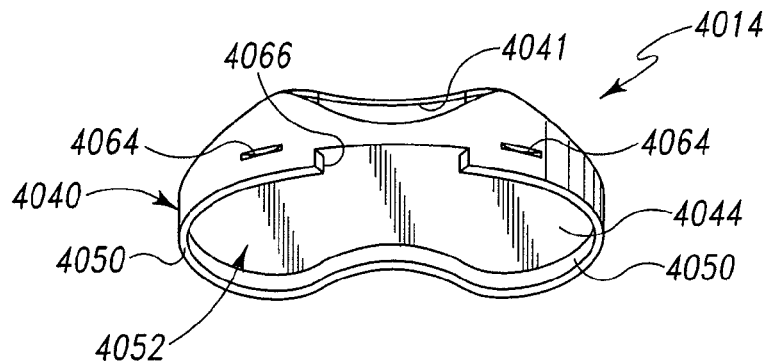
FIG. 90 is a perspective view of a non-rotating tibial insert for use with the tibial tray of FIG. 89.
Figure 91:
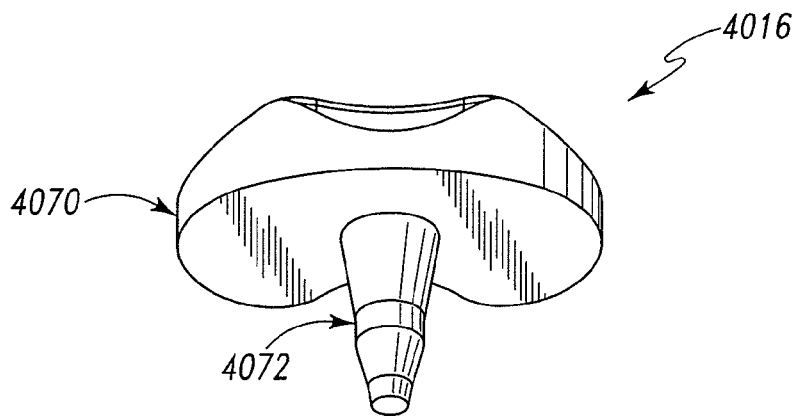
FIG. 91 is a perspective view of a rotating tibial insert for use with the tibial tray of FIG. 89.
Figure 92:
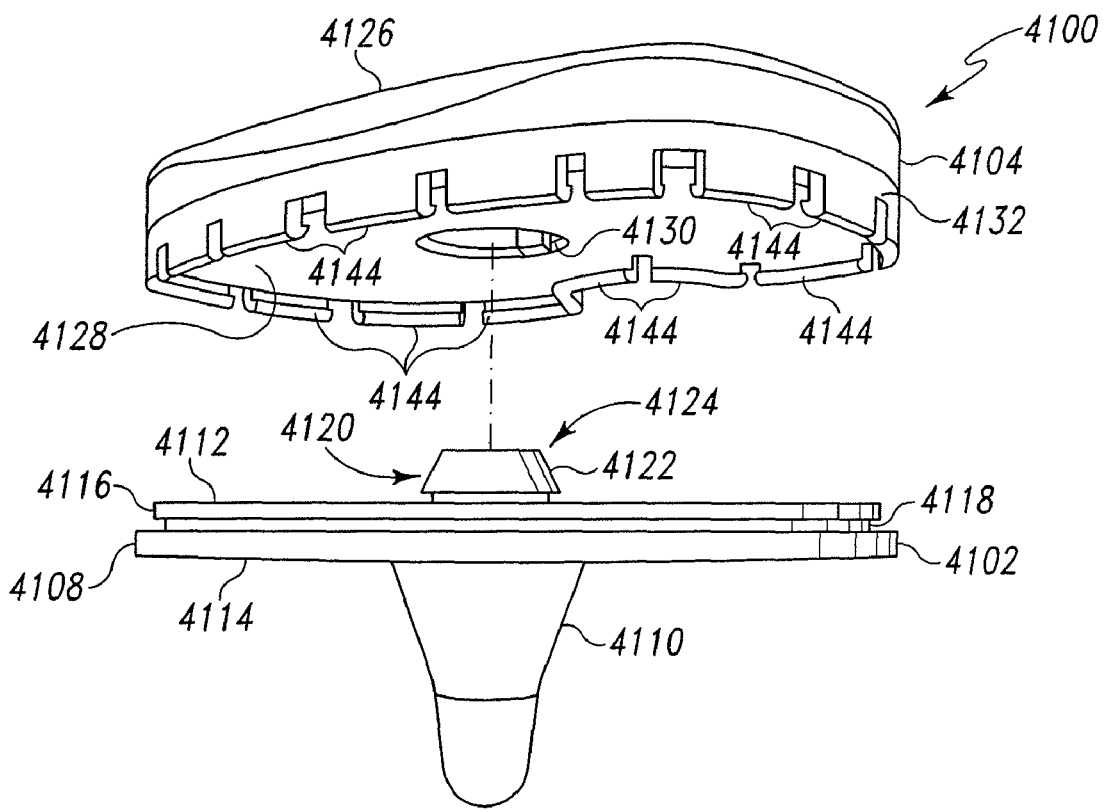
FIG. 92 is an exploded perspective view of another embodiment of an orthopaedic prosthesis assembly including a non-rotating tibial insert.

Referring now to FIGS. 89-91, another prosthetic knee system includes a tibial tray 4012 (see FIG. 89), a fixed tibial insert 4014 (see FIG. 90), and a rotating tibial insert 4016 (see FIG. 91). Looking first to FIG. 89, the tibial tray 4012 includes a platform 4020 and a stem 4022 coupled to the bottom surface 4024 of the platform 4020. A cavity 4030 is formed through the platform 4020 into the stem 4022. The fixed tibial insert 4014, shown in FIG. 90, includes a platform 4040 having an upper bearing surface 4041 and a bottom surface 4044. A skirt or rim 4050 of the platform 4040 extends around the periphery of the platform 4040 and away from the bottom surface 4044 of the platform to define a tray-receiving area 4052 therein. In use, the rim 4050 of the tibial insert 4014 surrounds and captures the platform 4020 of the tibial tray 4012 within the tray-receiving area 4052 in order to prevent rotation of the fixed tibial insert 4014 relative to the tray 4012. The tray 4012 may further include a slot or slots, such as slots 4060 formed in a side surface 4062 of the platform 4020. The outer rim 4050 of the insert 4014 may include tabs 4064 formed on the inner surface 4066 of the rim 4050 and extending inwardly into the tray-receiving area 4052. The tabs 4064 then operate as a snap feature such that when the non-rotating tibial insert 4014 is coupled to the tray 4012, the tabs 4064 are received within the respective slots 4060 in order to further lock the tray 4012 and the fixed insert 4014 together. Such a snap feature may also operate to prevent "lift-off" or axial movement of the tibial insert 4014 relative to the tray 4012. Further, the snap feature may operate to reduce micro-motion between the tray 4012 and the insert 4014. Such micro-motion between the components of a fixed or non-rotating tibial assembly may create wear debris and the snap feature described above may reduce or prevent such wear debris from forming.

Looking now to FIG. 91, the rotating tibial insert 4016 includes a platform 4070 and a stem 4072; however, the insert 4016 does not include the rim 4050 of the fixed tibial insert 4014. As such, when the stem 4072 of the rotating tibial insert 4016 is received within the cavity 4030 of the tray 4012, the insert 4016 is able to rotate relative to the tray 4012. Accordingly, the rotating tibial insert 4016 and the tray 4012 cooperate to provide a rotating tibial assembly.

Illustratively, the outer rim 4050 of the insert 4014 as well as the tabs 4064 of the insert 4014 and the corresponding slots 4060 of the tray 4012 are disclosed within FIGS. 89-91 in order to couple the tibial tray 4012 and the tibial insert 4014 together in order to prevent rotation of the tibial insert 4014 relative to the tibial tray 4012, to reduce or minimize micro-motion between the tibial insert and the tibial tray, and/or to prevent lift-off of the tibial insert relative to the tibial tray, for example. It is within the scope of this disclosure, however, to include other locking features located on or within the tibial insert 4014 and/or tibial tray 4012 to prevent relative movement between the tibial insert 4014 and the tibial tray 4012. It is also within the scope of this disclosure to include locking features which are embodied by components separate from the tibial insert 4014 and the tibial tray 4012 disclosed herein and which may be coupled to one or more of the tibial insert 4014 and the tibial tray 4012 in order to prevent relative movement therebetween.

Figure 93:
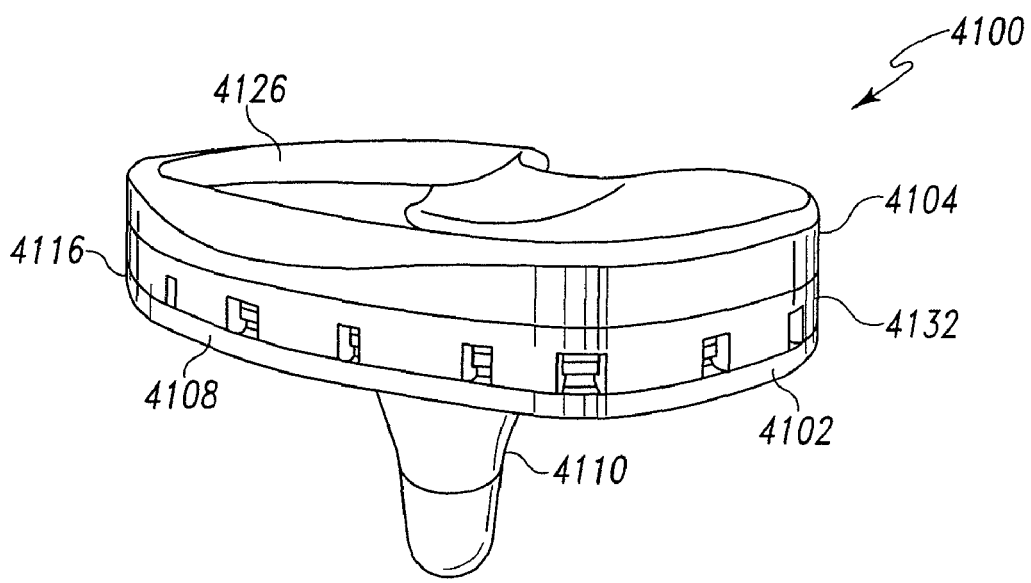
FIG. 93 is a perspective view of the orthopaedic prosthesis assembly of FIG. 92 shown in an assembled configuration.
Figure 94:
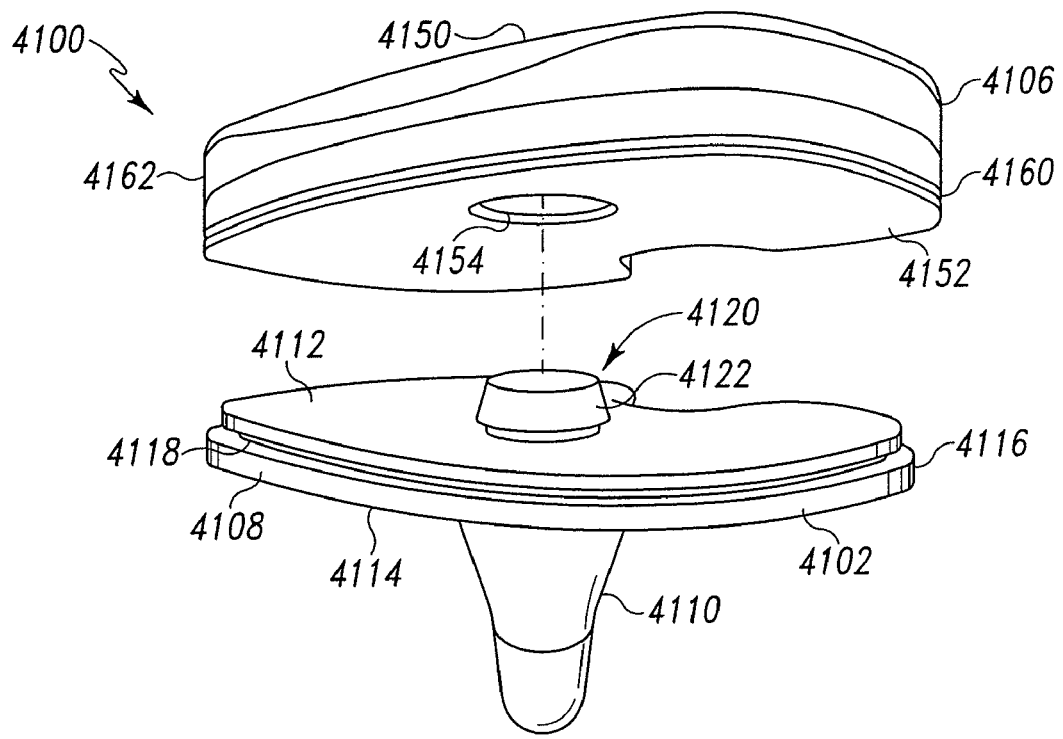
FIG. 94 is an exploded perspective view of the orthopaedic prosthesis assembly of FIG. 92 including a rotating tibial insert.
Figure 95:
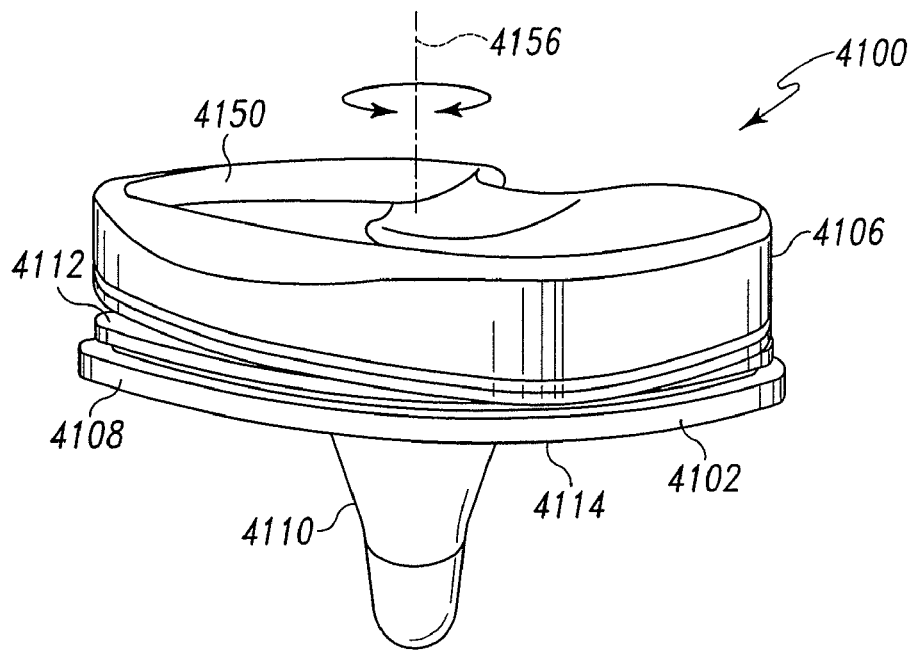
FIG. 95 is a perspective view of the orthopaedic prosthesis assembly of FIG. 94 shown in an assembled configuration.

Referring now to FIGS. 92-95, in another embodiment, a prosthetic knee system 4100 includes a tibial tray 4102, a fixed or non-rotating tibial insert 4104 (see FIGS. 92 and 93) and a rotating tibial insert 4106 (see FIGS. 94 and 95). The tibial inserts 4104, 4106 are illustratively formed from a polymer material, but may be formed from other materials, such as a ceramic material, a metallic material, a bio-engineered material, or the like, in other embodiments. Similarly, the tibial tray 4102 is illustratively formed from a metallic material, but may be formed from other materials, such as a ceramic material, a polymer material, a bio-engineered material, or the like, in other embodiments.

The tibial tray 4102 includes a platform 4108 and a stem 4110. The platform 4108 includes an upper surface 4112, a bottom surface 4114, and a side surface 4116 extending between the upper surface 4112 and the bottom surface 4114. The stem 4110 extends downwardly from the bottom surface 4114 of the platform 4108. The platform 4108 includes a slot 4118 defined in the side surface 4116. Illustratively, the slot 4118 is defined along the length of the side surface 4116 and defines a closed path. However, in other embodiments, the slot 4118 may be embodied as a slot defining an open path, be defined only on particular sections of the side surface 4116, and/or be embodied as a number of smaller slots. The platform 4108 also includes a post 4120 extending upwardly from the upper surface 4112. The post 4120 includes a flange 4122 defined at a proximal end 4124. Illustratively, the flange 4122 includes a upwardly narrowing taper, but flanges having other configurations may be used in other embodiments.

In use, the tibial tray 4102 is configured to be coupled to a surgically-prepared surface of the proximal end of a patient's tibia (not shown). When the tibial tray 4102 is so coupled, the stem 4110 is embedded in patient's tibia to thereby secure the tibial tray 4102 to the patient's bone. In some embodiments, a stem extension (not shown) may include coupled to the stem 4110 to increase the overall length of the stem 4110 and improve the stability of the tibial tray relative to the patient's bony anatomy.

The tibial insert 4104 includes an upper bearing surface 4126 and a bottom surface 4128. The upper bearing surface 4126 is configured to contact a pair of natural or prosthetic femoral condyles of the patient. The bottom surface 4128 includes an aperture 4130 defined therein. As discussed below, the aperture 4130 is configured to receive the post 4120 defined on the upper surface 4112 of the platform 4108 of the tibial tray 4102. The tibial insert 4104 also includes a skirt or rim 4132 extending downwardly from the bottom surface 4128. The rim 4132 includes a number of tabs 4144 extending inwardly. Illustratively, the rim 4132 includes a number of individual downwardly extending sections. Each section includes a separate inwardly extending tab 4132.

As illustrated in FIG. 93, the tibial insert 4104 is configured to be coupled to the tibial tray 4102 in use. To do so, the tibial insert 4104 is positioned on the upper surface 4112 of the platform 4108 such that the post 4120 is received in the aperture 4130 defined in the bottom surface 4116 of the tibial insert 4104. Additionally, the tabs 4144 are received in the slot 4118 defined in the side surface 4116 of the platform 4108 of the tibial tray 4102. When so coupled, the bottom surface 4128 of the tibial insert 4104 is in contact with the upper surface 4112 of the platform 4108 of the tibial tray 4102. In addition, when the non-rotating tibial insert 4104 is coupled to the tibia tray 4102 as shown in FIG. 93, the rim 4132 surrounds the side surface 4116 of the platform 4108 of the tibial tray 4102. The slot 4118 of the tibial tray 4102 and the rim 4132 and tabs 4144 of the rotating tibial insert 4104 cooperate to restrict or prevent rotation of the tibial insert 4104 relative to the tibial tray 4102, to reduce micro-motion between the tibial insert 4104 and the tibial tray 4102, and/or to prevent lift-off of the tibial insert 4104 relative to the tibial tray 4102.

As shown in FIG. 94-95, the rotating tibial insert 4104 may be used with the tibial tray 4102 in place of the non-rotating tibial insert 4104. In some embodiments, the rotating tibial insert 4106 is separate from the rotating tibial insert 4104 and includes an upper bearing surface 4150, a bottom surface 4152, an aperture 4154 defined in the bottom surface 4150 similar to the upper bearing surface 4126, the bottom surface 4128, and the aperture 4130 of the non-rotating tibial insert 4104. However, in other embodiments, the rim 4132 of the non-rotating tibial insert 4104 is configured to be removed therefrom to selectively change the non-rotating tibial insert 4104 into a rotating tibial insert. It should be appreciated that, in such embodiments, the non-rotating tibial insert 4104 and the rotating tibial insert 4106 are the same tibial insert. Additionally, in such embodiments, the tibial insert 4104, 4106 may include a slot 4160 (see FIG. 94) defined in a side wall 4162 configured to receive a portion of the rim 4132 to secure the rim 4132 to the tibial insert 4104, 4106.

As shown in FIG. 95, the rotating tibial insert 4106 may be coupled to the tibial tray 4102 in a manner similar to the non-rotating tibial insert 4104. To do so, the rotating tibial insert 4106 is positioned on the upper surface 4112 of the platform 4108 such that the post 4120 is received in the aperture 4154 defined in the bottom surface 4152 of the tibial insert 4106. When so coupled, the bottom surface 4152 of the tibial insert 4106 is in contact with the upper surface 4112 of the platform 4108 of the tibial tray 4102. Because the rotating tibial insert 4106 does not include the rim 4132 and tabs 4114, the insert is free to rotate about an axis 4156 defined by the post 4120 of the tibial insert 4102. In should be appreciated that the circular shape of the post 4120 facilitates the rotation of the rotating tibial insert 4106.

Figure 96:
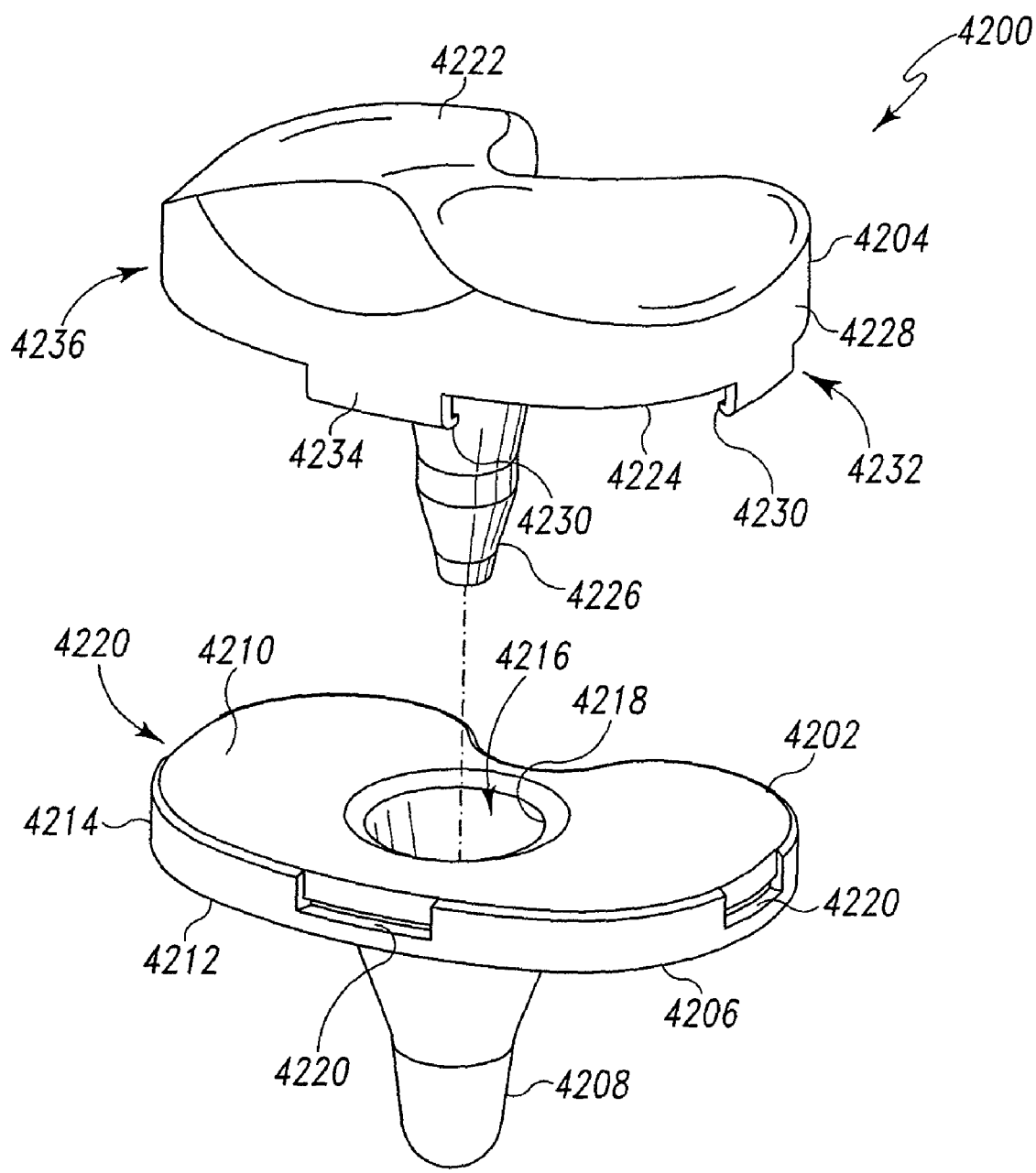
FIG. 96 is an exploded perspective view of another embodiment of an orthopaedic prosthesis assembly including a non-rotating tibial insert.

Referring now to FIG. 96, in another embodiment, a prosthetic knee system 4200 includes a tibial tray 4202, a fixed or non-rotating tibial insert 4204, and a rotating tibial insert (not shown). The rotating tibial insert may be similar to the rotating tibial insert 794 described above in regard to FIG. 87. The tibial insert 4204 is illustratively formed from a polymer material, but may be formed from other materials, such as a ceramic material, a metallic material, a bio-engineered material, or the like, in other embodiments. Similarly, the tibial tray 4202 is illustratively formed from a metallic material, but may be formed from other materials, such as a ceramic material, a polymer material, a bio-engineered material, or the like, in other embodiments.

The tibial tray 4202 includes a platform 4206 and a stem 4208. The platform includes an upper surface 4210, a bottom surface 4212, and a side surface 4214 extending between the upper surface 4210 and the bottom surface 4212. The tibial tray 4202 also includes a cavity 4216 having an opening 4218 defined on the upper surface 4210. The stem 4208 extends downwardly from the bottom surface 4212 of the platform 4206. The platform 4206 includes a number of slots 4220 defined in the side surface 4214. Illustratively, the platform 4206 includes a slot 4220 defined in the lateral side of the side surface 4214, a slot 4220 defined in the anterior side of the side surface 4214, and a slot 4220 defined in the medial side of the side surface 4220. However, in other embodiments, the platform 4206 may include any number of slots 4220 defined in the side surface 4214.

As described above in regard to the tibial tray 4102 of FIGS. 92-95, the tibial tray 4202 is configured to be coupled to a surgically-prepared surface of the proximal end of a patient's tibia (not shown). When the tibial tray 4202 is so coupled, the stem 4208 is embedded in patient's tibia to thereby secure the tibial tray 4202 to the patient's bone. In some embodiments, a stem extension (not shown) may include coupled to the stem 4208 to increase the overall length of the stem 4208 and improve the stability of the tibial tray 4202 relative to the patient's bony anatomy.

The tibial insert 4204 includes an upper bearing surface 4222, a bottom surface 4224, and a stem 4226. The upper bearing surface 4222 is configured to contact a pair of natural or prosthetic femoral condyles of the patient. The stem 4226 extends downwardly from the bottom surface 4224. The tibial insert 4204 also includes a sectioned rim 4228 extending downwardly from the bottom surface 4224. The rim 4228 includes a number of tabs 4230 extending inwardly. Illustratively, the rim 4228 includes a lateral rim section 4232, an anterior rim section 4234, and a medial rim section 4336. Each section 4232, 4334, 4336 includes a separate inwardly extending tab 4230. However, in other embodiments, the rim 4228 may include more or less sections.

The tibial insert 4204 is configured to be coupled to the tibial tray 4202 in use. To do so, the tibial insert 4204 is positioned such that the stem 4206 is received in the opening 4218 defined in the upper surface 4210 of the tibial tray 4202. The tibial insert 4204 is seated on the upper surface 4210 of the platform 4206 such that the of the tabs 4230 of the rim 4228 are received in the corresponding slots 4220 defined in the side surface 4214 of the platform 4206 of the tibial tray 4202. When so coupled, the bottom surface 4224 of the tibial insert 4204 is in contact with the upper surface 4210 of the platform 4206 of the tibial tray 4202. The slots 4220 of the tibial tray 4202 and the rim 4228 and tabs 4230 of the rotating tibial insert 4204 cooperate to restrict or prevent rotation of the tibial insert 4204 relative to the tibial tray 4202, to reduce micro-motion between the tibial insert 4204 and the tibial tray 4202, and/or to prevent lift-off of the tibial insert 4204 relative to the tibial tray 4202.

A rotating tibial insert, similar to the tibial insert 794, may be used with the tibial tray in place of the non-rotating tibial insert. The rotating tibial insert may be coupled to the tibial tray in a manner similar to the non-rotating tibial insert. To do so, the rotating tibial insert is positioned such that a stem of the rotating tibial insert is received in the opening defined in the upper surface of the tibial tray. Because the rotating tibial insert does not include the tabs of the non-rotating tibial insert, the insert is free to rotate about an axis defined by the post of the tibial insert.

Figure 97:
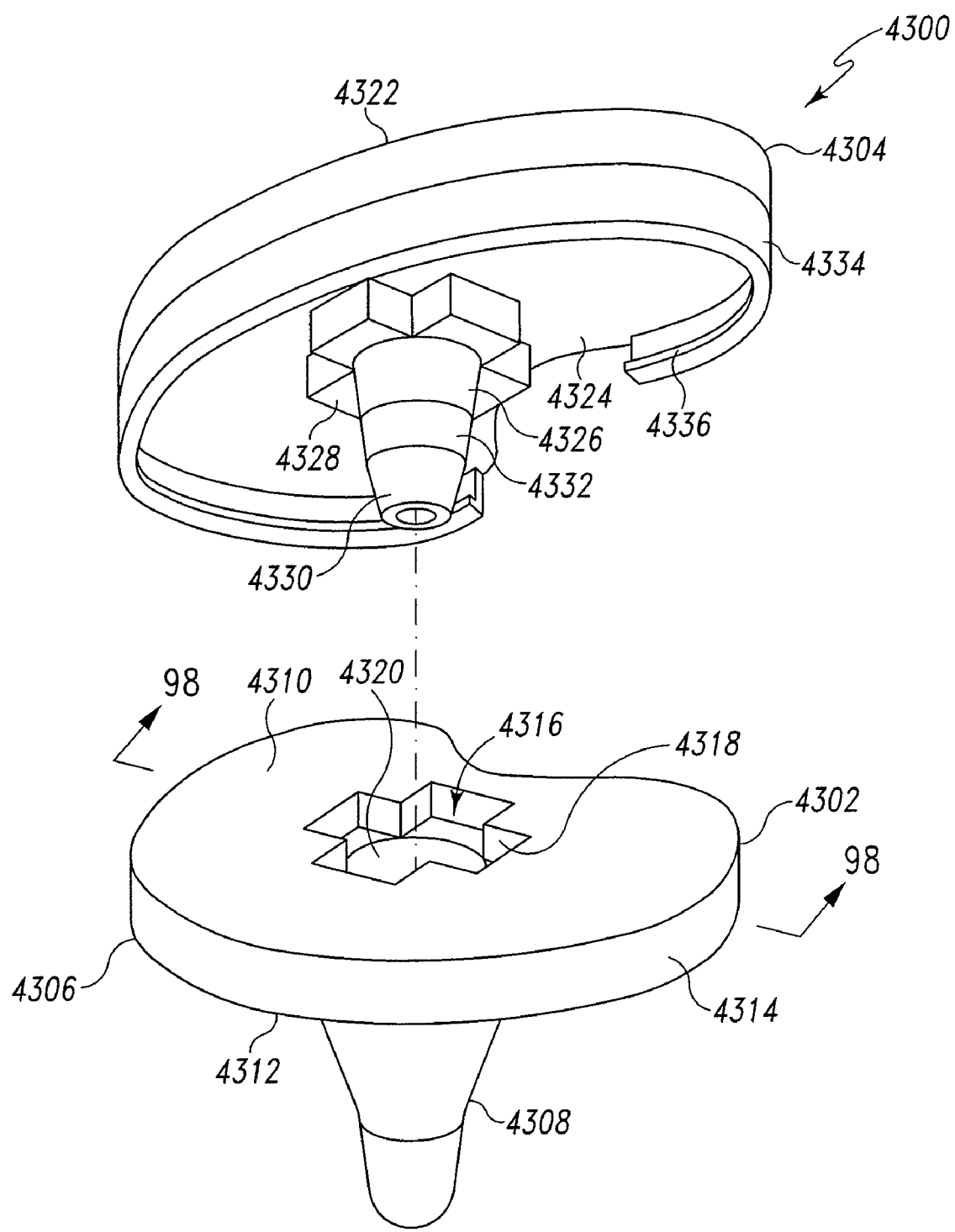
FIG. 97 is an exploded perspective view of another embodiment of an orthopaedic prosthesis assembly including a non-rotating tibial insert.
Figure 98:
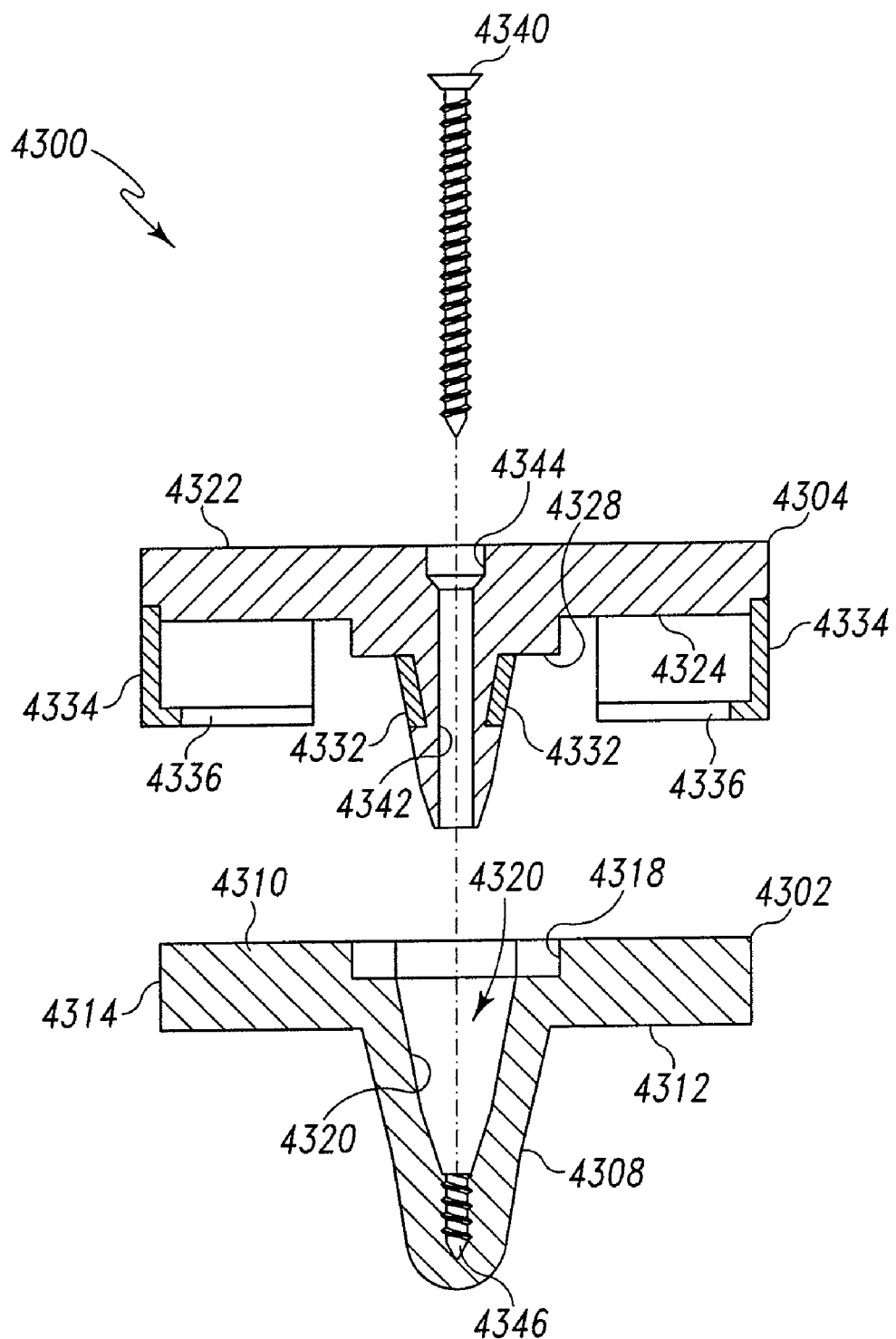
FIG. 98 is a cross-sectional view of the orthopaedic prosthesis assembly of FIG. 97 taken generally along the line 97-97.
Figure 99:
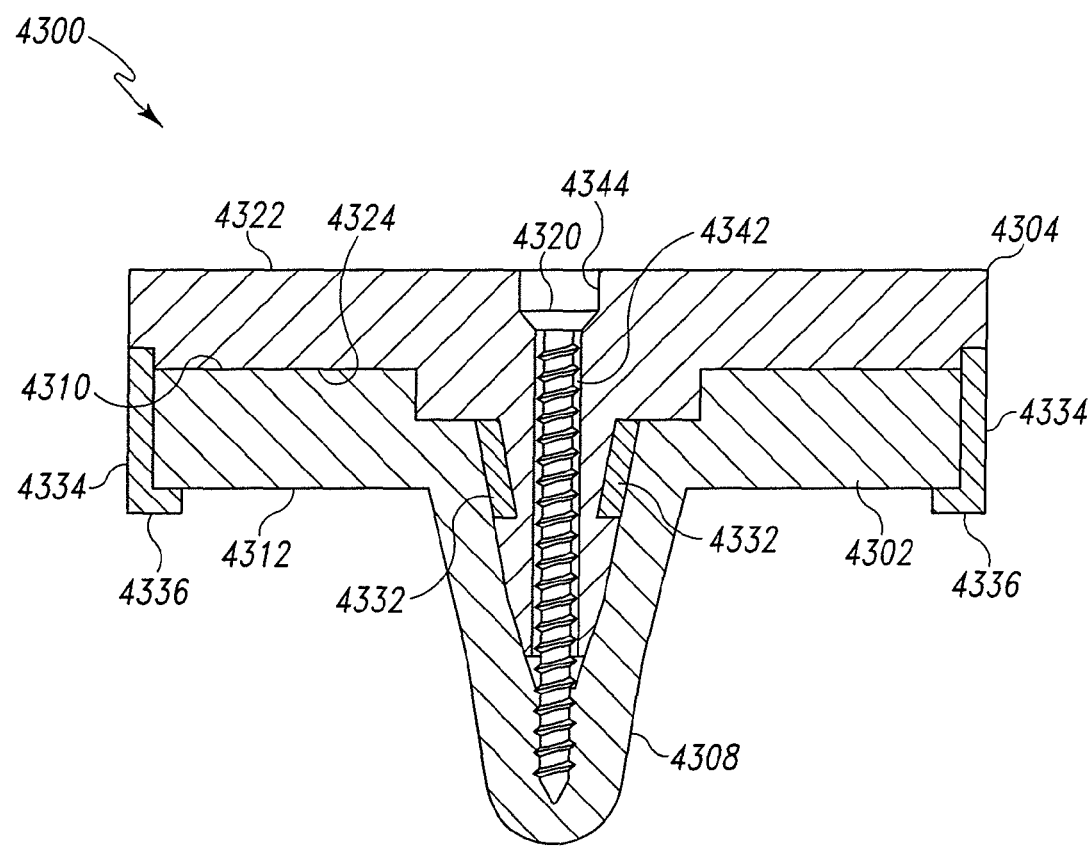
FIG. 99 is a cross-sectional view of the orthopaedic prosthesis assembly of FIG. 97 in an assembled configuration.

Referring now to FIGS. 97-99, in another embodiment, a prosthetic knee system 4300 includes a tibial tray 4302, a fixed or non-rotating tibial insert 4304, and a rotating tibial insert (not shown). The rotating tibial insert 4304 may be similar to the rotating tibial insert 794 described above in regard to FIG. 87. The tibial insert 4304 is illustratively formed from a polymer material, but may be formed from other materials, such as a ceramic material, a metallic material, a bio-engineered material, or the like, in other embodiments. Similarly, the tibial tray 4302 is illustratively formed from a metallic material, but may be formed from other materials, such as a ceramic material, a polymer material, a bio-engineered material, or the like, in other embodiments.

The tibial tray 4302 includes a platform 4306 and a stem 4308. The platform 4306 includes an upper surface 4310, a bottom surface 4312, and a side surface 4314 extending between the upper surface 4310 and the bottom surface 4312. The stem 4308 extends downwardly from the bottom surface 4812 of the platform 4306. The tibial tray 4302 also includes a cavity 4316 having a keyed opening 4318 defined on the upper surface 4310. Illustratively, as shown in FIG. 97, the keyed opening has cruciform shape (i.e., the keyed opening 4318 has a cruciform top profile). However, as discussed in more detail below, the keyed opening 4318 may have other shapes in other embodiments. The cavity 4316 is defined by an inner wall 4320 of the tibial tray and has an inwardly sloping taper as discussed in more detail below.

As described above in regard to the tibial tray 4102 of FIGS. 92-95, the tibial tray 4302 is configured to be coupled to a surgically-prepared surface of the proximal end of a patient's tibia (not shown). When the tibial tray 4302 is so coupled, the stem 4308 is embedded in patient's tibia to thereby secure the tibial tray 4302 to the patient's bone. In some embodiments, a stem extension (not shown) may include coupled to the stem 4308 to increase the overall length of the stem 4308 and improve the stability of the tibial tray 4302 relative to the patient's bony anatomy.

The tibial insert 4304 includes an upper bearing surface 4322, a bottom surface 4324, and a stem 4326. The upper bearing surface 4322 is configured to contact a pair of natural or prosthetic femoral condyles of the patient. The stem 4326 extends downwardly from the bottom surface 4324 and includes a base 4328 and an elongated shaft 4330 extending downwardly from the base 4328. The base 4328 of the stem 4326 has a shape corresponding to the shape of the keyed opening 4318 of the tibial tray 4302. For example, in the illustrative embodiments of FIG. 97, the base 4328 of the stem 4326 has a cruciform shape such that the base 4328 is configured to be received in the keyed opening 4318 when the tibial insert 4304 is coupled to the tibial tray 4302. Although the keyed opening 4318 and base 4328 have a cruciform shape in the illustrative embodiments, the keyed opening 4318 and base 4328 may have other corresponding non-circular shapes in other embodiments. For example, the keyed opening 4318 and base 4328 may have octagonal or star shape as illustrated in FIG. 75 or a rectangular or square shape as illustrated in FIG. 76.

The non-rotating tibial insert 4304 also includes a metal ring 4332 secured to a central portion of the shaft 4330 of the stem 4326. The metal ring 4322 has an inwardly sloping taper that corresponds to the taper of the inner sidewall 4320 of the tibial tray 4302. The tapers of the metal ring 4332 and the inner sidewall 4320 are designed such that when the non-rotating tibial insert 4304 is coupled to the tibial tray 4302, the metal ring 4332 and the inner sidewall 4320 contact each other and form a friction lock therebetween as illustrated in FIG. 99. In one particular embodiment, the tapers of the metal ring 4332 and the inner sidewall 4320 are embodied as corresponding Morse tapers. For example, in one particular embodiment, a Morse taper having a taper-per-foot in the range of about 0.59858 to about 0.63151 may be used. However, in other embodiments, other types of friction lock tapers may be used.

In some embodiments, the non-rotating tibial insert 4304 may also include a rim or skirt 4434 extending downwardly from the bottom surface 4324 of the tibial insert 4304. The rim 4334 includes a tab 4336 extending inwardly therefrom.

The rim 4334 may extend downwardly from the periphery of the bottom surface 4324 or from only a portion thereof as illustrated in FIG. 97. Illustratively, the rim 4334 and/or the tab is formed from a flexible material. The flexible material may be embodied as any material flexible enough to allow the tibial insert 4304 to be coupled to the tibial tray 4302, but rigid enough to provide some amount of resistance to lift-off as described below.

The tibial insert 4304 is configured to be coupled to the tibial tray 4302 in use. To do so, the tibial insert 4304 is positioned such that the elongated shaft 4330 of the stem 4326 is received in the cavity 4366 of the tibial tray 4302 and the base 4328 of the stem 4326 is received in the keyed opening 4318. In embodiments wherein the tibial insert 4304 includes the rim 4334, the tibial insert 4304 is seated on the upper surface 4310 of the platform 4306 such that the tabs 4336 of the rim 4334 clip the bottom surface 4312 of the tibial tray 4302 as illustrated in FIG. 99. In some embodiments, the orthopaedic prosthesis assembly 4330 may also include a fastener 4340, which may be embodied as a screw or bolt. In such embodiments, the tibial insert 4304 includes an internal passageway 4342 extending therethrough. The passageway 4342 includes an opening 4344 in the upper bearing surface 4322. The cavity 4320 of the tibial tray 4302 includes a threaded aperture 4346 defined at a distal end of the cavity 4320. Once the non-rotating tibial insert 4304 is coupled to the tibial tray 4302, the fastener 4340 may be inserted into the internal passageway 4342 of the tibial insert 4304 and threaded into the threaded aperture 4346 of the tibial tray 4302 to thereby secure the tibial insert 4304 to the tibial tray 4302 as illustrated in FIG. 99.

When the non-rotating tibial insert 4304 is coupled to the tibial tray 4302, the bottom surface 4324 of the tibial insert 4304 is in contact with the upper surface 4310 of the platform 4306 of the tibial tray 4302. In addition, the base 4328 of the stem 4326 is received in the keyed opening 4318 of the tibial tray 4302 and the tab 4336 of the tibial insert 4304 is clipped over the bottom surface 4312 of the tibial tray 4302. Additionally, as discussed above, the metal ring 4332 secured to the stem 4326 of the tibial insert 4304 is in contact with the inner sidewall 4320 of the tibial tray 4302 to form a friction lock therebetween. The friction lock, rim 4334, and fastener 4340 (if used) cooperate to restrict or prevent rotation of the tibial insert 4304 relative to the tibial tray 4302, to reduce micro-motion between the tibial insert 4304 and the tibial tray 4302, and/or to prevent lift-off of the tibial insert 4304 relative to the tibial tray 4302.

A rotating tibial insert, similar to the tibial insert 794, may be used with the tibial tray 4302 in place of the non-rotating tibial insert 4304. The rotating tibial insert may be coupled to the tibial tray 4302 in a manner similar to the non-rotating tibial insert 4304. To do so, the rotating tibial insert is positioned such that a stem of the rotating tibial insert is received in the cavity 4320 defined in the upper surface of the tibial tray 4302. Because the rotating tibial insert does not include the keyed base 4328 of the non-rotating tibial insert 4304, the insert is free to rotate about an axis 4328 of the post of the tibial insert 4302.

Figure 100:
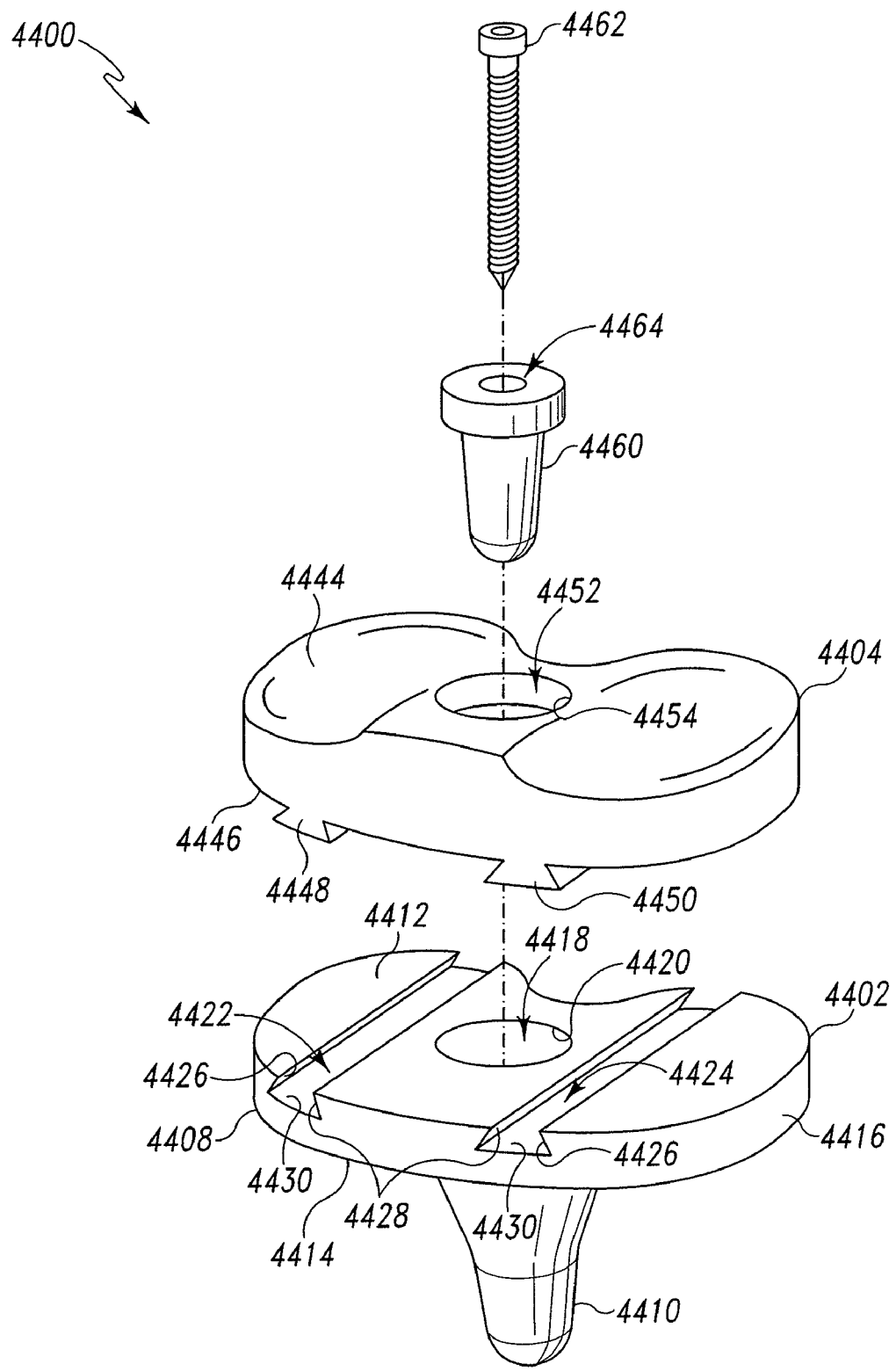
FIG. 100 is an exploded perspective view of another embodiment of an orthopaedic prosthesis assembly including a non-rotating tibial insert.
Figure 101:
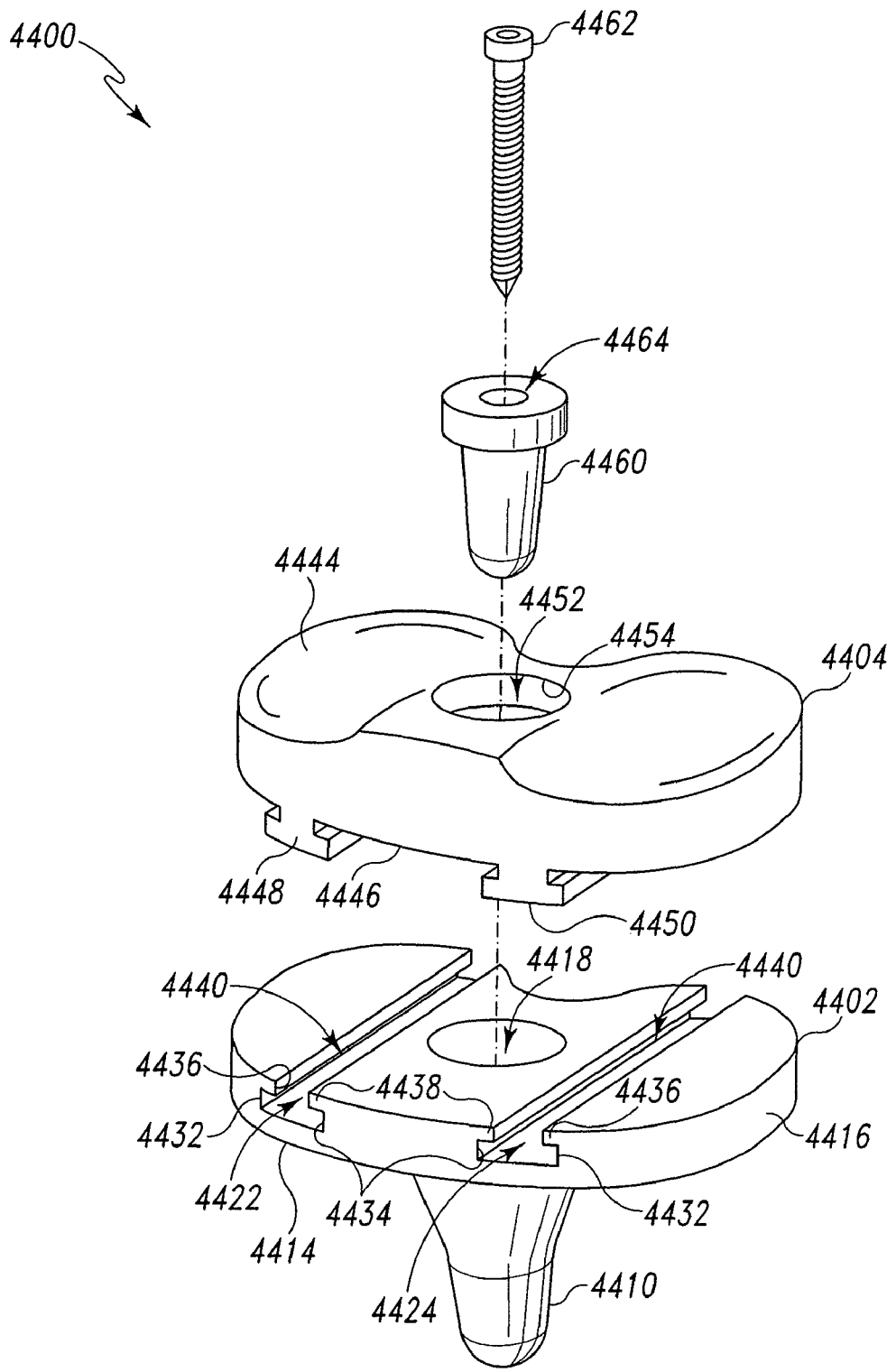
FIG. 101 is an exploded perspective view of another embodiment of the orthopaedic prosthesis assembly of FIG. 100.
Figure 102:
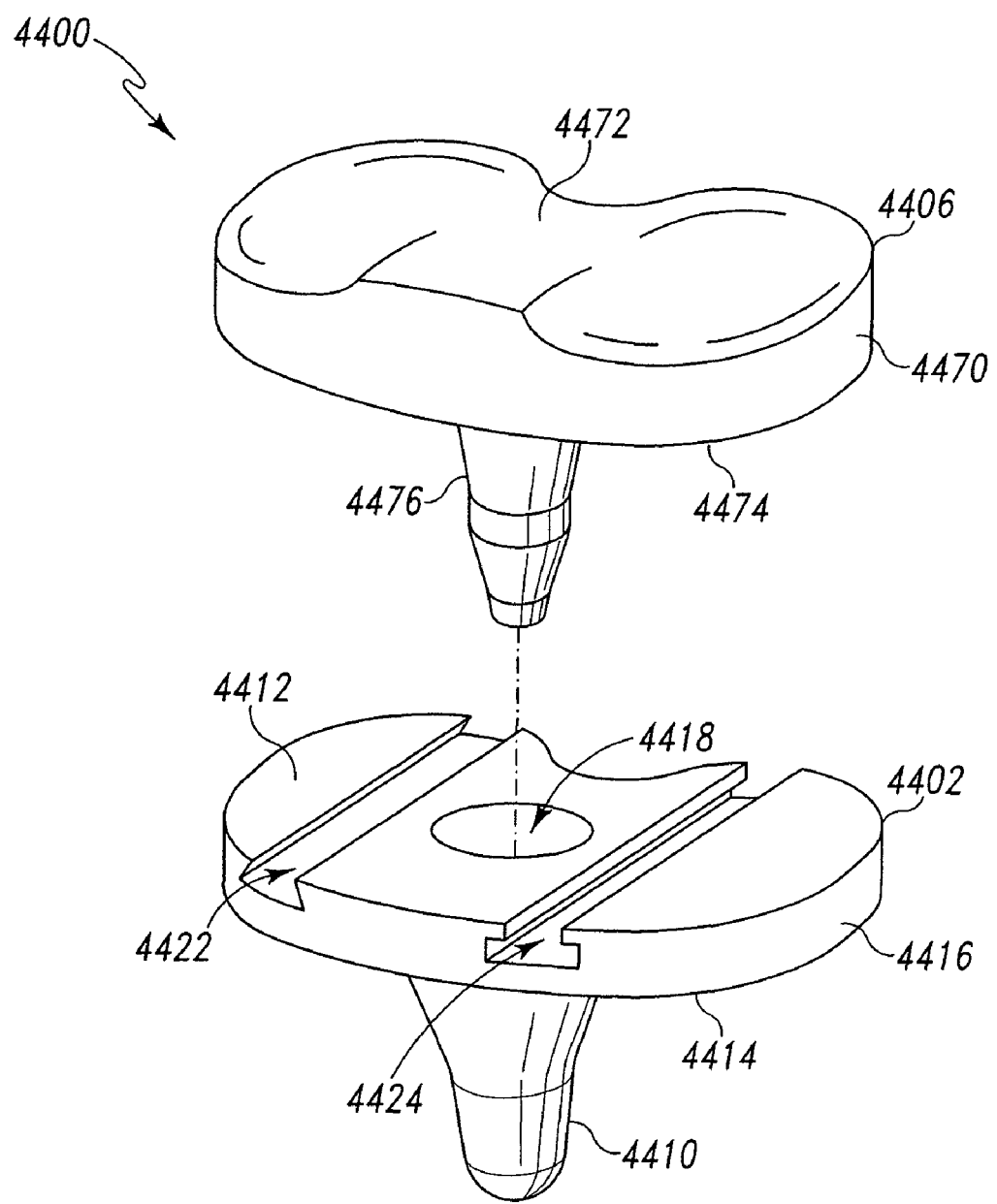
FIG. 102 is an exploded perspective view of the orthopaedic prosthesis assembly of FIG. 100 including a rotating tibial insert.
Figure 103:
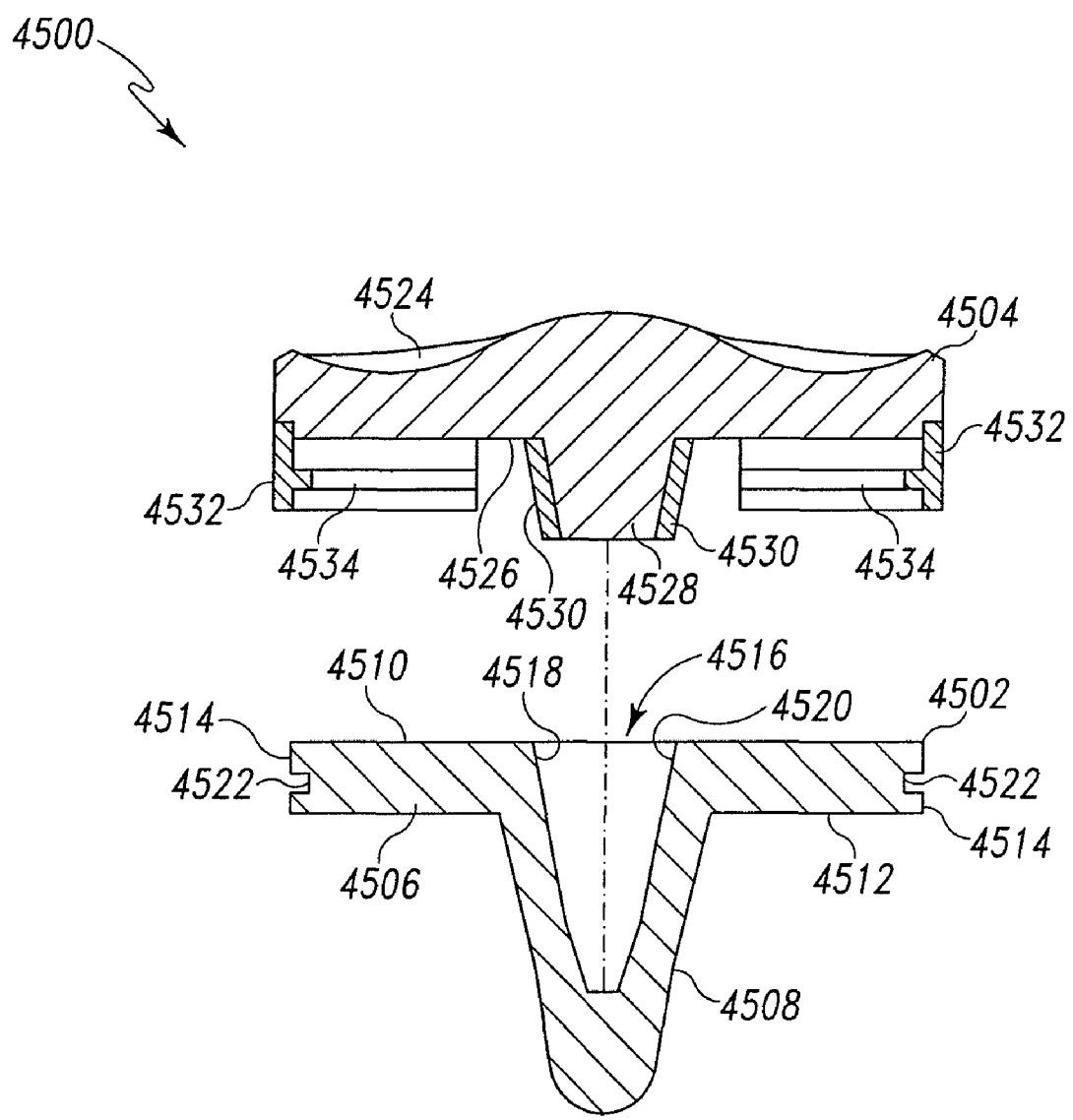
FIG. 103 is an exploded perspective view of another embodiment of an orthopaedic prosthesis assembly including a non-rotating tibial insert.

Referring now to FIGS. 100-102, in another embodiment, a prosthetic knee system 4400 includes a tibial tray 4402, a fixed or non-rotating tibial insert 4404 (see FIGS. 100 and 101), and a rotating tibial insert 4406 (see, e.g., FIG. 102). The tibial inserts 4402, 4004 are illustratively formed from a polymer material, but may be formed from other materials, such as a ceramic material, a metallic material, a bio-engineered material, or the like, in other embodiments. Similarly, the tibial tray is illustratively formed from a metallic material, but may be formed from other materials, such as a ceramic material, a polymer material, a bio-engineered material, or the like, in other embodiments.

The tibial tray 4402 includes a platform 4408 and a stem 4410. The platform 4408 includes an upper surface 4412, a bottom surface 4414, and a side surface 4416 extending between the upper surface 4412 and the bottom surface 4414. The tibial tray 4402 also includes a cavity 4418 having an opening 4420 defined on the upper surface 4412. The stem 4410 extends downwardly from the bottom surface 4414 of the platform 4408. The platform 4408 includes a medial guide track 4422 and a lateral guide track 4424 defined in the upper surface 4412. It should be appreciated that although the guide tracks 4422, 4424 are referred to as medial and lateral guide tracks, respectively, the particular orientation of each track 4422, 4424 depends upon which knee of the patient is receiving the orthopaedic prosthesis. As such, either guide track 4422, 4424 may be a medial or lateral track. Regardless, for clarity, the guide track will be refereed to as a medial guide track 4422 and the guide track will be referred to as a lateral guide track 4424 with the understanding that either guide track may be a medial/lateral guide track based on the particular application.

Illustratively, the guide tracks 4422, 4424 are defined in the upper surface 4412 of the tibial tray 4402 in the anterior/posterior direction. However, in other embodiments, the guide tracks 4422, 4424 may be defined in the upper surface 4412 in other directions. Additionally, although the illustrative embodiment includes only two guide tracks 4422, 4424, the tibial tray 4402 may include additional guide tracks in other embodiments. Illustratively, each guide track 4422, 4424 is defined by a first sidewall 4426, a second sidewall 4428, and a bottom wall 4430. The first and second sidewalls 4426, 4428 are tapered inwardly such that the guide tracks 4422, 4424 have a substantially dovetail shape. That is, each of the guide tracks 4422, 4424 has a dovetail shaped cross-section. However, in other embodiments, the guide tracks 4422, 4424 may have other shapes. For example, in some embodiments, the first and second sidewalls 4426, 4428 may be substantially straight such that the guide tracks 4422, 4424 have a substantially rectangular or square shape. Alternatively, as illustrated in FIG. 101, the guide tracks 4422, 4424 may include straight side walls 4432, 4434 having a first lip 4436 and second lip 4438 extending inwardly therefrom. The lips 4436, 4438 define an opening 4430 therebetween. In such embodiments, the guide tracks 4422, 4424 are substantially "T"-shaped. Additionally, in some embodiments, the medial guide track 4422 may have a shape different from the lateral guide track 4424. For example, as illustrated in FIG. 102, the medial guide track 4422 may have a substantially dovetail shape while the lateral guide track 4424 has a substantially "T" shape. Such a configuration allows the non-rotating tibial insert 4404 to be keyed as discussed below such that the tibial insert 4404 may be coupled to the tibial tray 4402 in only a single orientation.

Again, as described above in regard to the tibial tray 4102 of FIGS. 92-95, the tibial tray 4402 is configured to be coupled to a surgically-prepared surface of the proximal end of a patient's tibia (not shown). When the tibial tray 4402 is so coupled, the stem 4410 is embedded in patient's tibia to thereby secure the tibial tray 4402 to the patient's bone. In some embodiments, a stem extension (not shown) may include coupled to the stem 4410 to increase the overall length of the stem 4410 and improve the stability of the tibial tray 4402 relative to the patient's bony anatomy.

The tibial insert 4404 includes an upper bearing surface 4444, a bottom surface 4446, and a pair of rails 4448, 4450.

The upper bearing surface is 4444 configured to contact a pair of natural or prosthetic femoral condyles of the patient. The tibial insert 4404 includes an internal passageway 4452 having an opening 4454 defined in the upper bearing surface 4444. The rails 4448, 4450 extend downwardly from the bottom surface 4446 and are positioned thereon in an orientation and location corresponding to the guide tracks 4422, 4424 of the tibial insert 4404 such that the tibial insert 4404 may be coupled thereto. For example, in the illustrative embodiment, the rails 4448, 4450 extend across the bottom surface 4446 in an anterior/posterior direction. Additionally, the rails 4448, 4450 have a shape corresponding to the shape of the guide tracks 4422, 4424 such that the rails 4448, 4450 may be received therein. In the embodiment illustrated in FIG. 100, the rails 4448, 4450 have a substantially dovetail shape. However, in the embodiment illustrated in FIG. 101, the rails 4448, 4450 have substantially "T"-shape and may have other shapes in other embodiments.

The orthopaedic prosthesis assembly 4400 also includes a stem 4460 separate from the tibial insert 4404 and the tibial tray 4402 and a fastener 4462 such as a screw or bolt. The stem 4460 is insertable into the internal passageway 4452 of the tibial insert 4404 and the cavity 4418 of the tibial tray 4402 via the respective openings 4454, 4420. To do so, the tibial insert 4404 is positioned such that each rail 4448, 4450 is received in the corresponding guide track 4422, 4424. The tibial insert 4404 is then moved to a location in which the opening 4420 defined in the upper surface 4412 of the tibial tray 4402 is in registry with the internal passageway 4452 defined in the tibial insert 4404. The stem 4460 is then inserted into the passageway 4452. A portion of the stem 4460 also extends into the cavity 4418 of the tibial tray 4402. The stem 4460 includes an internal passageway 4464 sized to receive the fastener 4462, which is threaded into a threaded aperture (not shown) defined at the distal end of the cavity 4418 of the tibial tray 4402 to secure the tibial insert 4404 to the tibial tray 4402.

When the non-rotating tibial insert 4404 is coupled to the tibial tray 4402, the bottom surface 4406 of the tibial insert 4404 is in contact with the upper surface 4412 of the platform 4408 of the tibial tray 4402. In addition, each rail 4448, 4450 is received in the corresponding guide track 4422, 4424. The rails 4448, 4450, guide tracks 4422, 4424, and stem 4460 cooperate to restrict or prevent rotation of the tibial insert 4404 relative to the tibial tray 4402, to reduce micro-motion between the tibial insert 4404 and the tibial tray 4402, and/or to prevent lift-off of the tibial insert 4404 relative to the tibial tray 4402.

As shown in FIG. 102, rotating tibial insert 4406 may be used with the tibial tray 4402 in place of the non-rotating tibial insert 4404. The rotating tibial insert 4406 is similar to the tibial insert 794 and includes a platform 4470 having an upper bearing surface 4472 and bottom surface 4474 and a stem 4476 extending from the bottom surface 4474. The rotating tibial insert 4406 may be coupled to tibial tray 4402 by positioning the rotating tibial insert 4406 such that a stem 4476 of the rotating tibial insert 4406 is received in the cavity 4418 defined in the upper surface 4412 of the tibial tray 4402. Because the rotating tibial insert 4406 does not include rails extending from the bottom surface 4472, the insert 4406 is free to rotate about an axis relative to the tibial tray 4402.

In some embodiments, the rails 4448, 4450 may be removable from the tibial insert 4404. For example, the rails 4448, 4450 may be secured to the to the tibial insert 4404 via a number of removable securing devices such as bolts or the like. In such embodiments, the rails 4448, 4450 may be removed from the tibial insert 4404 by removing the securing devices. In other embodiments, the tibial insert 4404 may include a pair of guide tracks similar to the guide tracks 4422, 4424 of the tibial tray 4402. In such embodiments, the rails 4448, 4450 are separate from the tibial insert 4404. Additionally, in such embodiments, the rails 4448, 4450 are configured to be received in the guide tracks of the tibial insert 4404 and into the guide tracks 4422, 4424 of the tibial tray. For example, the rails 4448, 4450 may be substantially "T"-shaped. Regardless, in embodiments wherein the rails 4448, 4450 are removable from the tibial insert 4404 and/or the tibial tray 4402, the tibial insert 4404 may be configurable as a fixed or a mobile bearing. That is, when the rails 4448, 4450 are coupled to the tibial insert 4404 and/or the tibial tray 4402, the tibial insert 4404 is configured as a fixed bearing. However, when the rails 4448, 4450 are removed from the tibial insert 4404 and/or the tibial tray 4402, the tibial insert 4404 is configured as a mobile bearing.

Referring now to FIGS. 103-106, in another embodiment, a prosthetic knee system 4500 includes a tibial tray 4502, a fixed or non-rotating tibial insert 4504, and a rotating tibial insert (not shown). The rotating tibial insert may be similar to the rotating tibial insert 794 described above in regard to FIG. 87. The non-rotating tibial insert 4504 is illustratively formed from a polymer material, but may be formed from other materials, such as a ceramic material, a metallic material, a bio-engineered material, or the like, in other embodiments. Similarly, the tibial tray 4502 is illustratively formed from a metallic material, but may be formed from other materials, such as a ceramic material, a polymer material, a bio-engineered material, or the like, in other embodiments.

The tibial tray 4502 includes a platform 4506 and a stem 4508. The platform 4506 includes an upper surface 4510, a bottom surface 4512, and a side surface 4514 extending between the upper surface 4510 and the bottom surface 4512. The stem 4508 extends downwardly from the bottom surface 4512 of the platform 4506. The tibial tray 4502 also includes a cavity 4516 having an opening 4518 defined on the upper surface 4510. The cavity 4516 is defined by an inner sidewall 4520 having an inwardly sloping taper. The platform 4506 includes a slot 4522 defined in the side surface 4514. Illustratively, the slot 4522 is defined along the length of the side surface 4514 and defines a closed path. However, in other embodiments, the slot 4522 may be embodied as a slot defining an open path, be defined only on particular sections of the side surface 4514, and/or be embodied as a number of smaller slots.

The tibial tray 4502 is configured to be coupled to a surgically-prepared surface of the proximal end of a patient's tibia (not shown). When the tibial tray 4502 is so coupled, the stem 4508 is embedded in patient's tibia to thereby secure the tibial tray 4502 to the patient's bone. In some embodiments, a stem extension (not shown) may include coupled to the stem 4508 to increase the overall length of the stem 4508 and improve the stability of the tibial tray 4502 relative to the patient's bony anatomy.

The tibial insert 4504 includes an upper bearing surface 4524, a bottom surface 4526, and a stem 4528. The upper bearing surface 4524 is configured to contact a pair of natural or prosthetic femoral condyles of the patient. The stem 4528 extends downwardly from the bottom surface 4526 and includes a metal ring 4530 secured thereto. The metal ring 4530 has an inwardly sloping taper that corresponds to the taper of an inner sidewall 4520 of the tibial tray 4502. The tapers of the metal ring 4530 and the inner sidewall 4520 are designed such that when the non-rotating tibial insert 4504 is coupled to the tibial tray 4502, the metal ring 4530 and the inner sidewall 4520 contact each other and form a friction lock therebetween. In one particular embodiment, the tapers of the metal ring 4530 and the inner sidewall 4520 are embodied as corresponding Morse tapers. For example, in one particular embodiment, a Morse taper having a taper-per-foot in the range of about 0.59858 to about 0.63151 may be used. However, in other embodiments, other types of friction lock tapers may be used.

The non-rotating tibial insert 4504 also includes a rim or skirt 4532 extending downwardly form the bottom surface 4526 of the tibial insert 4504. The rim 4532 includes a tab 4534 extending inwardly therefrom. The rim 4532 may extend downwardly from the complete periphery of the bottom surface 4526 or from only a portion thereof. Illustratively, the rim 4532 and/or the tab 4534 is formed from a flexible material. The flexible material may be embodied as any material flexible enough to allow the tibial insert 4504 to be coupled to the tibial tray 4502, but rigid enough to provide some amount of resistance to lift-off as described below.

The tibial insert 4504 is configured to be coupled to the tibial tray 4502 in use. To do so, the tibial insert 4504 is positioned such that the stem 4528 is received in the cavity 4516 of the tibial tray 4502. The tibial insert 4504 is seated on the upper surface 4510 of the platform 4506 such that the tab 4534 of the rim 4532 is received in the slot 4522 defined on the side surface 4514 of the tibial tray 4502. When non-rotating tibial insert 4504 is coupled to the tibial tray 4502, the bottom surface 4526 of the tibial insert 4504 is in contact with the upper surface 4510 of the platform 4506 of the tibial tray 4502. In addition, the metal ring 4530 secured to the stem 4528 of the tibial insert 4504 is in contact with the inner sidewall 4520 of the tibial tray 4502 to form a friction lock therebetween. The friction lock, rim 4534, and slot 4522 cooperate to restrict or prevent rotation of the tibial insert 4504 relative to the tibial tray 4502, to reduce micro-motion between the tibial insert 4504 and the tibial tray 4502, and/or to prevent lift-off of the tibial insert 4504 relative to the tibial tray 4502.

A rotating tibial insert, similar to the tibial insert 794, may be used with the tibial tray 4502 in place of the non-rotating tibial insert 4504. The rotating tibial insert may be coupled to the tibial tray 4502 in a manner similar to the non-rotating tibial insert 4504. To do so, the rotating tibial insert is positioned such that a stem of the rotating tibial insert is received in the cavity 4516 of the tibial tray 4504. Because the rotating tibial insert does not include the metal ring 4530 and rim 4532 of the non-rotating tibial insert 4504, the rotating tibial insert is free to rotate about an axis defined by the stem of the rotating tibial insert.

Figure 104:
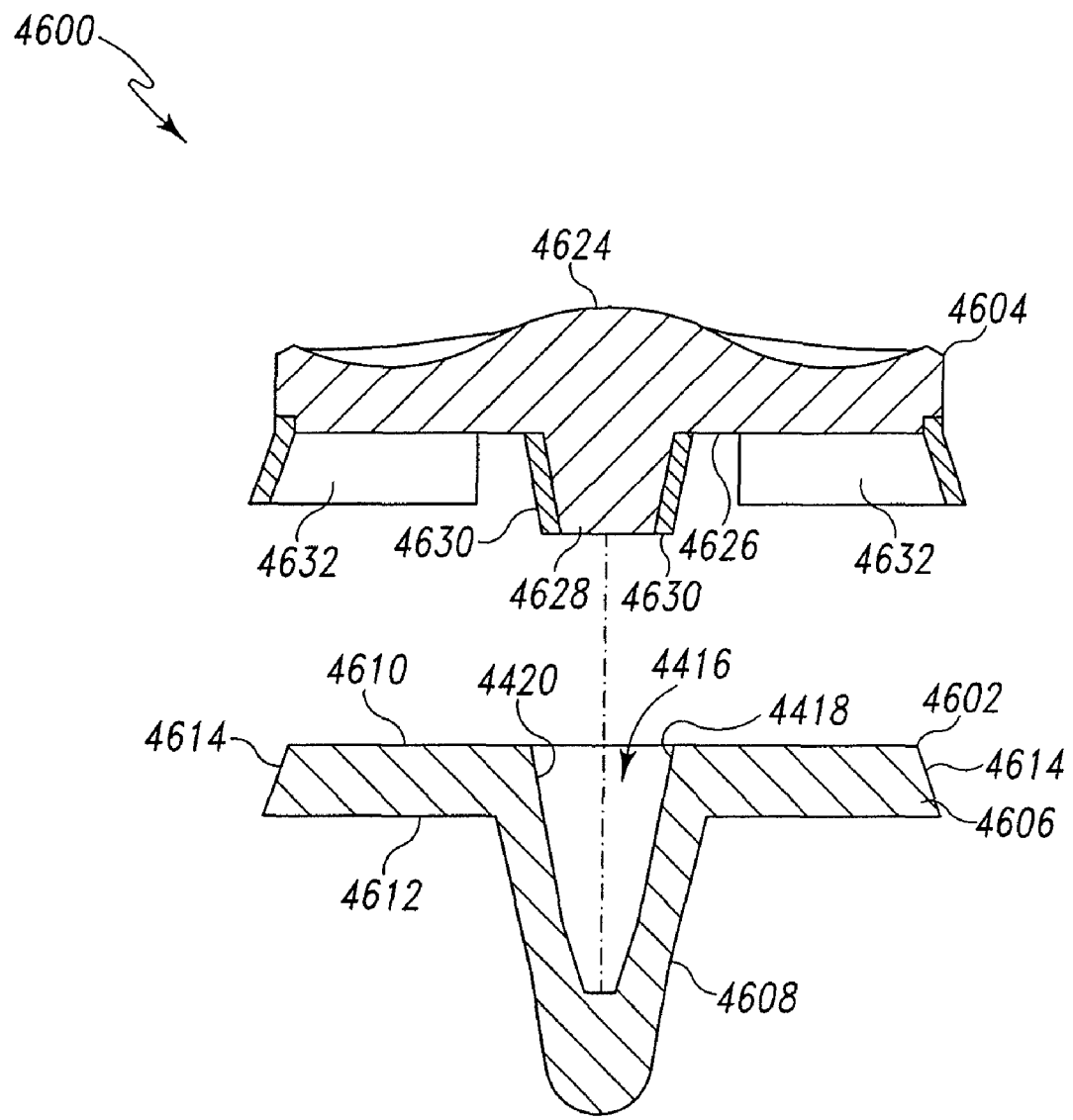
FIG. 104 is an exploded perspective view of another embodiment of the orthopaedic prosthesis assembly including a non-rotating tibial insert.
Figure 105:
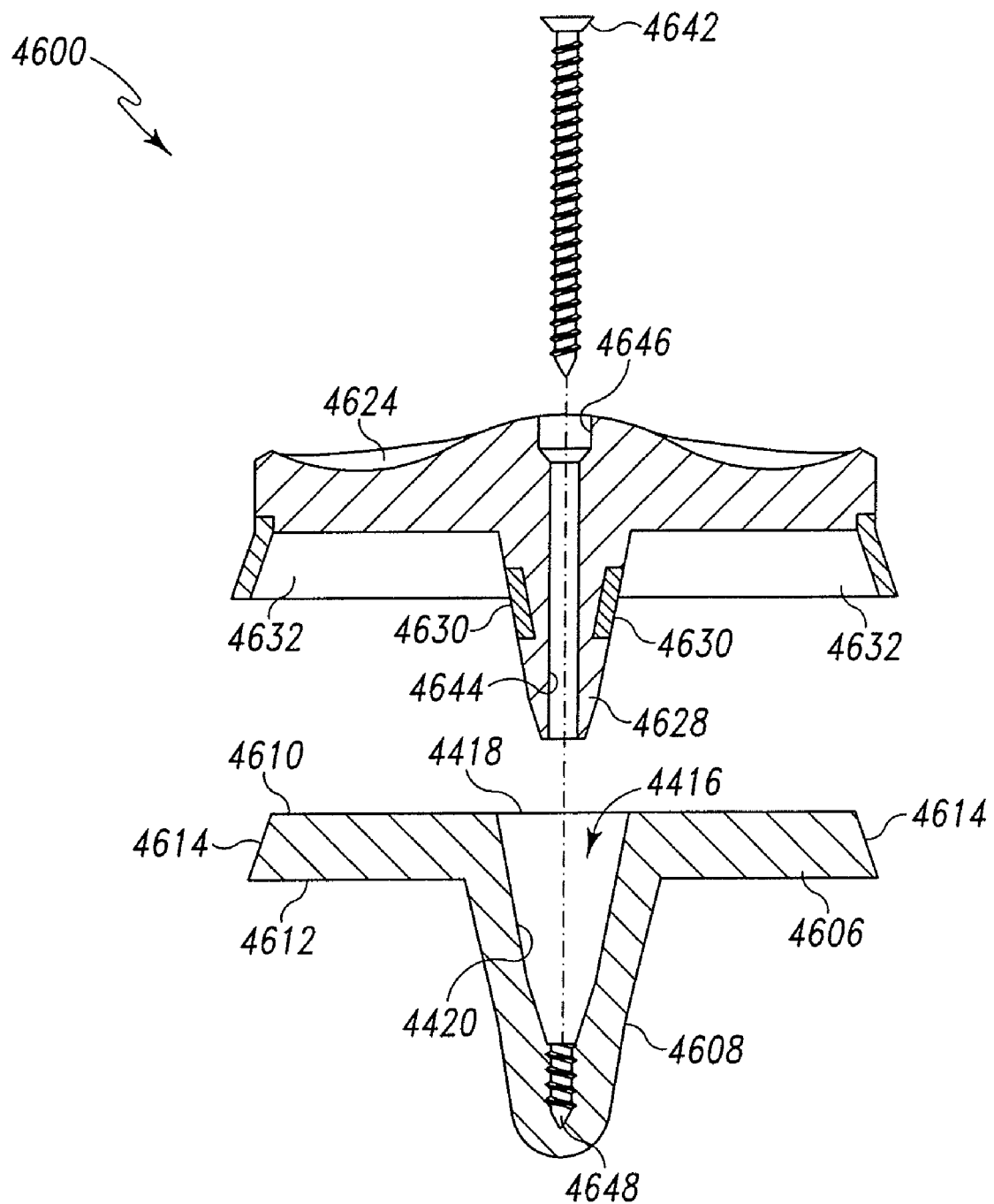
FIG. 105 is an exploded perspective view of another embodiment of an orthopaedic prosthesis assembly including a non-rotating tibial insert.
Figure 106:
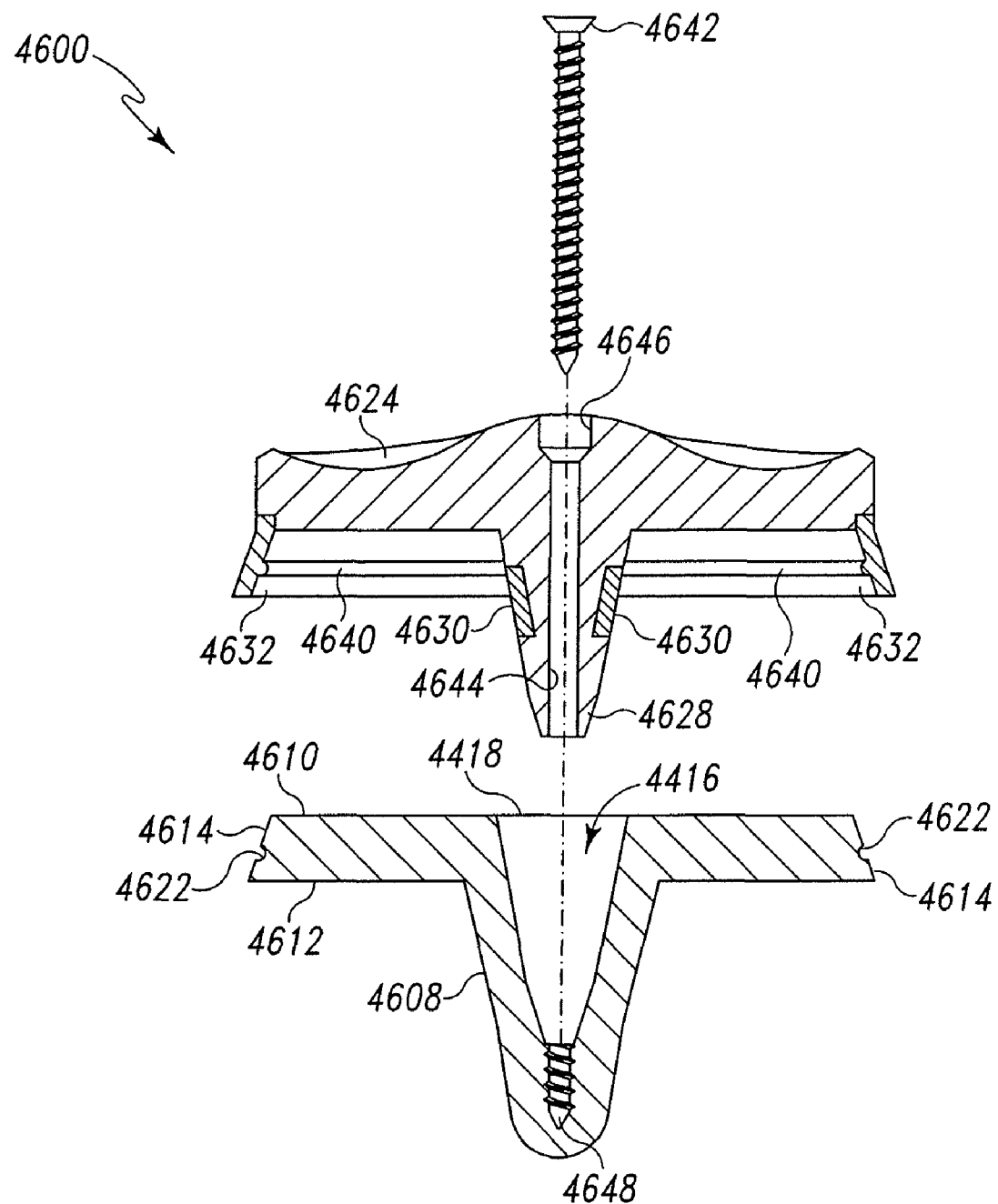
FIG. 106 is an exploded perspective view of another embodiment of the orthopaedic prosthesis assembly of FIG. 105.

Referring now to FIGS. 104-106, in another embodiment, a prosthetic knee system 4600 includes a tibial tray 4602, a fixed or non-rotating tibial insert 4604, and a rotating tibial insert (not shown). The rotating tibial insert may be similar to the rotating tibial insert 794 described above in regard to FIG. 87. The non-rotating tibial insert 4604 is illustratively formed from a polymer material, but may be formed from other materials, such as a ceramic material, a metallic material, a bio-engineered material, or the like, in other embodiments. Similarly, the tibial tray 4602 is illustratively formed from a metallic material, but may be formed from other materials, such as a ceramic material, a polymer material, a bio-engineered material, or the like, in other embodiments.

The tibial tray 4602 includes a platform 4606 and a stem 4608. The platform 4606 includes an upper surface 4610, a bottom surface 4612, and a side surface 4614 extending between the upper surface 4610 and the bottom surface 4612. The side surface 414 has an outwardly sloping taper. The stem 4608 extends downwardly from the bottom surface 4612 of the platform 4606. The tibial tray 4602 also includes a cavity 4616 having an opening 4618 defined in the upper surface 4610. The cavity 4616 is defined by an inner sidewall 4620 having an inwardly sloping taper. In some embodiments, such as the embodiment illustrated in FIG. 106, the platform 4606 may include a slot 4622 defined in the side surface 4614. In such embodiments, the slot 4622 may be defined along the length of the side surface 4614 and may define a closed path. However, in other embodiments, the slot 4622 may be embodied as a slot defining an open path, be defined only on particular sections of the side surface 4614, and/or be embodied as a number of smaller slots.

Again, as discussed with previous embodiments, the tibial tray 4602 is configured to be coupled to a surgically-prepared surface of the proximal end of a patient's tibia (not shown). When the tibial tray 4602 is so coupled, the stem 4608 is embedded in patient's tibia to thereby secure the tibial tray 4602 to the patient's bone. In some embodiments, a stem extension (not shown) may include coupled to the stem 4608 to increase the overall length of the stem 4608 and improve the stability of the tibial tray 4602 relative to the patient's bony anatomy.

The tibial insert 4604 includes an upper bearing surface 4624, a bottom surface 4626, and a stem 4628. The upper bearing surface 4624 is configured to contact a pair of natural or prosthetic femoral condyles of the patient. The stem 4628 extends downwardly from the bottom surface 4626 and includes a metal ring 4630 secured thereto. The metal ring 4630 has an inwardly sloping taper that corresponds to the taper of the inner sidewall 4620 of the tibial tray 4602. The tapers of the metal ring 4630 and the inner sidewall 4620 are designed such that when the non-rotating tibial insert 4604 is coupled to the tibial tray 4602, the metal ring 4630 and the inner sidewall 4620 contact each other and form a friction lock therebetween. In one particular embodiment, the tapers of the metal ring 4630 and the inner sidewall 4620 are embodied as corresponding Morse tapers. For example, in one particular embodiment, a Morse taper having a taper-per-foot in the range of about 0.59858 to about 0.63151 may be used. However, in other embodiments, other types of friction lock tapers may be used.

The non-rotating tibial insert 4604 also includes a rim or skirt 4632 extending downwardly from the bottom surface 4626 of the tibial insert 4604. The rim 4632 has an outwardly sloping taper that corresponds to the taper of the sidewall 4614 of the platform 4604 of the tibial tray 4602. The tapers of the rim 4632 and the sidewall 4614 are designed such that when the non-rotating tibial insert 4604 is coupled to the tibial tray 4602, the rim 4632 and sidewall 4614 contact each other and form a friction lock therebetween. In one particular embodiment, the tapers of the rim 4632 and the sidewall 4614 are embodied as corresponding Morse tapers. For example, in one particular embodiment, a Morse taper having a taper-per-foot in the range of about 0.59858 to about 0.63151 may be used. However, in other embodiments, other types of friction lock tapers may be used. Additionally, in embodiments wherein the sidewall 4614 of the platform 4606 includes the slot 4622, the rim 4632 may include a tab 4640 extending inwardly therefrom as illustrated in FIG. 106. The tab 4640 may define a closed path in some embodiments. Alternatively, the tab 4640 may be formed from a number of sections defined along the inside surface of the rim 4632.

The non-rotating tibial insert 4604 is configured to be coupled to the tibial tray 4602 in use. To do so, the tibial insert 4604 is positioned such that the stem 4628 is received in the cavity 4616 of the tibial tray 4602 and the rim 4632 encircles and contacts the side surface 4614 of the platform 4606 of the tibial insert 4604. As illustrated in FIGS. 105 and 106, the orthopaedic prosthesis assembly 4600 may also include a fastener 4642 in some embodiments. The fastener 4642 may be embodied as a screw or bolt. In such embodiments, the tibial insert 4604 includes an internal passageway 4644 extending therethrough. The passageway 4644 includes an opening 4646 in the upper bearing surface 4624. The cavity 4616 of the tibial insert 4604 includes a threaded aperture 4648 defined at a distal end of the cavity 4616. Once the non-rotating tibial insert 4604 is coupled to the tibial tray 4602, the fastener 4642 may be inserted into the internal passageway 4644 of the tibial insert 4604 and threaded into the threaded aperture 4648 of the tibial tray 4602 to thereby secure the tibial insert 4604 to the tibial tray 4602.

When the non-rotating tibial insert 4604 is coupled to the tibial tray 4602, the bottom surface 4626 of the tibial insert 4604 is in contact with the upper surface 4610 of the platform 4606 of the tibial tray 4602. In addition, the stem 4628 is received in the cavity 4616 of the tibial tray 4602 and, in some embodiments, the tab 4640 of the rim 4632 of the tibial insert 4604 is received in the slot 4622 defined in the side surface 4614 of the tibial tray 4602. As discussed above, the metal ring 4630 secured to the stem 4628 of the tibial insert 4604 is in contact with the inner sidewall 4620 of the tibial tray 4602 to form a friction lock therebetween. Additionally, the rim 4632 of the tibial insert 4604 is in contact with the sidewall 4614 of the platform 4606 to form another friction lock therebetween. The friction locks and the tab 4640 and slot 4622 (in some embodiments) cooperate to restrict or prevent rotation of the tibial insert 4604 relative to the tibial tray 4602, to reduce micro-motion between the tibial insert 4604 and the tibial tray 4602, and/or to prevent lift-off of the tibial insert 4604 relative to the tibial tray 4602.

A rotating tibial insert, similar to the tibial insert 794, may be used with the tibial tray 4602 in place of the non-rotating tibial insert 4604. The rotating tibial insert may be coupled to the tibial tray 4602 in a manner similar to the non-rotating tibial insert 4604. To do so, the rotating tibial insert is positioned such that a stem of the rotating tibial insert is received in the cavity 4616 of the tibial tray 4602. Because the rotating tibial insert create a friction lock with the tibial tray 4602, the rotating tibial insert is free to rotate about an axis defined by the stem of the rotating tibial insert.

Figure 107:
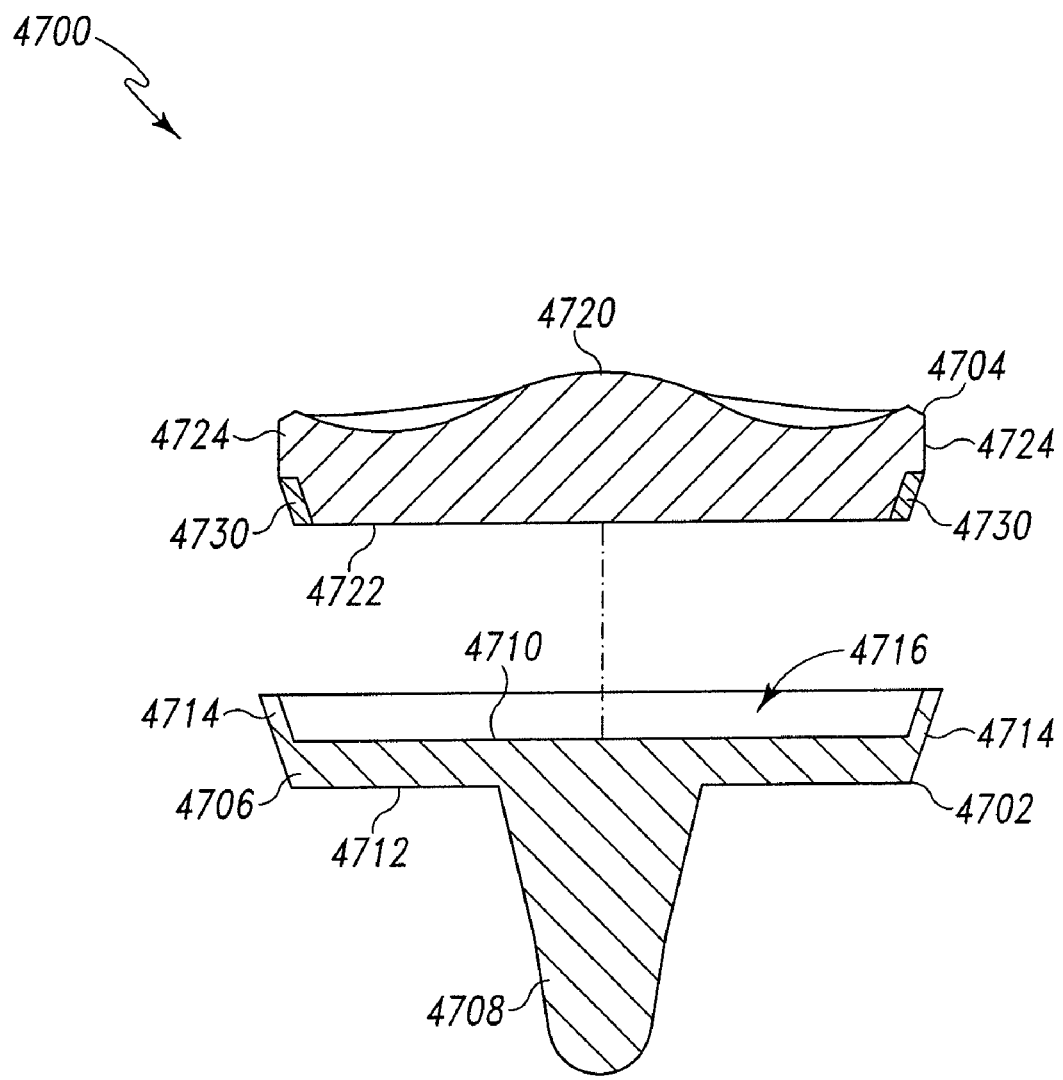
FIG. 107 is an exploded perspective view of another embodiment of an orthopaedic prosthesis assembly including a non-rotating tibial insert.

Referring now to FIG. 107, in another embodiment, a prosthetic knee system 4700 includes a tibial tray 4702 and a fixed or non-rotating tibial insert 4704. The tibial insert 4704 is illustratively formed from a polymer material, but may be formed from other materials, such as a ceramic material, a metallic material, a bio-engineered material, or the like, in other embodiments. Similarly, the tibial tray 4702 is illustratively formed from a metallic material, but may be formed from other materials, such as a ceramic material, a polymer material, a bio-engineered material, or the like, in other embodiments.

The tibial tray 4702 includes a platform 4706 and a stem 4708. The platform 4706 includes an upper surface 4710 and a bottom surface 4712. The stem 4708 extends downwardly from the bottom surface 4712 of the platform 4706. The platform 4706 includes a rim 4714 extending upwardly from the upper surface 4710. The rim 4714 has an inwardly sloping taper. Illustratively, the rim 4714 is defined along the periphery of the upper surface 4710 and defines an inner recessed area 4716. The illustrative rim 4714 also defines a closed path. However, in other embodiments, the rim 4714 may be embodied as a number rim sections and/or otherwise not extend the entirety of the periphery of the upper surface 4710.

Again, as discussed with previous embodiments, the tibial tray 4702 is configured to be coupled to a surgically-prepared surface of the proximal end of a patient's tibia (not shown). When the tibial tray 4702 is so coupled, the stem 4708 is embedded in patient's tibia to thereby secure the tibial tray 4702 to the patient's bone. In some embodiments, a stem extension (not shown) may include coupled to the stem 4708 to increase the overall length of the stem 4708 and improve the stability of the tibial tray 4702 relative to the patient's bony anatomy.

The non-rotating tibial insert 4704 includes an upper bearing surface 4720, a bottom surface 4722, and a side surface 4724 extending between the upper bearing surface 4720 and the bottom surface 4722. The upper bearing surface 4720 is configured to contact a pair of natural or prosthetic femoral condyles of the patient. The tibial insert 4704 also includes a metal ring 4730 secured to the side surface 4724. The metal ring 4730 is configured and positioned such that an outer surface 4732 of the metal ring 4730 is planar with the side surface 4724 of the tibial insert 4704 and a bottom surface 4734 of the metal ring 4730 is planar with the bottom surface 4734 of the tibial insert 4704. The metal ring 4730 has an inwardly sloping taper that corresponds to the taper of the rim 4714 of the tibial tray 4702. The tapers of the metal ring 4730 and the rim 4714 are designed such that when the non-rotating tibial insert 4704 is coupled to the tibial tray 4702, the metal ring 4730 and the rim 4714 contact each other and form a friction lock therebetween. In one particular embodiment, the tapers of the metal ring 4730 and the rim 4714 are embodied as corresponding Morse tapers. For example, in one particular embodiment, a Morse taper having a taper-per-foot in the range of about 0.59858 to about 0.63151 may be used. However, in other embodiments, other types of friction lock tapers may be used.

The tibial insert 4704 is configured to be coupled to the tibial tray 4702 in use. To do so, the tibial insert 4704 is positioned such that a portion thereof is received in the inner recessed area 4716 of the tibial tray 4702. When so positioned, the bottom surface 4722 of the tibial insert 4704 is in contact with the upper surface 4710 of the platform 4706 of the tibial tray 4702. In addition, the rim 4714 of the tibial tray 4702 contacts the metal ring 4730 of the tibial insert 4704 and forms a friction lock therebetween. The friction lock restricts or prevents rotation of the tibial insert 4704 relative to the tibial tray 4702, reduces micro-motion between the tibial insert 4704 and the tibial tray 4702, and/or prevents lift-off of the tibial insert 4704 relative to the tibial tray 4702.

Figure 108:
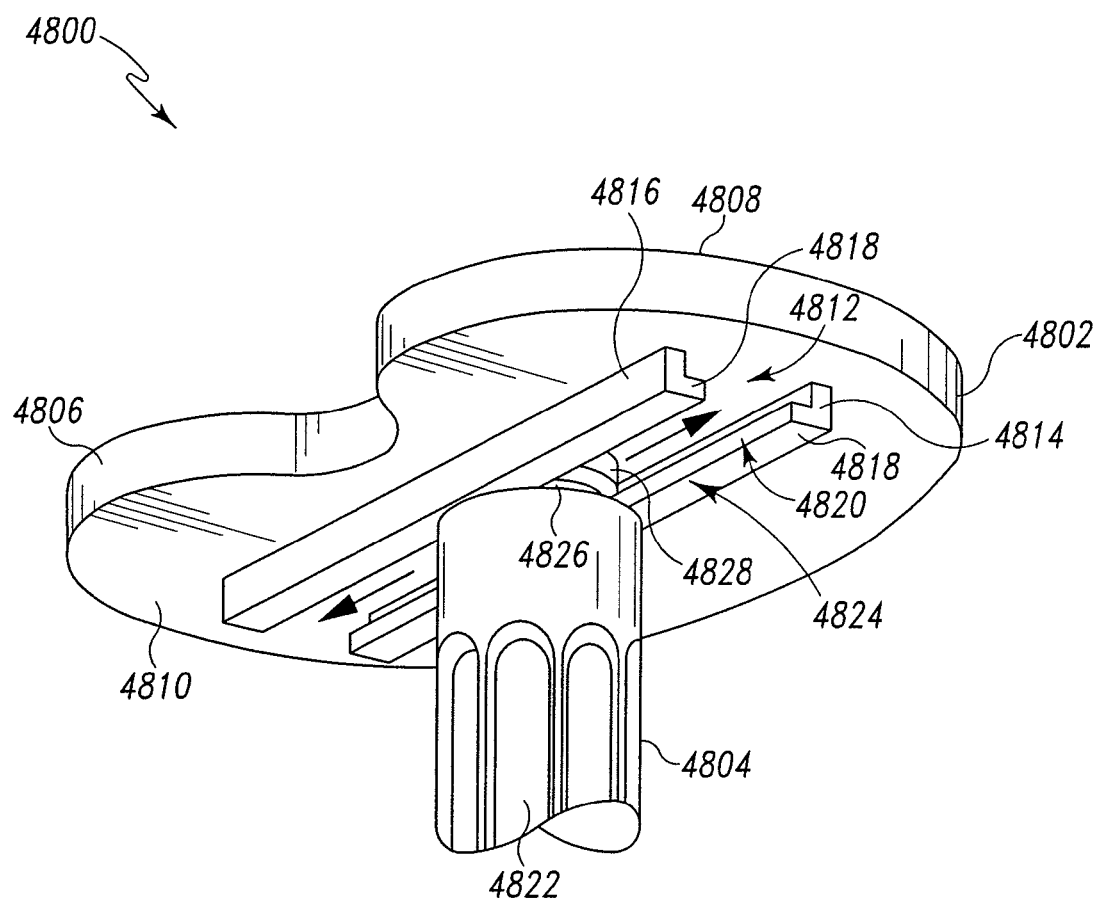
FIG. 108 is a bottom perspective view of an orthopaedic prosthesis assembly including a tibial tray and an adjustable stem.

Referring now to FIG. 108, in another embodiment, a prosthetic knee system 4800 includes a tibial tray 4802 and an adjustable stem 4804. The tibial tray 4802 and adjustable stem 4804 are illustratively formed from an implantable metallic material, but may be formed from other materials, such as a ceramic material, a polymer material, a bio-engineered material, or the like, in other embodiments.

The tibial tray 4802 includes a platform 4806 having an upper surface 4808 and a bottom surface 4810. The tibial tray 4802 also includes a guide track 4812 that extends downwardly from the bottom surface 4810 of the tibial tray 4802. Illustratively, the guide track 4812 extends across the bottom surface of the platform 4806 in the medial/lateral direction, but may extend in other directions in other embodiments. The guide track 4812 includes an anterior sidewall 4814 and a posterior sidewall 4816. Each of the sidewalls 4814, 4816 include a respective lip 4818 extending inwardly therefrom to define an opening 4820 therebetween.

The stem 4804 includes an elongated shaft 4822 and a mounting end 4824 defined on a proximal end of the elongated shaft 4822. The mounting end 4824 includes a neck 4826 and a flange 4828 defined at an end of the neck 4826. The flange 4828 is sized to be received in the opening 4820 of the guide track 4812. That is, the stem 4804 may be coupled to the tibial tray 4802 by positioning the stem 4804 such that the flange 4828 of the mounting end 4824 is received in the guide track 4812 and the neck 4826 of the mounting end 4824 is positioned in the opening 4820 defined between the lips 4818. The stem 4804 may then be slid or otherwise positioned to the desired location along the guide track 4812. Once positioned in the desired location, the stem 4804 may be secured to the tibial tray 4802 via use of a fastener or via compression of the flange 4828 against the elongated shaft 4822 of the stem 4804. That is, the distance between the flange 4828 and the base of the neck 4826 may be adjustable by, for example, screwing or threading the mounting end 4824 into a threaded aperture (not shown) defined in the end of the elongated shaft 4822.

Figure 109:
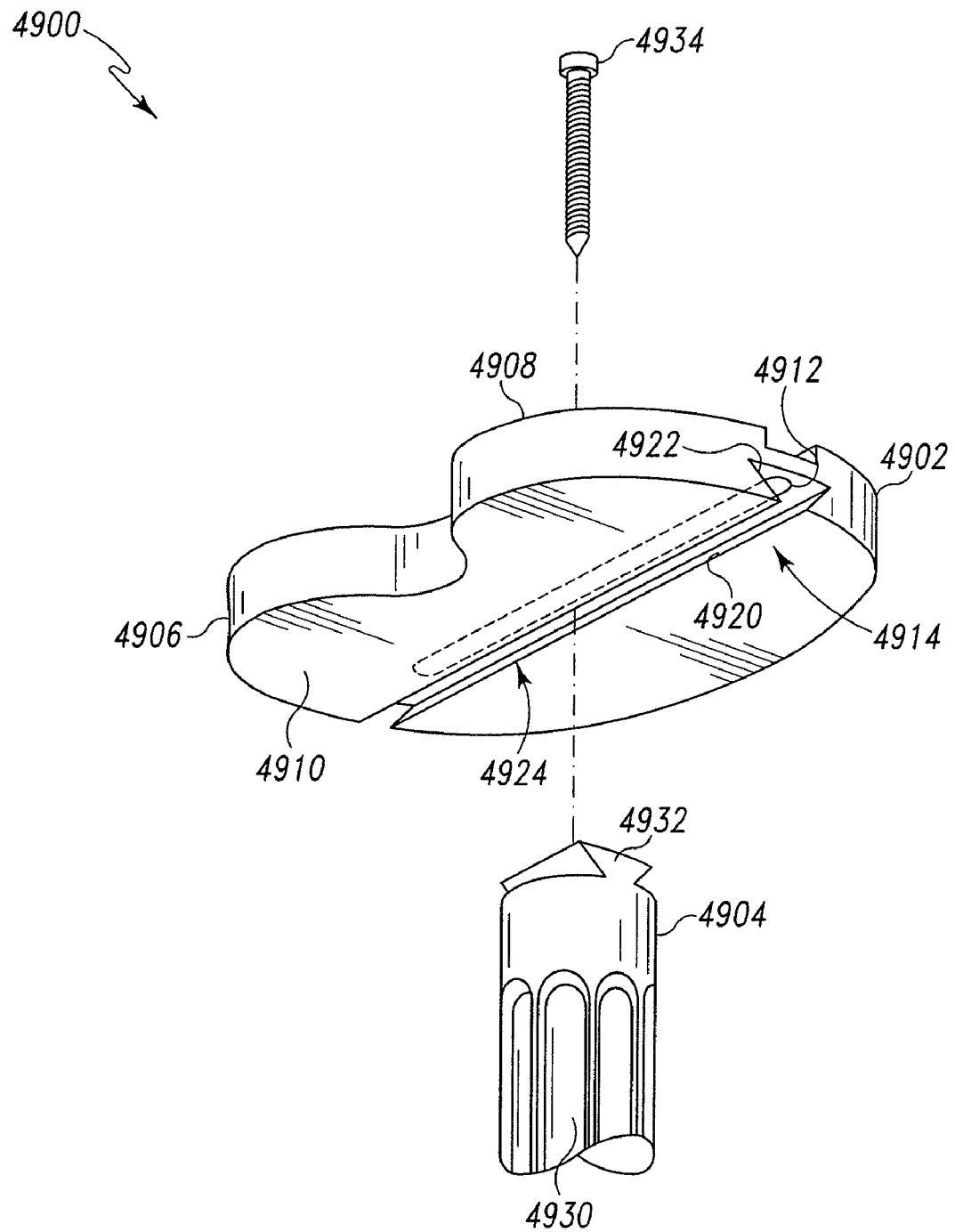
FIG. 109 is a bottom perspective view of another embodiment of the orthopaedic prosthesis assembly of FIG. 108.
Figure 110:
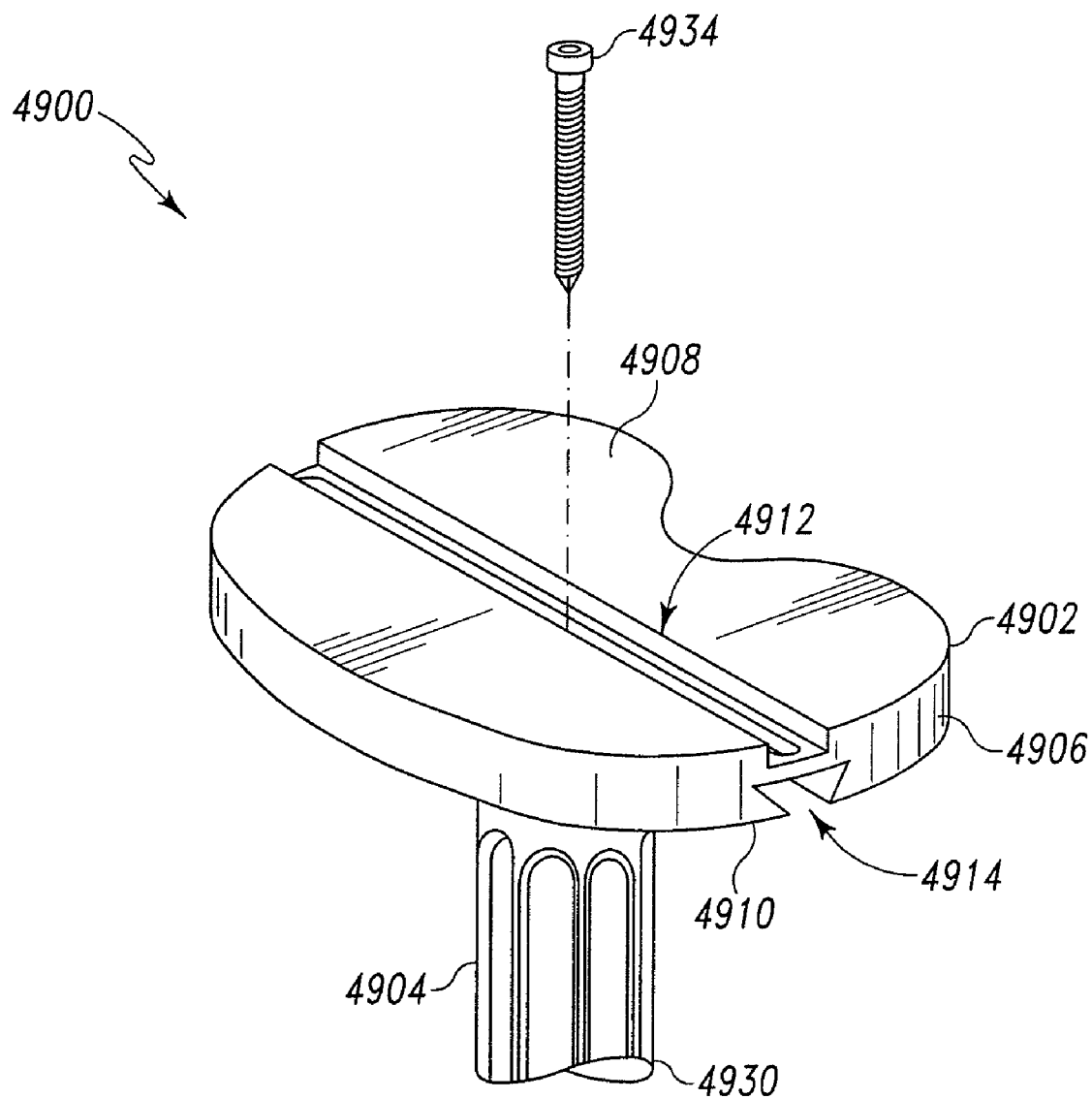
FIG. 110 is a top perspective view of the orthopaedic prosthesis assembly of FIG. 109.
Figure 111:
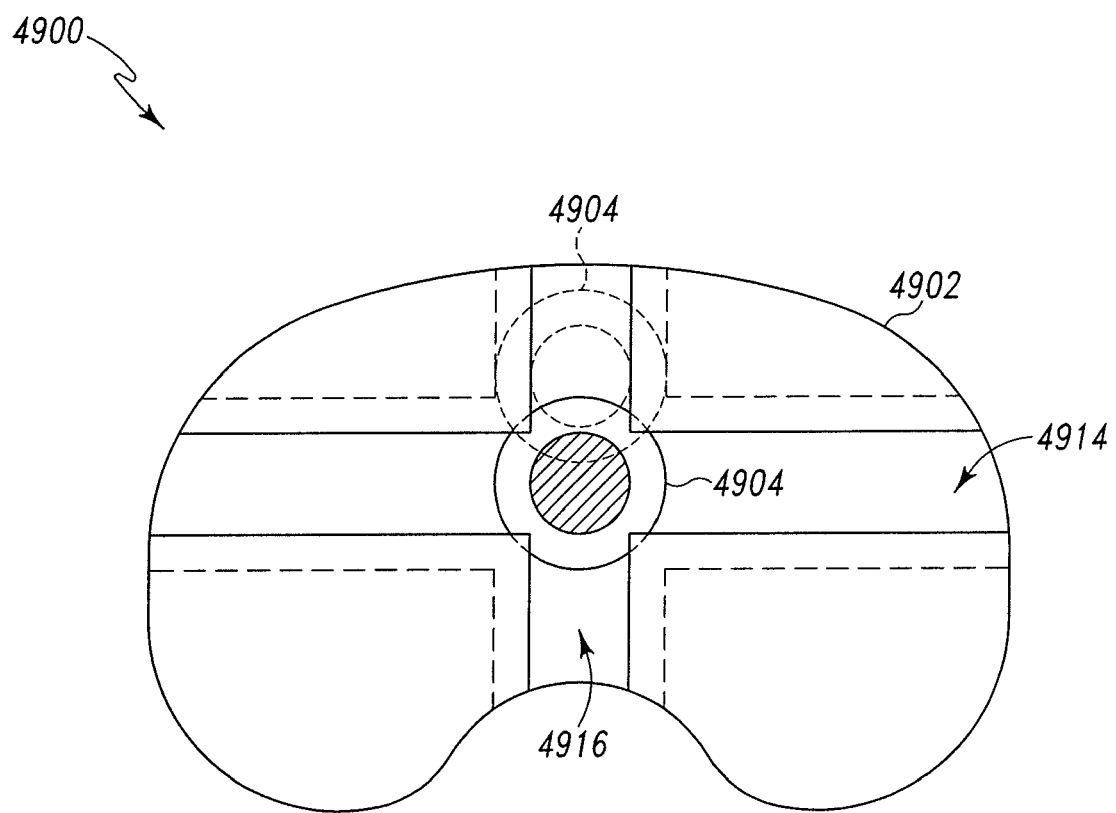
FIG. 111 is a bottom plan view of another embodiment of the orthopaedic prosthesis assembly of FIG. 109.

Referring now to FIGS. 109-111, in another embodiment, a prosthetic knee system 4900 includes a tibial tray 4902 and an adjustable stem 4904. The tibial tray 4902 and adjustable stem 4904 are illustratively formed from an implantable metallic material, but may be formed from other materials, such as a ceramic material, a polymer material, a bio-engineered material, or the like, in other embodiments.

The tibial tray 4902 includes a platform 4906 having an upper surface 4908 and a bottom surface 4910. The tibial tray 4902 also includes a recessed elongated opening 4912 in the upper surface 4908 and a recessed guide track 4914 in the bottom surface 4910. The guide track 4914 is defined in the bottom surface 4910 in a medial/lateral direction, but may be defined in other directions in other embodiments. Additionally, although the illustrative tibial tray 4902 includes a single guide track 4914, the tibial tray 4902 may include additional guide tracks in other embodiments. For example, as illustrated in FIG. 111, the tibial tray 4902 may include a guide track 4916 that is defined in the bottom surface 4910 in an anterior/posterior direction such that the position of the stem 4904 relative to the tibial tray 4902 may be configured in either a medial/lateral direction or an anterior/posterior direction The illustrative guide track 4914 is substantially dovetailed and is configured to receive a portion of the stem 4902. The guide track 4914 includes an anterior sidewall 4920 and a posterior sidewall 4922. The sidewalls 4920, 4922 are inwardly sloped to define an opening 4924 in the bottom surface 4910 therebetween. However, in other embodiments, the guide track 4914 may have other shapes such as a substantially rectangular shape. The illustrative guide track 4914 is an open track having open ends. However, in other embodiments, the guide track 4914 may be a closed track having one or both ends closed.

The stem 4904 includes an elongated shaft 4930 and a mounting end 4932 defined on a proximal end of the elongated shaft 4930. The mounting end 4932 has a shape corresponding to the shape of the guide track 4914 such that the mounting end 4932 may be received therein. In the illustrative embodiments of FIGS. 109 and 110, the mounting end 4932 has a substantially dovetail shape, but may have other shapes corresponding to the shape of the guide track 4914 in other embodiments. The mounting end 4932 is sized to be received in the guide track 4914. Once so received, the stem 4904 may then be slid or otherwise positioned to the desired location along the guide track 4914. Once positioned in the desired location, the stem 4904 may be secured to the tibial tray 4902 via use of a fastener 4934, which may be inserted through the elongated opening 4912 defined in the upper surface 4908 of the tibial tray 4902. Because the elongated opening 4912 is recessed in the upper surface 4908, the head of the fastener 4934 is positioned at or below the upper surface 4908.

Figure 112:
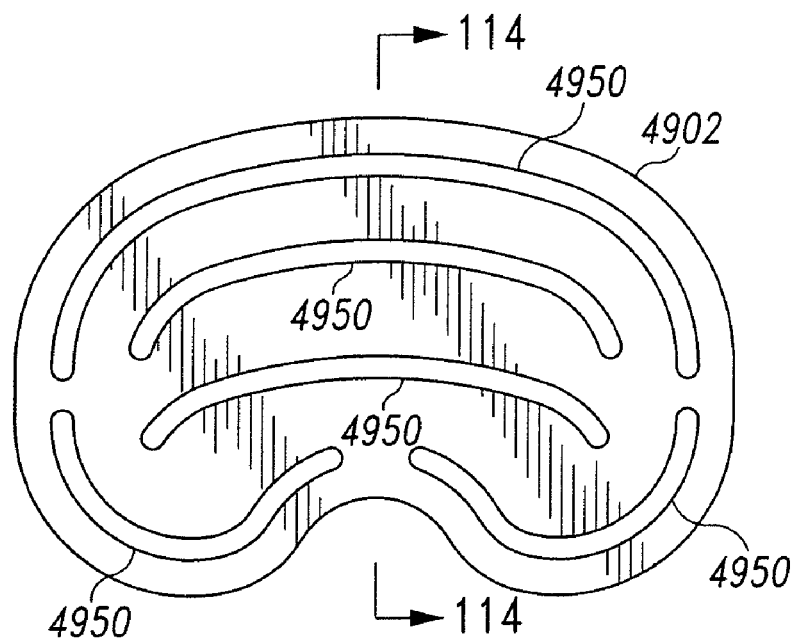
FIG. 112 is a top plan view of one embodiment of a tibial tray.

Referring now to FIGS. 112-117, in other embodiments, the tibial tray 4902 may include a number of recessed elongated openings 4950 in place of the guide track 4914. As illustrated in FIG. 112, the openings 4950 are defined in the upper surface 4908 of the platform 4906. Illustratively, each opening 4950 is curved, which allows for stem placement in both the anterior/posterior and medial/lateral directions. Although the illustrative tibial tray 4902 includes five recessed elongated openings 4950, it should be appreciated that in other embodiments, any number of elongated openings 4950 may be used. Additionally, the direction, curvature, and overall configuration of each recessed elongated opening 4950 may be modified based on the particular application and/or implementation.

Figure 114:
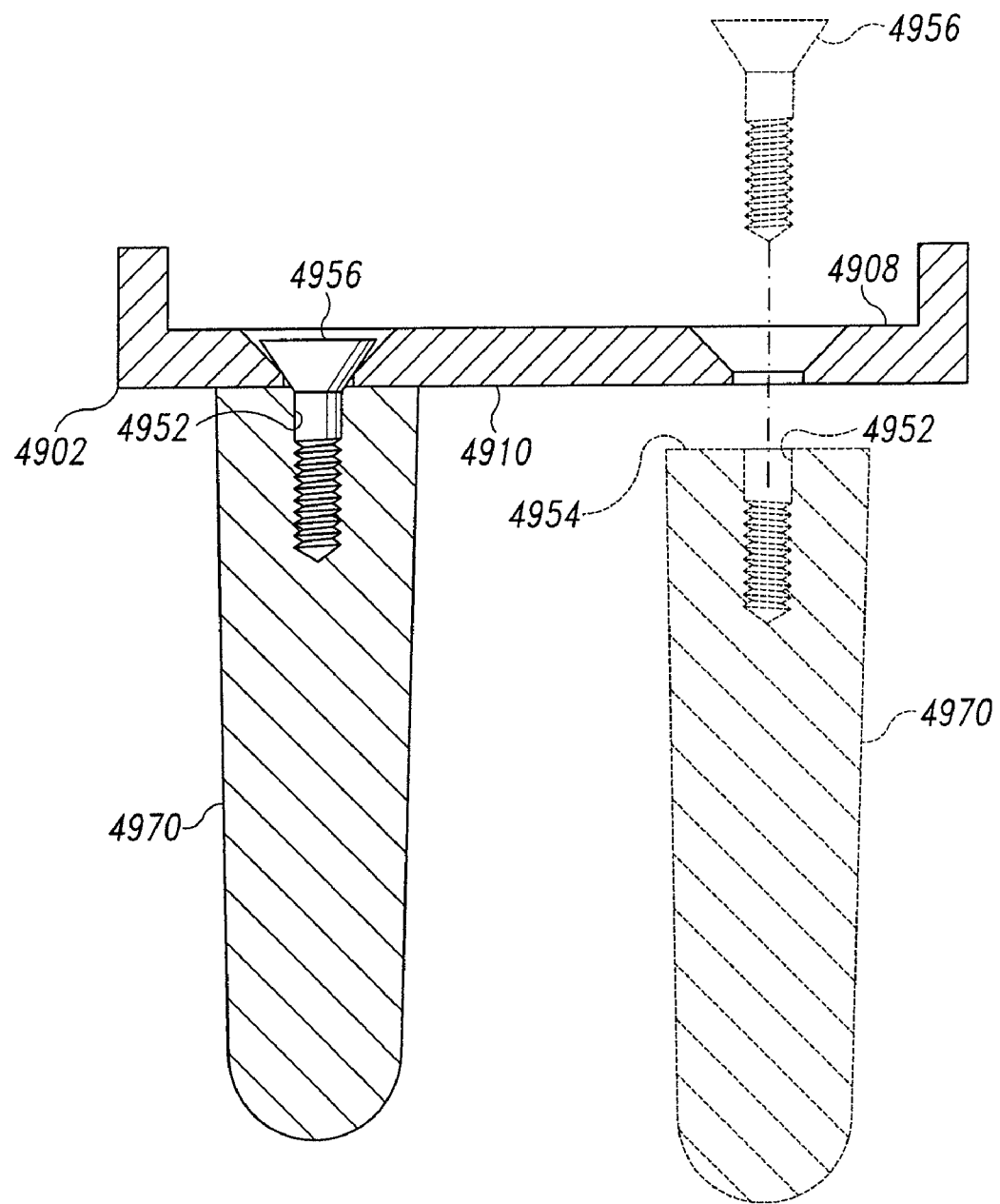
FIG. 114 is a cross-sectional view of the tibial tray of FIG. 112 taken along the line 114-114 and including a stem secured thereto.

As shown in FIG. 114, the number of elongated openings 4950 allow a stem 4970 to be positioned in any one of a number of locations. The stem 4970 includes a threaded aperture 4952 defined in a mounting end 4954. The stem 4970 may be secured to the tibial tray 4902 by positioning a fastener 4956 in the elongated opening 4950 and threading the fastener 4956 into the threaded aperture 4952 as illustrated in FIG. 114. As discussed above, the elongated openings 4950 are recessed such that the head of the fastener 4956 is at or below the upper surface 4908 when the stem 4970 is secured to the tibial tray 4902. As shown in FIG. 115, each opening 4950 may be defined by inwardly sidewalls 4960. As illustrated in FIG. 116, the stem 4970 may be secured to the tibial tray 4902 at a desired angle relative to the tibial tray 4902 via use of a shim 4962. The angle of attachment may be selected based on the thickness of the shim 4962. In other embodiments, the sidewalls 4960 defining the opening 4950 are curved such that a fastener 4964 having a curved head may be used to secure the stem 4970 to the tibial tray 4902 in an angled position as illustrated in FIG. 117. In such embodiments, the mounting end 4954 of the stem 4970 may have a corresponding slope.

Figure 113:
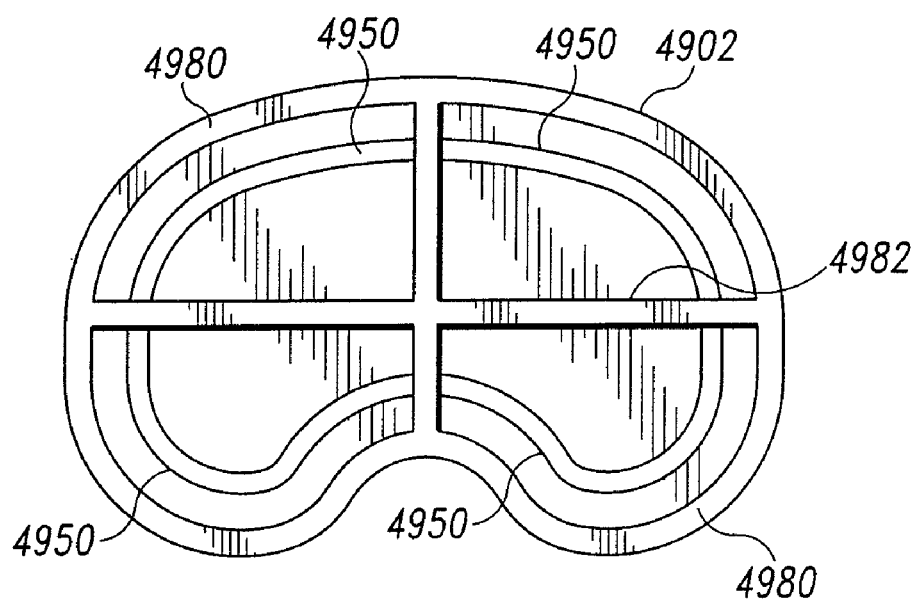
FIG. 113 is a top plan view of another embodiment of the tibial tray of FIG. 112.

In some embodiments, the tibial tray 4902 may include an upwardly extending sidewall 4980 about the periphery of the upper surface 4908 as illustrated in FIG. 113. In such embodiments, the tibial tray 4902 may include a number of cross-members 4982 secured to the sidewall 4980. The number of cross-members 4982 may extend across the upper surface 4908 of the tibial tray 4902 to provide an increased rigidity to the tibial tray 4902. It should also be appreciated that the sidewall 4980 may extend downwardly from the bottom surface 4910 of the tibial tray 4902 in other embodiments.

Figure 118:
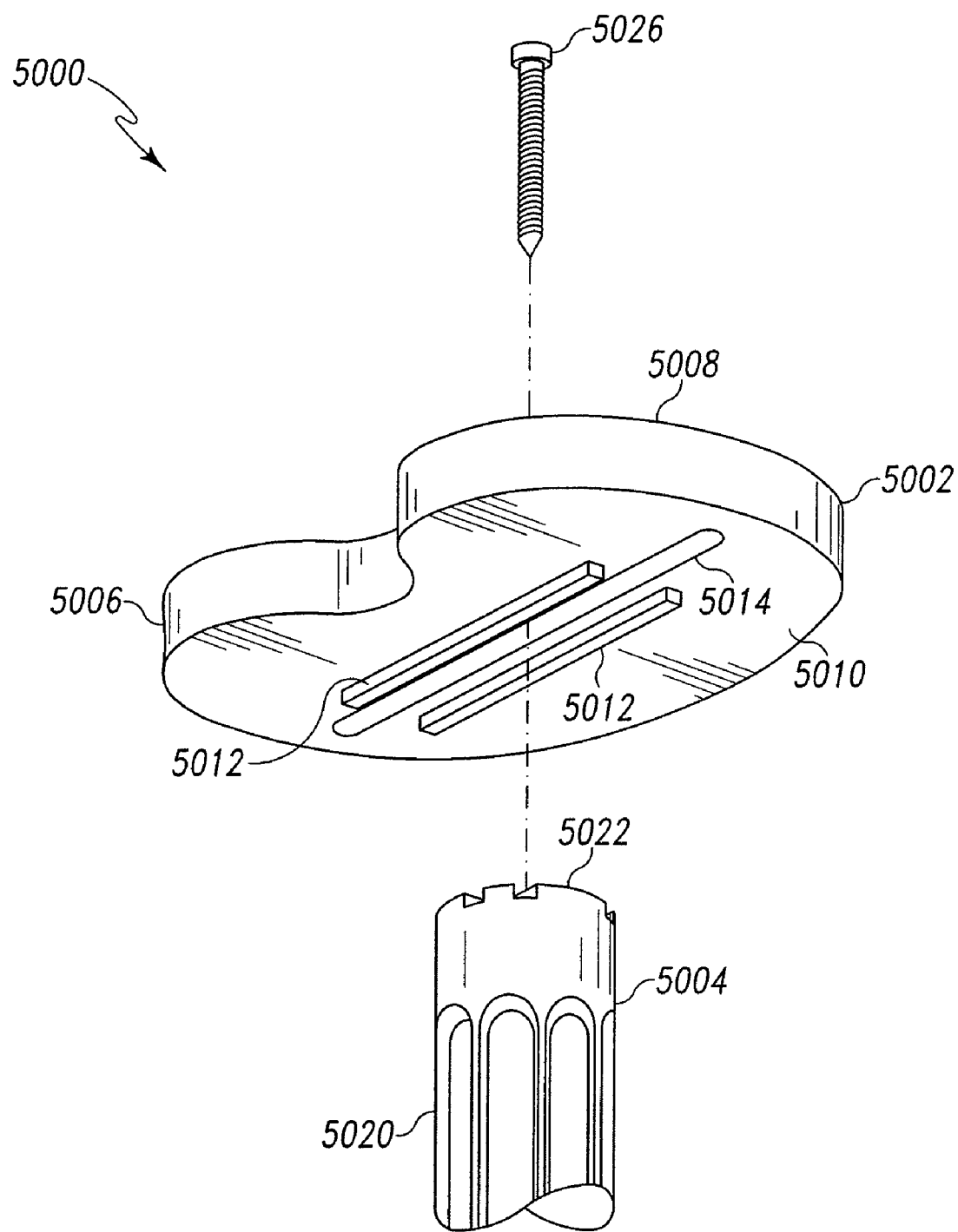
Figure 119:
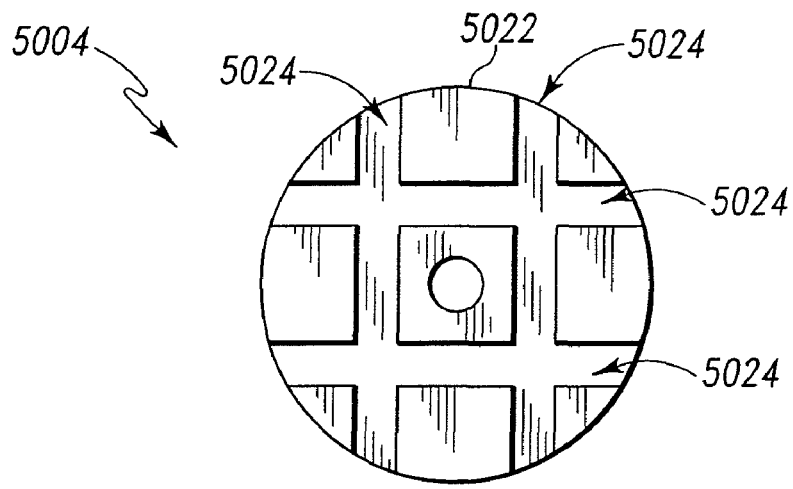
Figure 120:
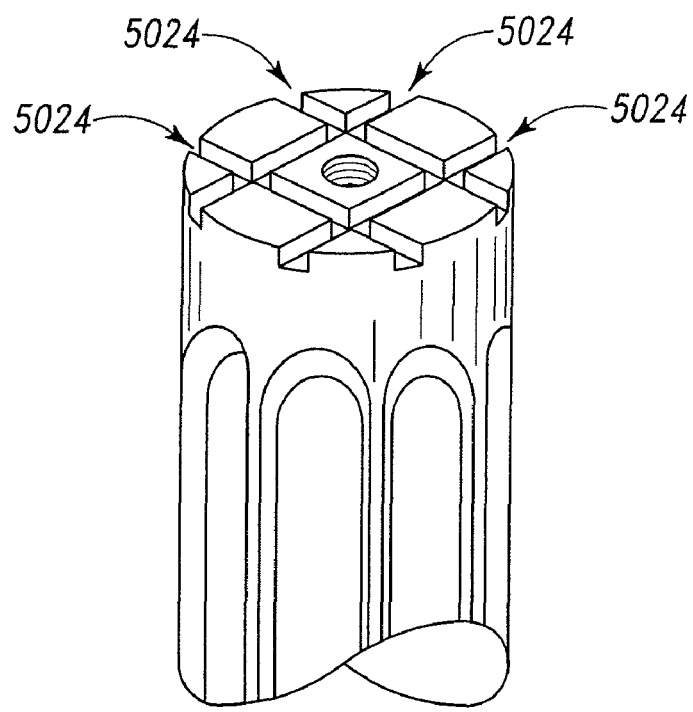

Referring now to FIGS. 118-120, in another embodiment, a prosthetic knee system 5000 includes a tibial tray 5002 and an adjustable stem 5004. The tibial tray 5002 and adjustable stem 5004 are illustratively formed from an implantable metallic material, but may be formed from other materials, such as a ceramic material, a polymer material, a bio-engineered material, or the like, in other embodiments.

The tibial tray 5002 includes a platform 5006 having an upper surface 5008 and a bottom surface 5010. The tibial tray 5002 includes a pair of guide rails 5012 extending downwardly from the bottom surface 5010. Additionally, the tibial tray 5002 includes an elongated opening 5014 defined in the upper surface 5008 between the guide rails 5012. Illustratively, the guide rails 5012 extend across the bottom surface 5008 of the platform 5006 in the medial/lateral direction, but may extend in other directions in other embodiments. The guide rails 5012 have a substantially rectangular shape, but may have other shapes in other embodiments.

The stem 5004 includes an elongated shaft 5020 and a mounting end 5022 defined on a proximal end of the elongated shaft 5020. The mounting end 5022 includes a number of grooves 5024 defined therein. The grooves 5024 are configured to receive the guide rails 5012 of the tibial tray 5002. That is, the grooves 5024 have a shape and a separation distance corresponding to the guide rails 5012. Illustratively, as shown in FIGS. 119 and 120, the stem 5004 includes two pairs of grooves 5024 such that the stem 5004 may be coupled to the tibial tray 5002 in a number of orientations. To do so, the stem 5004 is positioned such that the rails 5012 are received in the desired pair of grooves 5024. The stem 5004 may then be slid or otherwise positioned to the desired location along the guide rails 5012. Once positioned in the desired location, the stem 5004 may be secured to the tibial tray 5002 via use of a fastener 5026, which may be inserted through the elongated opening 5014 defined in the upper surface 5008 of the tibial tray 5002. Because the elongated opening 5014 is recessed in the upper surface 5008, the head of the fastener 5026 is positioned at or below the upper surface 5008.

Figure 121:
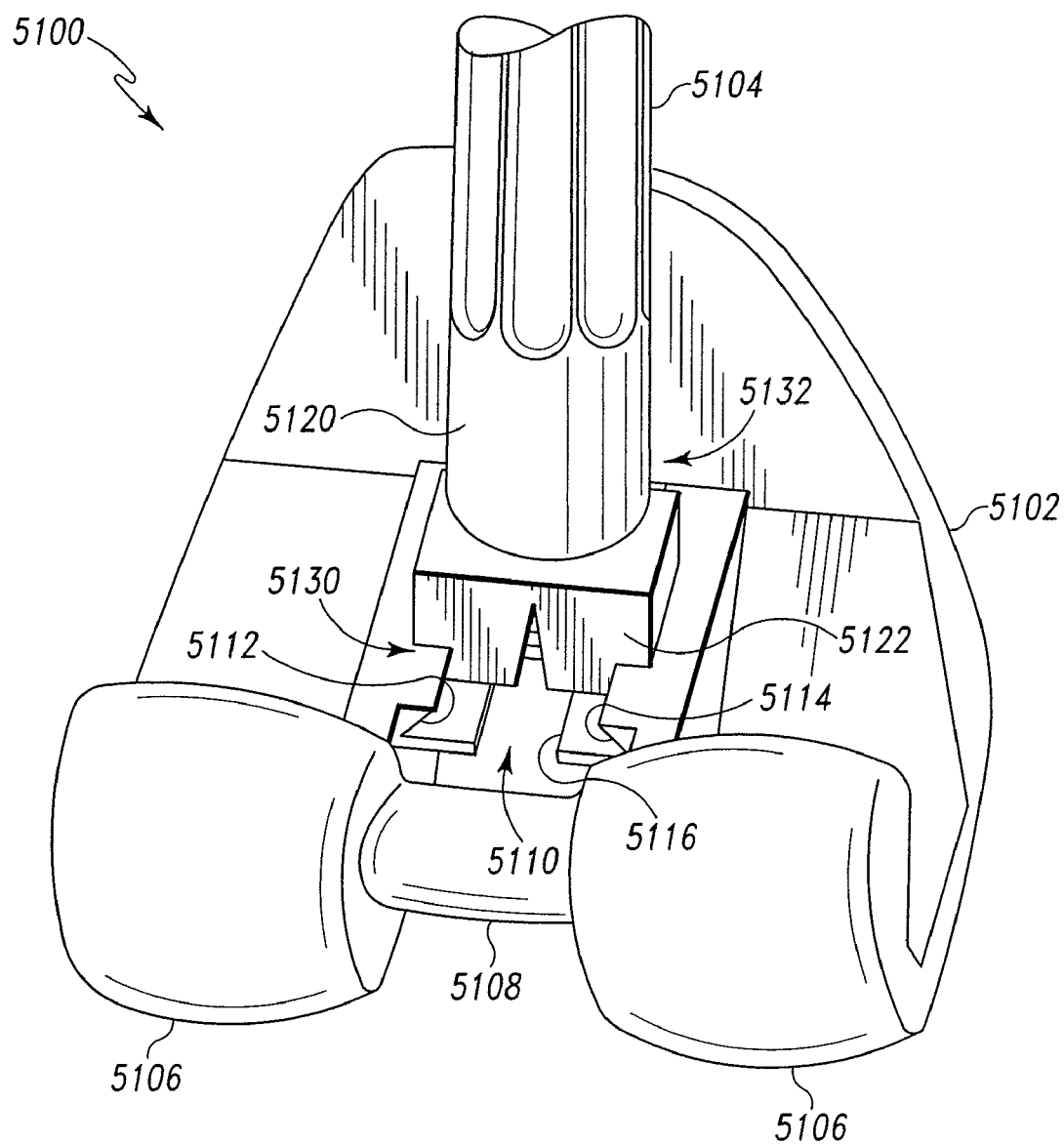
Figure 122:
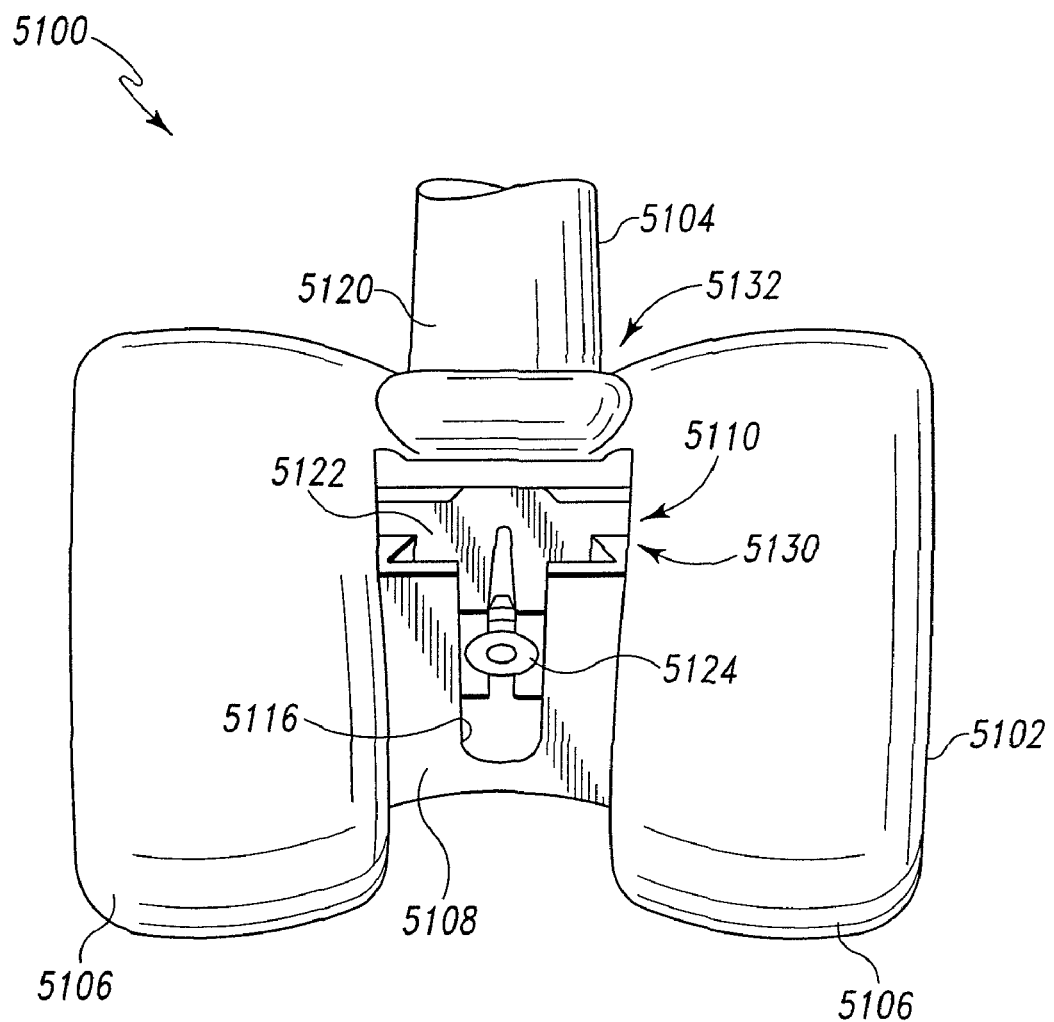

Referring now to FIGS. 121 and 122, in another embodiment, a prosthetic knee system 5100 includes a femoral component 5102, an stem 5104, and an adaptor 5122 coupled to the femoral component 5102 and the stem 5104. The femoral component 5102, the stem 5104, and the adaptor 5122 are illustratively formed from an implantable metallic material, but may be formed from other materials, such as a ceramic material, a polymer material, a bio-engineered material, or the like, in other embodiments.

The femoral component 5102 is configured to be coupled to a surgically-prepared surface of the distal end of a patient's femur (not shown). When the femoral component 5102 is coupled to the patient's femur and the stem 5104 and the adaptor 5122 are coupled to the femoral component 5102 as discussed below, the stem 5104 is embedded in the patient's bone. The femoral component 5102 may be secured to the patient's femur via use of bone adhesive or other attachment means. The femoral component 5102 includes a pair of condyles 5106. In use, the condyles 5106 replace the natural condyles of the patient's femur and are configured to articulate on the proximal end of the patient's natural or surgically-prepared tibia.

The femoral component 5102 includes a platform 5108 defined between the condyles 5106. The platform 5108 includes a guide track 5110 defined therein. The illustrative guide track 5110 is substantially dovetailed and is configured to receive a portion of the adaptor 5122. The guide track 5110 includes an anterior sidewall 5112 and a posterior sidewall 5114. The sidewalls 5112, 5114 are inwardly sloped to define an opening 5116 in the platform 5108 therebetween. However, in other embodiments, the guide track 5110 may have other shapes such as a substantially rectangular shape. The illustrative guide track 5110 is an open track having open ends. However, in other embodiments, the guide track 5110 may be a closed track having one or both ends closed.

The adaptor 5122 includes a mounting end 5130 configured to be received in the guide track 5110. That is, the mounting end 5130 has a shape corresponding to the shape of the guide track 5110 such that the mounting end 5130 may be received therein. In the illustrative embodiments of FIGS. 121 and 122, the mounting end 5130 has a substantially dovetail shape, but may have other shapes corresponding to the shape of the guide track 5110 in other embodiments. The mounting end 5130 of the adaptor 5122 is sized to be received in the guide track 5110. Once so received, the adaptor 5122 (and the stem 5104) may be slid or otherwise positioned to the desired location along the guide track 5110. Once positioned in the desired location, the adaptor 5122 may be secured to the femoral component 5102 via use of a fastener 5124, which may be inserted through the opening 5116 defined in the platform 5108 of the femoral component 5102.

In some embodiments, the adaptor 5122 is integral with the stem 5104. However, in other embodiments, the adaptor 5122 is separate from the stem 5104. In such embodiments, the adaptor 5122 includes a mounting end 5132 that is configured to be coupled to the stem 5104. For example, in some embodiments, the mounting end 5132 may include a threaded aperture (not shown) configured to receive a threaded stud (not shown) defined on the end of the stem 5104. Alternatively, the mounting end 5132 may include a threaded stud configured to be received in a threaded aperture defined in the end of the stem 5104. Regardless, in such embodiments, the stem 5104 is removably coupleable to the adaptor 5122 via the mounting end 5132. It should be appreciated that in such embodiments, the adaptor 5122 may also be used with other orthopaedic prostheses. For example, the adaptor 5122 may be used with the tibial tray 4902 illustrated in and described above in regard to FIG. 110. That is, the mounting end 5130 of the adaptor 5122 may be positioned in the guide track 4914 and secured to the tibial tray 4902 via the fastener 4934 or other securing device. The stem 5104 or other stem may then be secured to the mounting end 5132 of the adaptor as discussed above. In this way, the adaptor 5122 may be selectively used with a tibial tray or a tibial insert to facilitate the coupling of a stem thereto.

While many prosthetic knee systems and assemblies described above include a single tibial tray, non-rotating or fixed tibial insert, and rotating tibial insert, it is within the scope of this disclosure to include other prosthetic knee systems having one or more tibial trays, one or more tibial inserts, and/or one or more locking mechanisms or other components associated with the aforementioned tray(s) and insert(s). A first combination of the components of such a prosthetic knee system provides a rotating tibial assembly whereby the tibial insert is able to rotate about an axis relative to the tibial tray. A second combination of the components such a prosthetic knee system provides a non-rotating or fixed knee assembly whereby the tibial insert is fixed relative to the tibial tray and is not able to rotate about the axis. As such, it is within the scope of this disclosure to include other prosthetic knee systems including components which may be arranged to provide for both a rotating knee assembly and a non-rotating knee assembly.

Many different features are disclosed within FIGS. 1-122 herein in order to couple various tibial trays and tibial inserts together in order to prevent rotation of the tibial insert relative to the tibial tray, to reduce or minimize micro-motion between the tibial insert and the tibial tray, and/or to prevent lift-off of the tibial insert relative to the tibial tray, for example. These features may be located on or within each tibial insert and/or tibial tray. Alternatively, these features may be embodied by components separate from the tibial insert and tibial trays disclosed herein. Regardless, it is within the scope of this disclosure for any one or more of these features to be used in combination with each other and/or in combination with any of the embodiments disclosed herein.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An orthopaedic prosthesis comprising:
   a tibial tray configured to be coupled to a surgically-prepared surface of the proximal end of a tibia, the tibial tray including (i) a platform having an upper surface and a bottom surface and (ii) a cavity defined by an inner sidewall and having an opening defined in the upper surface of the platform;
   a tibial insert coupled to the tibial tray, the tibial insert having (i) an upper bearing surface configured to contact a pair of femoral condyles, (ii) a bottom surface in contact with the upper surface of the tibial tray, and (iii) a stem extending downwardly from the bottom surface and received in the cavity of the tibial tray, the stem including a distal end having a threaded internal passageway;
   a screw positionable in the threaded internal passageway of the stem, wherein:
   (i) the distal end of the stem has a first width when the screw is positioned in the threaded internal passageway and (ii) the distal end of the stem has a second width when the screw is removed from the threaded internal passageway, the first width being greater than the second width; and
   wherein the tibial insert is rotatable with respect to the tibial tray when the screw is removed from the threaded internal passageway and prevented from rotating with respect to the tibial tray when the screw is positioned in the threaded internal passageway.

2. The orthopaedic prosthesis of claim 1, wherein the distal end of the stem includes a vertical slit, the vertical slit sized to allow the width of the distal end of the stem to be increased.

3. The orthopaedic prosthesis of claim 1, wherein the stem includes an outer wall, the outer wall being forced against the inner sidewall of the tibial tray when the screw is positioned in the first position.

4. The orthopaedic prosthesis of claim 1, wherein the inner sidewall of the tibial tray includes a slot defined therein and the distal end of the stem includes an outer rim, the outer rim being received in the slot of the inner sidewall.

5. The orthopaedic prosthesis of claim 1, wherein the tibial insert includes a tapered bore defined therethrough, the tapered bore extending from the upper bearing surface to the bottom surface, the threaded internal passageway forming a portion of the tapered bore.

* * * * *

UNITED STATES PATENT AND TRADEMARK OFFICE
CERTIFICATE OF CORRECTION

| | | |
|---|---|---|
| PATENT NO. | : 7,740,662 B2 | |
| APPLICATION NO. | : 11/859448 | |
| DATED | : June 22, 2010 | |
| INVENTOR(S) | : Gary D. Barnett et al. | |

It is certified that error appears in the above-identified patent and that said Letters Patent is hereby corrected as shown below:

Column 1 line 22, cancel the text "11/859,448" and insert the text --11/859,454--

Column 50, lines 16-17, cancel the text "positioned in the first position" and insert the text --removed from the threaded internal passageway.--

Signed and Sealed this
Twenty-second Day of February, 2011

David J. Kappos
*Director of the United States Patent and Trademark Office*